US011339362B2

(12) United States Patent
Lin et al.

(10) Patent No.: US 11,339,362 B2
(45) Date of Patent: May 24, 2022

(54) ORGAN CHIP TO MODEL MAMMALIAN JOINT

(71) Applicant: University of Pittsburgh—Of the Commonwealth System of Higher Education, Pittsburgh, PA (US)

(72) Inventors: Hang Lin, Pittsburgh, PA (US); Peter Alexander, Wexford, PA (US); Riccardo Lucca Gottardi, Pittsburgh, PA (US); Rocky Sung Chi Tuan, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 699 days.

(21) Appl. No.: 16/193,972

(22) Filed: Nov. 16, 2018

(65) Prior Publication Data

US 2019/0276784 A1 Sep. 12, 2019

Related U.S. Application Data

(60) Provisional application No. 62/588,203, filed on Nov. 17, 2017.

(51) Int. Cl.
*C12M 3/00* (2006.01)
*C12M 1/42* (2006.01)
(Continued)

(52) U.S. Cl.
CPC ............ *C12M 21/08* (2013.01); *C12M 35/08* (2013.01); *C12N 5/0697* (2013.01);
(Continued)

(58) Field of Classification Search
CPC ...... C12M 23/12; C12M 29/10; C12M 35/08; C12M 25/14; C12M 21/08; C12N 5/0697;
(Continued)

(56) References Cited

U.S. PATENT DOCUMENTS

2012/0040453 A1* 2/2012 Zal .......................... C12M 23/24
435/325
2016/0000969 A1* 1/2016 Altschuler .............. A61L 27/52
424/423
(Continued)

FOREIGN PATENT DOCUMENTS

WO  WO 2016/077118  5/2016
WO  WO 2017/062629  4/2017

*Primary Examiner* — Gautam Prakash
(74) *Attorney, Agent, or Firm* — Klarquist Sparkman, LLP

(57) ABSTRACT

Disclosed herein are various bioreactor devices that mimic the mammalian joint. The bioreactor device can include a series of bioreactor chambers that contain different components of the joint, such as bone, cartilage, synovium, nerve and ligament. At least two different nutrient fluid circulation systems connect subsets of the bioreactor chambers to differentially supply nutrient fluids at concentrations optimized for the tissue that the fluid nourishes. For example, relatively hypoxic fluid can be supplied to synovium and cartilage to mimic oxygenation in the joint compartment, but normoxic fluid can be supplied to the bone and other components that have an arterial supply that provides higher oxygen concentrations. One or more or all of the bioreactor chambers can be supplied with separate inlets through which perturbation agents (such as drugs or other agents) can be introduced to model the effect of the perturbations on different components of the system. In some cases, the system can include a well plate having a plurality of wells and a bioreactor situated in each well of the well plate.

19 Claims, 27 Drawing Sheets
(13 of 27 Drawing Sheet(s) Filed in Color)

(51) Int. Cl.
 *C12N 5/071* (2010.01)
 *A61L 27/50* (2006.01)
 *A61L 27/38* (2006.01)

(52) U.S. Cl.
 CPC .......... *A61L 27/3834* (2013.01); *A61L 27/50* (2013.01); *A61L 2300/414* (2013.01); *A61L 2430/02* (2013.01); *A61L 2430/10* (2013.01); *C12N 2502/1311* (2013.01); *C12N 2502/28* (2013.01); *C12N 2533/54* (2013.01)

(58) Field of Classification Search
 CPC ........ C12N 2502/1311; C12N 2533/54; C12N 2502/28; A61L 27/3834; A61L 2300/414; A61L 2430/02; A61L 2430/10; A61L 27/50
 See application file for complete search history.

(56) References Cited

U.S. PATENT DOCUMENTS

2016/0129155 A1 5/2016 Lin et al.
2016/0201037 A1 7/2016 Tuan et al.

* cited by examiner

Prior Art

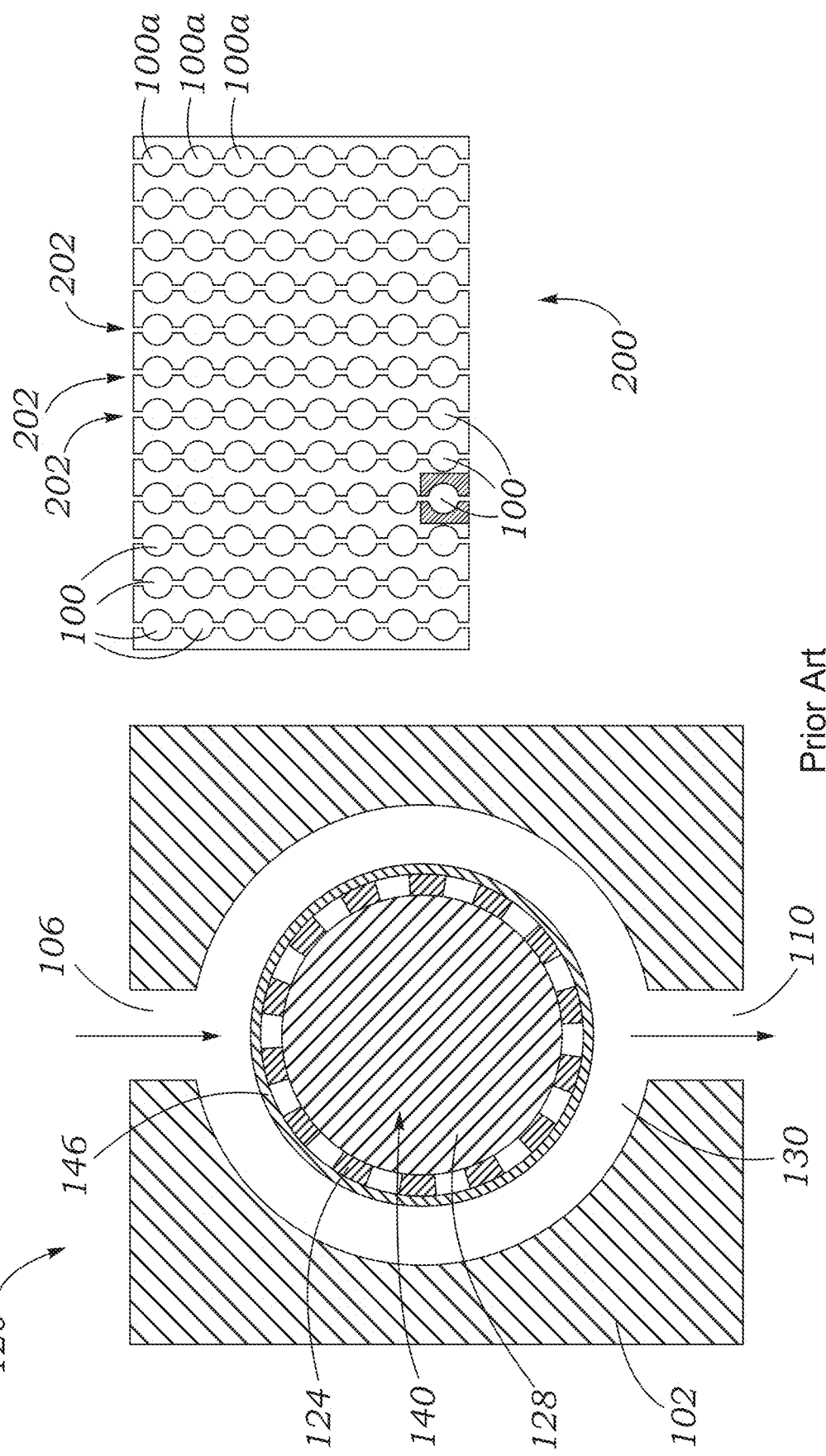

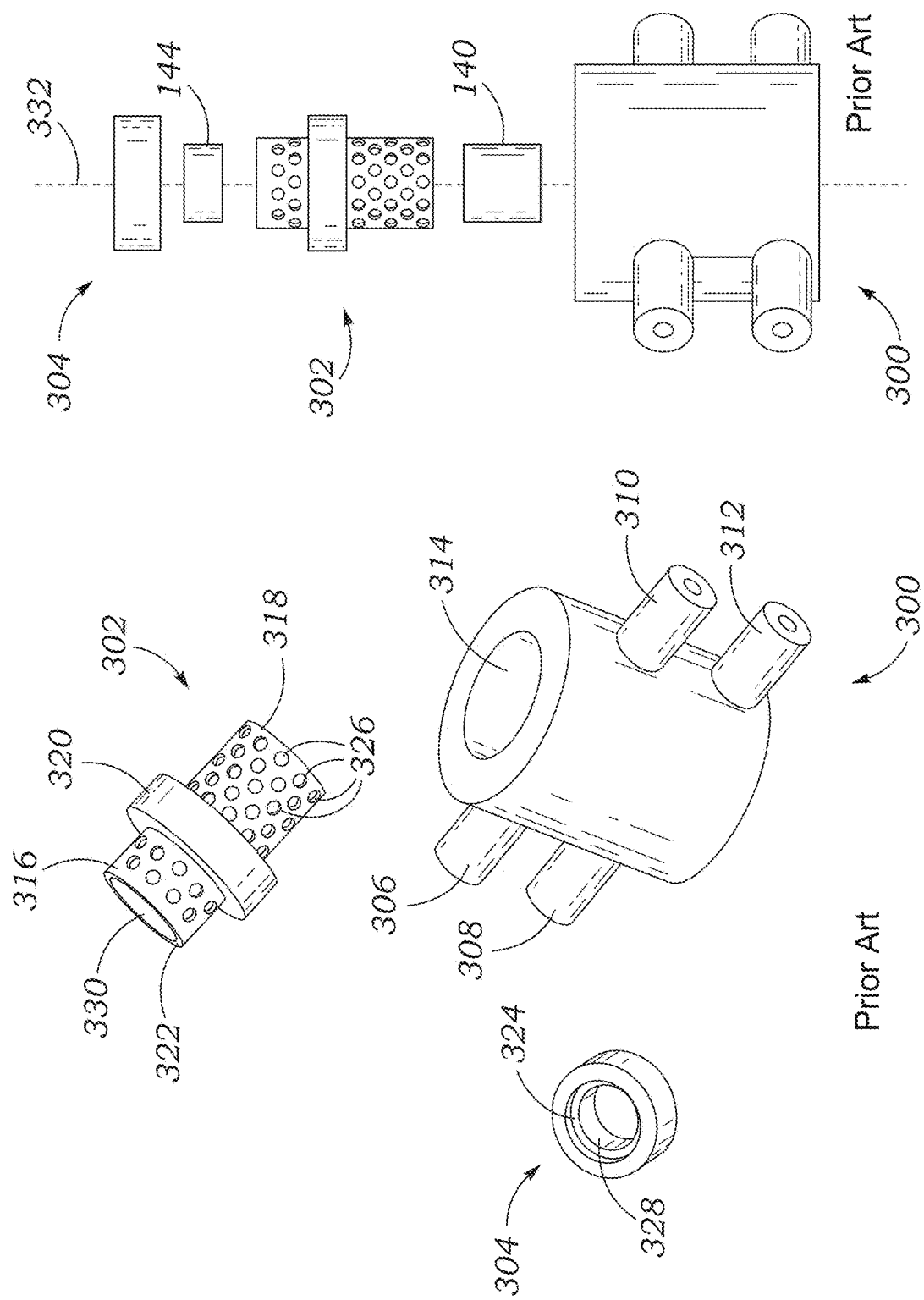

Prior Art

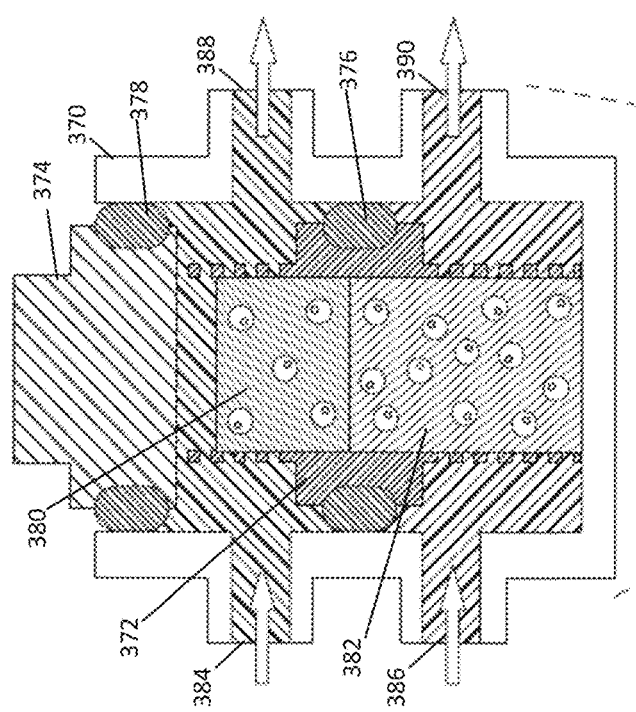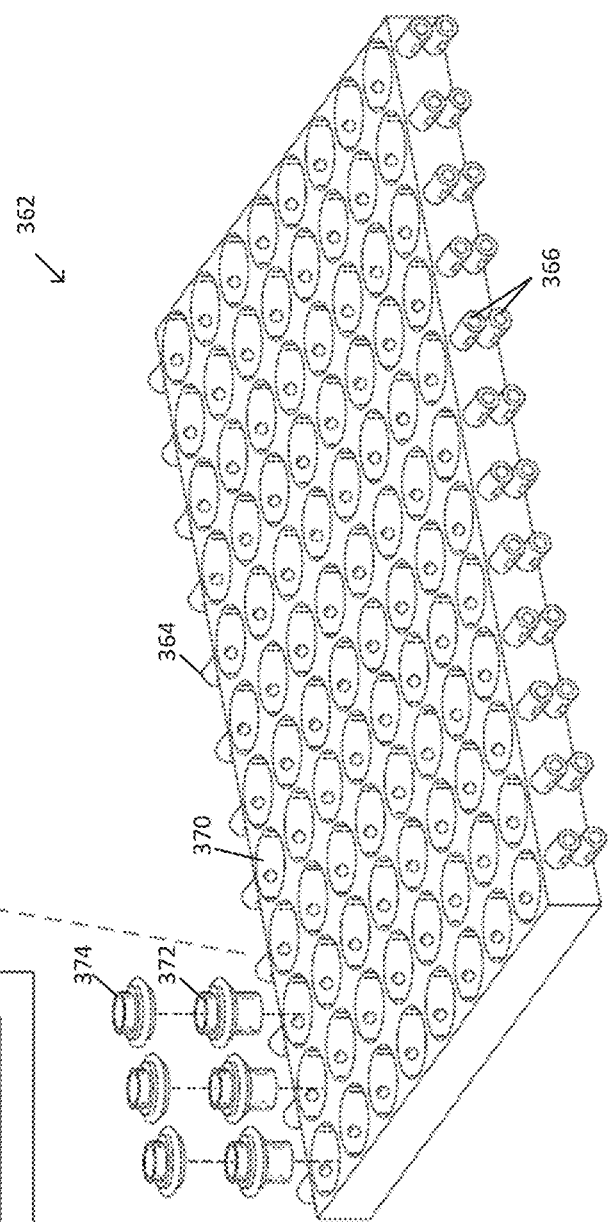
FIG. 5E
Prior Art

Prior Art

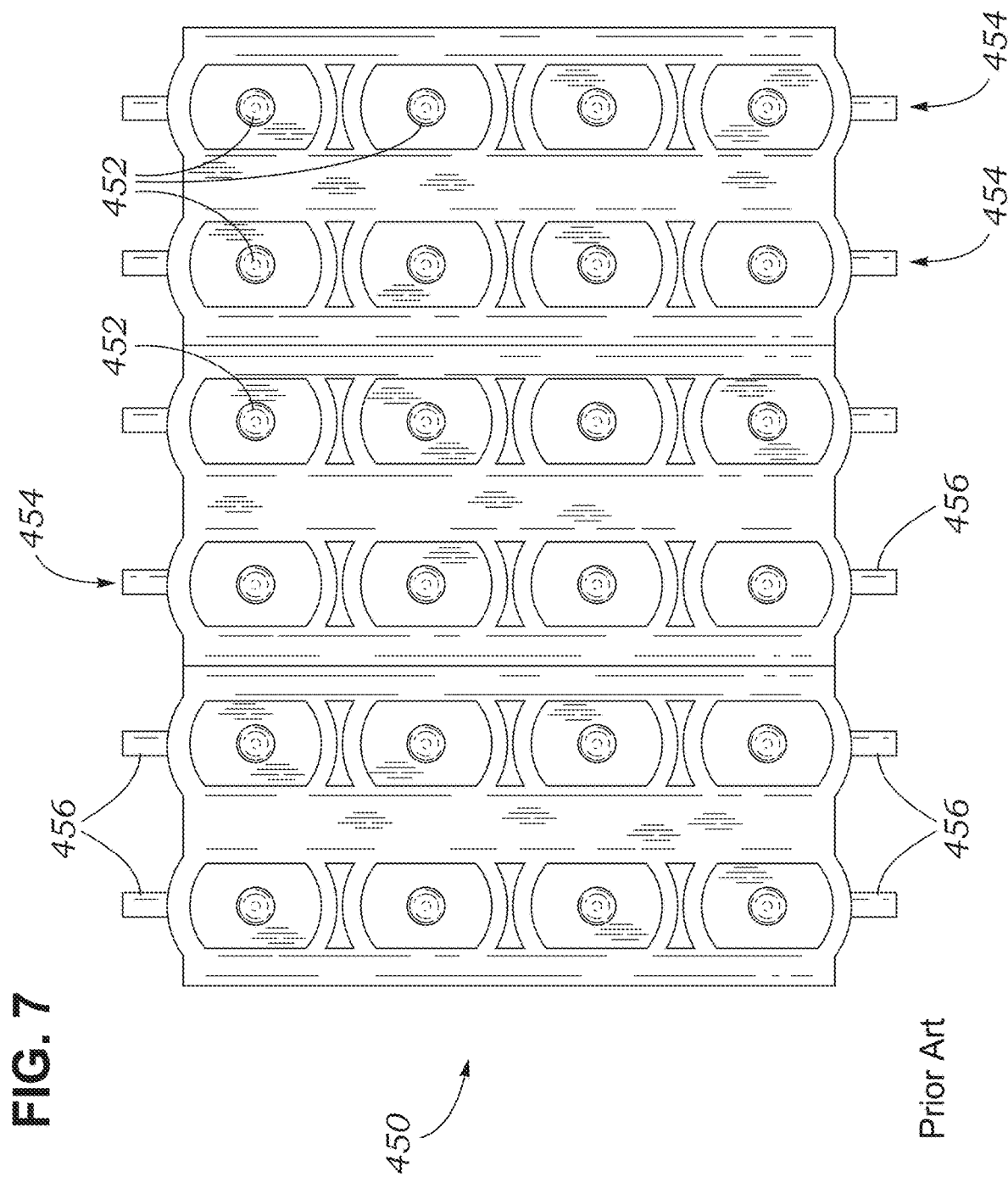

Prior Art

FIG. 12
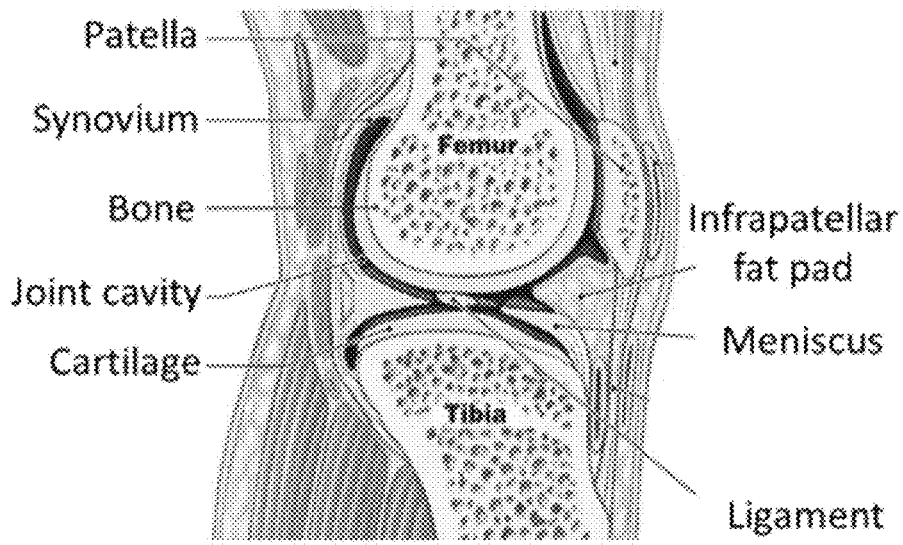
FIG. 13A
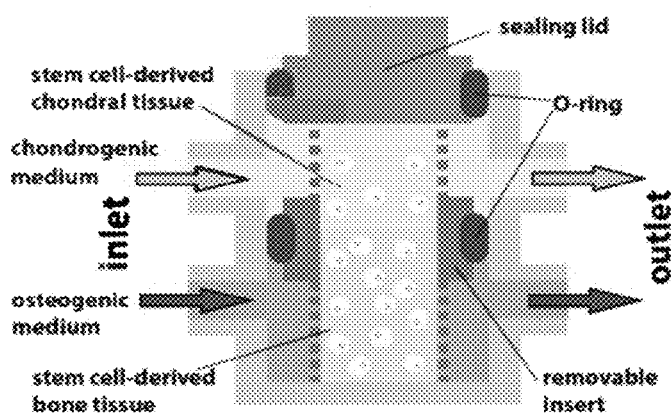
FIG. 13D
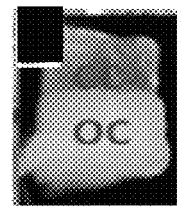
FIG. 13B       FIG. 13C
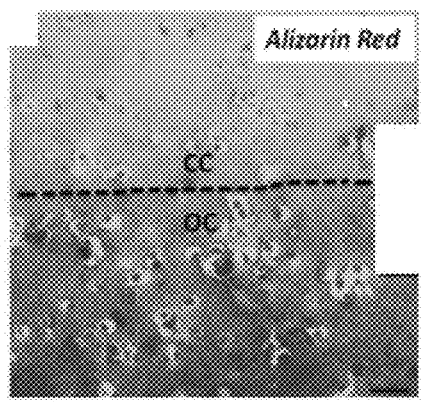    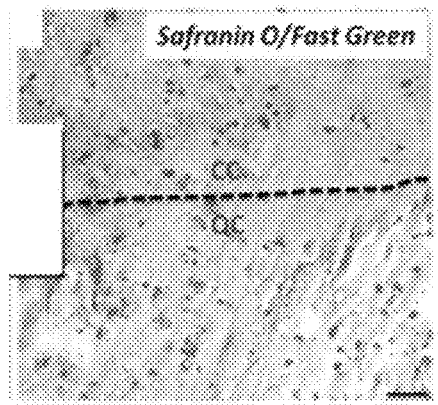

Cells: human mesenchymal stem cells

Photocrosslinkable methacrylated gelatin (*chondral component* – top)
+
Polycaprolactone scaffold (*osseous component* - bottom)

FIG. 26A FIG. 26B
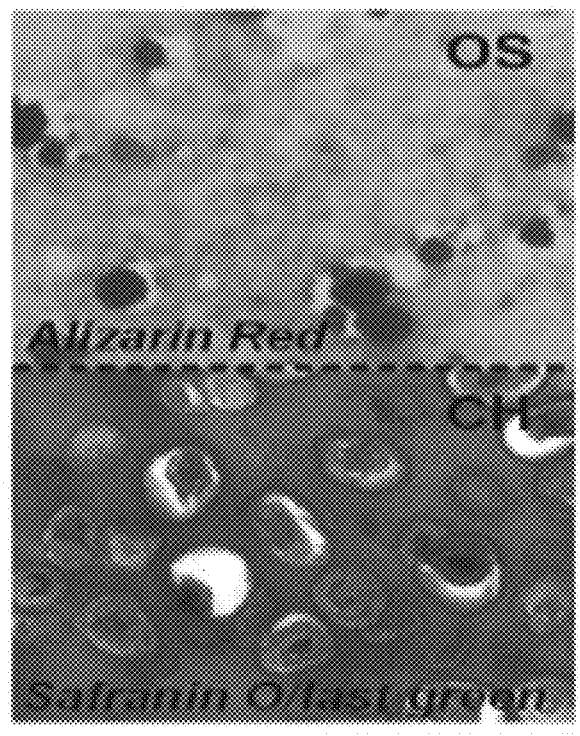 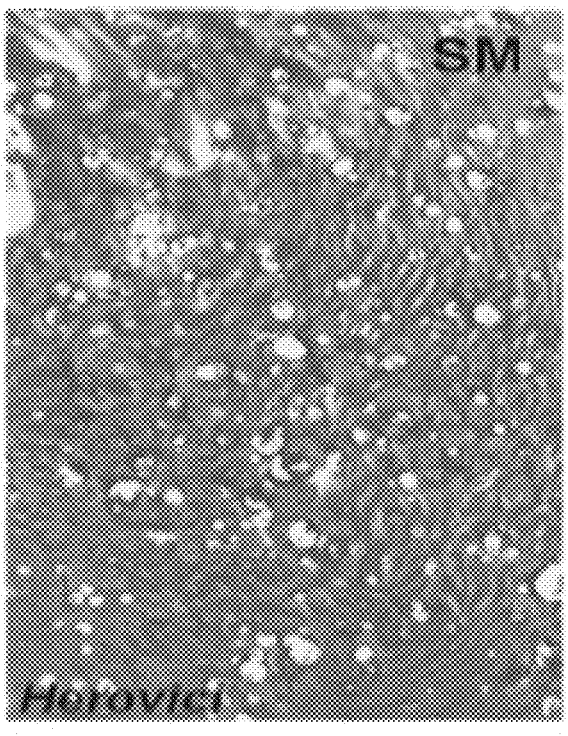
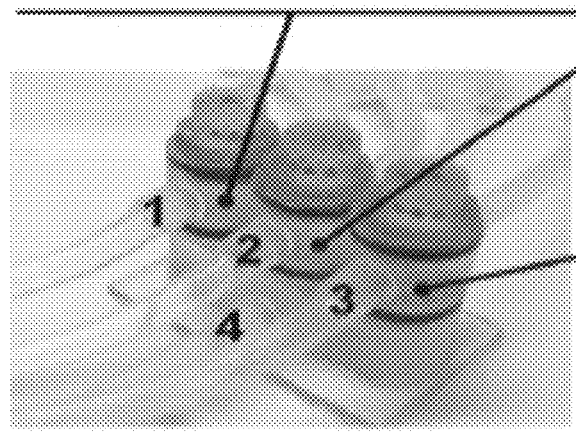 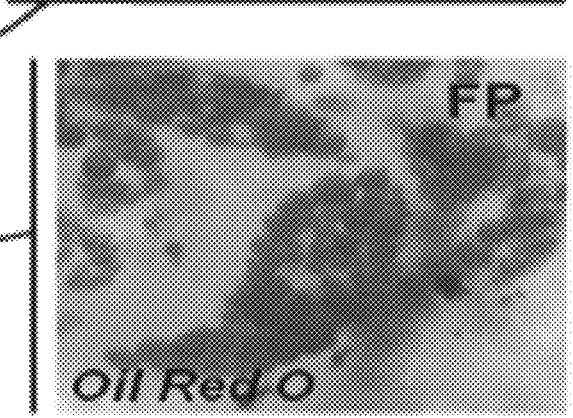
FIG. 26C FIG. 26D

FIG. 26E
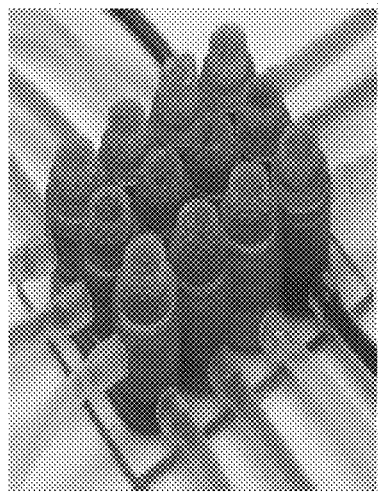
FIG. 26F
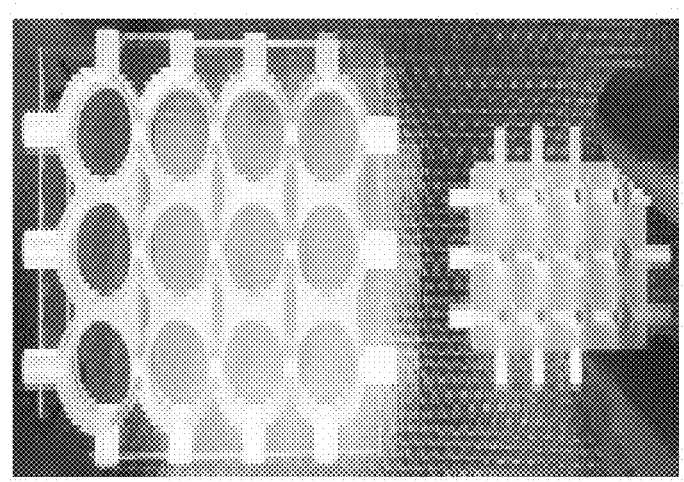
FIG. 26G
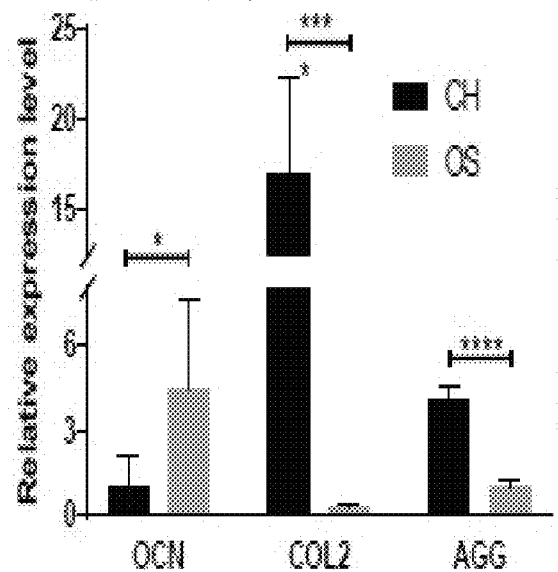
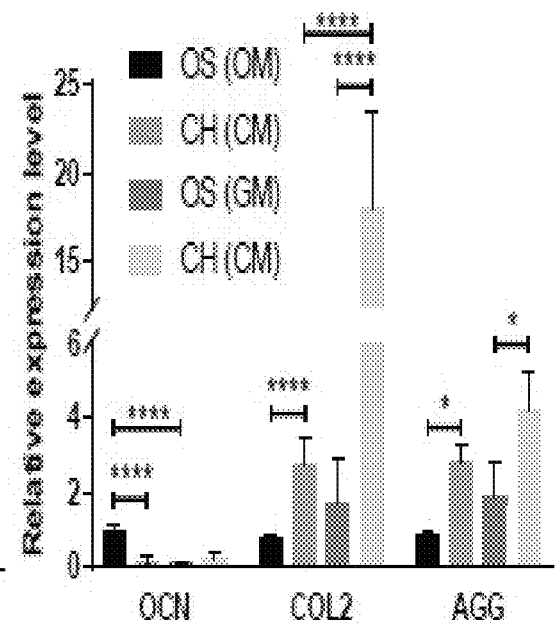

ORGAN CHIP TO MODEL MAMMALIAN JOINT

CROSS REFERENCE TO RELATED APPLICATION(S)

This claims the benefit of U.S. Provisional Application No. 62/588,203, filed Nov. 17, 2017, incorporated herein by reference in its entirety.

ACKNOWLEDGMENT OF GOVERNMENT SUPPORT

This invention was made with government support under grant number TR002136 awarded by the National Institutes of Health. The government has certain rights in the invention.

FIELD

The present disclosure relates to the engineering of a three-dimensional human micro-joint chip, physiologically analogous to the native joint and capable of modeling pathogenesis and treatment of joint diseases for the screening and development of disease-modifying treatments such as medications.

BACKGROUND

Trauma, inflammation, infection and aging can cause damages to joint tissues, ultimately leading to arthritic disorders, such as osteoarthritis (OA), septic arthritis and inflammatory arthritis, resulting in physical disabilities that compromise quality of life. However, no efficacious therapies are currently available. The limited progress in the development of disease-modifying medications (DMMs) is principally due to (1) an insufficient mechanistic understanding of disease onset and progression; (2) the inability to encompass the three-dimensional and multi-tissue nature of the synovial joint in early phase in vitro drug discovery; and (3) the limited utility of pre-clinical animal studies for early stage clinical efficacy and toxicity prediction, which result in unanticipated and costly clinical trial failures. Additionally, patient-specific etiology, progression of disease, and drug sensitivity profiles underscore the need for targeted personalizable therapy development.

Osteoarthritis (OA) is the most prevalent form of arthritis, affecting up to 15% of the adult population. Understanding the mechanisms underlying the pathogenesis of OA is important for the rational development of disease modifying OA drugs (DMOADs). Most studies on OA have focused on the investigation of either the cartilage or the bone component of the articular joint. However, OA is a chronic degenerative disease of the articular joint which involves cartilage, synovium, ligaments, bone, meniscus, tendon, and peri-articular muscle. Cartilage destruction is one of the common characteristics of OA progression, and results in malfunction of the affected joint. Normal articular cartilage is comprised of large amounts of extracellular matrix (mainly collagen type II), produced and maintained by chondrocytes, the sole cell type in the cartilage. During disease progression, net loss of cartilage matrix results from an imbalance between cartilage matrix degradation and synthesis by chondrocytes in the cartilage. Due to absence of vascularization in the articular cartilage, the capacity of self-repair in cartilage is limited, and currently, there is no effective therapy for the treatment of OA except relieving the symptoms of the diseases until the joints need to be replaced by surgery.

OA involves more than simply degeneration of the articular cartilage; it is in a disease of the osteochondral tissue complex. The osteochondral junction is highly structured; the uppermost superficial zone is characterized by elongated chondrocytes with collagen fibrils aligning parallel to the articular surface. In the middle/intermediate zone, rounded chondrocytes and collagen fibrils are less organized relative to the surface. In the deep zone, vertical columns of chondrocytes and fibers are organized perpendicular to the articular surface. The highest concentration of proteoglycans is found in the deep zone. Adjacent to deep cartilage is the calcified cartilage zone, which is characterized by larger and more dispersed hypertrophic chondrocytes. A wavy basophilic matrix, known as the tidemark, highlights the boundary between the deep and calcified cartilage zones. Vertically oriented collagen fibers pass through the tidemark from the deep zone to the calcified cartilage and are important for transferring mechanical forces. Overall, the calcified zone marks the transition from soft cartilage to stiff subchondral bones and is important for attaching the non-calcified cartilage to bone. The subchondral bone is interdigitated with calcified cartilage, but, interestingly, the collagen fibers do not extend from the calcified zone to the bone. This physical linkage between cartilage and bone is a critical component in the pathogenesis of degenerative diseases such as OA.

OA may begin in the cartilage or the bone and whether subchondral bone or articular cartilage is the more appropriate target for disease modifying OA drug (DMOAD) development. Supporters of the "bone first" side of the debate maintain that, as the "substrate" for articular cartilage, subchondral bone plays a support role in cartilage health, and that any perturbations to subchondral bone are amplified as pathological conditions and are transferred from bone to cartilage. For example, studies have shown that osteophyte formation and changes in subchondral bones appear before measurable changes in articular cartilage thickness as well as related joint space narrowing. Another group of studies suggest that healthy subchondral bone is essential for healthy cartilage. In tissue plugs cultured in vitro, bone tissue preserves chondrocyte survival. To some extent, the conventional wisdom has been that healthy subchondral bone presents an impenetrable, impermeable barrier. However, it is possible that cartilage receives nutrients, cytokines, hormones, and other biological signals from bone in vivo, and vice versa.

Proponents of the "cartilage first theory" argue that, while early changes to cartilage during OA are clearly coupled to bone alterations via mechanical and soluble factors, changes to the bone seem to be secondary to alterations in articular cartilage. Supporting evidence suggests that OA changes to cartilage alter the mechanical environment of the bone cells and induce them, in turn, to modulate tissue structure. Several studies report that thickening of calcified cartilage along with tidemark advancement contributes to thinning of articular cartilage. This leads to increased mechanical stresses in the matrix of the deep zone of cartilage and contributes to OA cartilage deterioration.

Therefore, there is a need in the art for a physiologically relevant in vitro model that includes all components of the joint, such as the cartilage, bone, synovium and infrapatellar fat pad (IPFP), and retains the heterogeneity of the various tissues within the joint, to provide a model of the joint, and for use in developing more effective or and personalized therapies for diseases of the joint.

SUMMARY

Provided herein are cell-based microphysiological joint (mJoint) tissue bioreactors that include the osteochondral (bone/cartilage) complex, the synovium and the adipose tissue. Other joint components, such as meniscus, ligaments and nerve may also be included in separate bioreactor chambers incorporated into the tissue bioreactor. In some embodiments, the tissue bioreactor replicates known stratifications and physiologic conditions in human OA, inflamed arthritis and diabetic-induced complications of diabetes and other joint diseases (for example in the knee) to study and mimic the cause of onset, effect on target tissue elements and disease progression. The bioreactors can be used to model a mammalian joint, such as a human joint.

In some embodiments, disclosed is a tissue bioreactor that mimics an osteochondral complex of a mammalian joint, wherein the bioreactor includes: a first reactor chamber containing osseous or osteogenic tissue and/or cartilaginous or chondrogenic tissue; a second reactor chamber containing synovial tissue; a third reactor chamber containing adipose tissue, adipogenic tissue, or macrophages; a first fluidic passageway that forms a fluid circuit for circulating hypoxic tissue-specific nutrient medium through the first and second reactor chambers but not the third reactor chamber; a second fluidic passageway that forms a fluid circuit for circulating normoxic tissue-specific nutrient medium through the first, second and third reactor chambers; a perturbation source configured to provide a preselected perturbation to at least one of the reactor chambers or one or both of the first and second fluidic passageways.

In additional embodiments, disclosed is a tissue bioreactor that mimics a mammalian joint, wherein the bioreactor includes: a first reactor chamber containing separate layers of osteocytes and chondrocytes separated by a layer of mesenchymal cells; a second reactor chamber containing synovial tissue; a third reactor containing macrophages; a fourth reactor containing adipose cells; a first fluidic passageway that forms a fluid circuit for circulating hypoxic tissue-specific cell culture medium through the first and second reactor but not the third reactor; a second fluidic passageway that forms a fluid circuit for circulating normoxic tissue-specific cell culture medium through the first, second and third reactor; and a perturbation source configured to provide a preselected perturbation to at least one of the reactor chambers, or one or both of the first and second fluidic passageways.

In further embodiments, disclosed is a bioreactor that includes: i) a first chamber including a) a first tissue including osteoblasts within a first scaffold, and b) a second tissue including chondrocytes within a second scaffold, wherein the first scaffold is above the second scaffold within the first chamber, and wherein the first tissue and the second tissue are in functional contact and wherein there optionally is an additional tissue layer or a semi-permeable membrane between the osteoblasts and the chondrocytes; ii) a second chamber including a third tissue comprising synovial cells within a scaffold; iii) a third chamber including fat pad cells within a scaffold; iv) an influx conduit for supplying a first nutrient fluid to the first tissue in the first chamber, and an efflux conduit for removal of the first nutrient fluid from the first tissue in the first chamber, wherein the first nutrient fluid comprises serum in high concentration under normoxic conditions; and v) an influx conduit for a supplying second nutrient fluid into the second tissue in the first chamber, and an efflux conduit for removal of the second nutrient fluid from the second tissue in the first chamber, wherein the second nutrient fluid comprises serum in low concentration under hypoxic conditions. The first and second nutrient fluids maintain separation from each other through the functional contact between the first tissue in the first scaffold and second tissue in the second scaffold, and wherein each of the first, second, third and fourth tissues is only exposed to their tissue-specific medium while remaining in direct contact with each other. The bioreactor can also include perturbation source that provides a preselected perturbation to at least one of the first, second, third and fourth tissues.

In more embodiments, a bioreactor is disclosed that includes: i) a first reactor chamber included an upper part and a lower part, wherein the first reactor chamber includes synovial cells within a scaffold in both the upper part and the lower part, wherein the upper part has an inlet and an outlet for a first normoxic medium; ii) a second reactor chamber including an upper part and a lower part, wherein the second reactor chamber includes a) osteoblasts within a first scaffold in the upper part, and b) chondrocytes within a second scaffold in the lower part, and wherein the osteoblasts and the chondrocytes are in functional contact at the interface between the upper part and the lower part, and wherein the second reactor chamber has an inlet and an outlet for circulating a second normoxic medium through the osteoblasts in the upper part and an inlet and an outlet for circulating first hypoxic medium through the chondrocytes in the lower part; iii) a third reactor chamber with an upper part and a lower part, wherein the third reactor chamber includes fat pad cells within a scaffold in both the upper part and the lower part, wherein the third reactor chamber has an inlet and an out let for circulating a third normoxic medium through the fat pad cells in the upper part; wherein the lower parts of the first, second and third reactor chambers are interconnected, such that the hypoxic medium entering through the inlet contacts the synovial cells in the lower part of the first reactor chamber, chondrocytes in the lower part of the second reactor chamber, and fat pad cells in the lower part of the third reactor chamber.

Methods of using these bioreactors, such as to model a mammalian joint, for example a human joint, are also disclosed.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows a schematic, cross-sectional plan view of an exemplary bioreactor, a plan view of an exemplary array of bioreactors, and a location of the exemplary bioreactor in the exemplary array of bioreactors.

FIG. 3 shows three-dimensional renderings of an exemplary shell of a bioreactor, inner body of a bioreactor, and upper ring of a bioreactor, in perspective views.

FIG. 4 shows a three-dimensional rendering of the components of an exemplary bioreactor, in an exploded view.

FIG. 5E is a schematic representation of a multiwell, dual chamber bioreactor system, with a 96 well bioreactor platform shown on the right, and a cross-sectional view of a single bioreactor on the left.

FIG. 7 shows an image of an exemplary array of 24 bioreactors, from a top plan view.

FIG. 12 shows the structure of the human joint, including the bone, cartilage and infrapatellar fat pad.

FIGS. 13A-13D. FIG. 13A shows a diagram of an individual bioreactor. The osteochondral construct within the insert creates the final separation between the upper and lower medium conduits. FIGS. 13B-13C shows the histology of the engineered osteochondral construct. Top, chondral component (CC); bottom, osseous component (OC). Dashed lines indicate the border between CC and OC. Bar=100 µm. FIG. 13D shows a macroscopic view of the engineered osteochondral construct.

FIGS. 26A-26G. Integration of the osteochondral complex, synovial membrane (SM), and fat pad (FP) tissues to form microJoint. (A-D) mJoint bioreactor (C), and histological imaging of the engineered joint components (A, B, D); (E) a high-yield bioreactor capable of culturing 4× numbers of tissues; (F) Two types of microJoint chips for invasive, or non-invasive and high-throughput analysis; (G) expression of bone (OS) and cartilage (CH) marker genes before (left) and after (right) 28 days integration culture.

DETAILED DESCRIPTION

Figure 1:
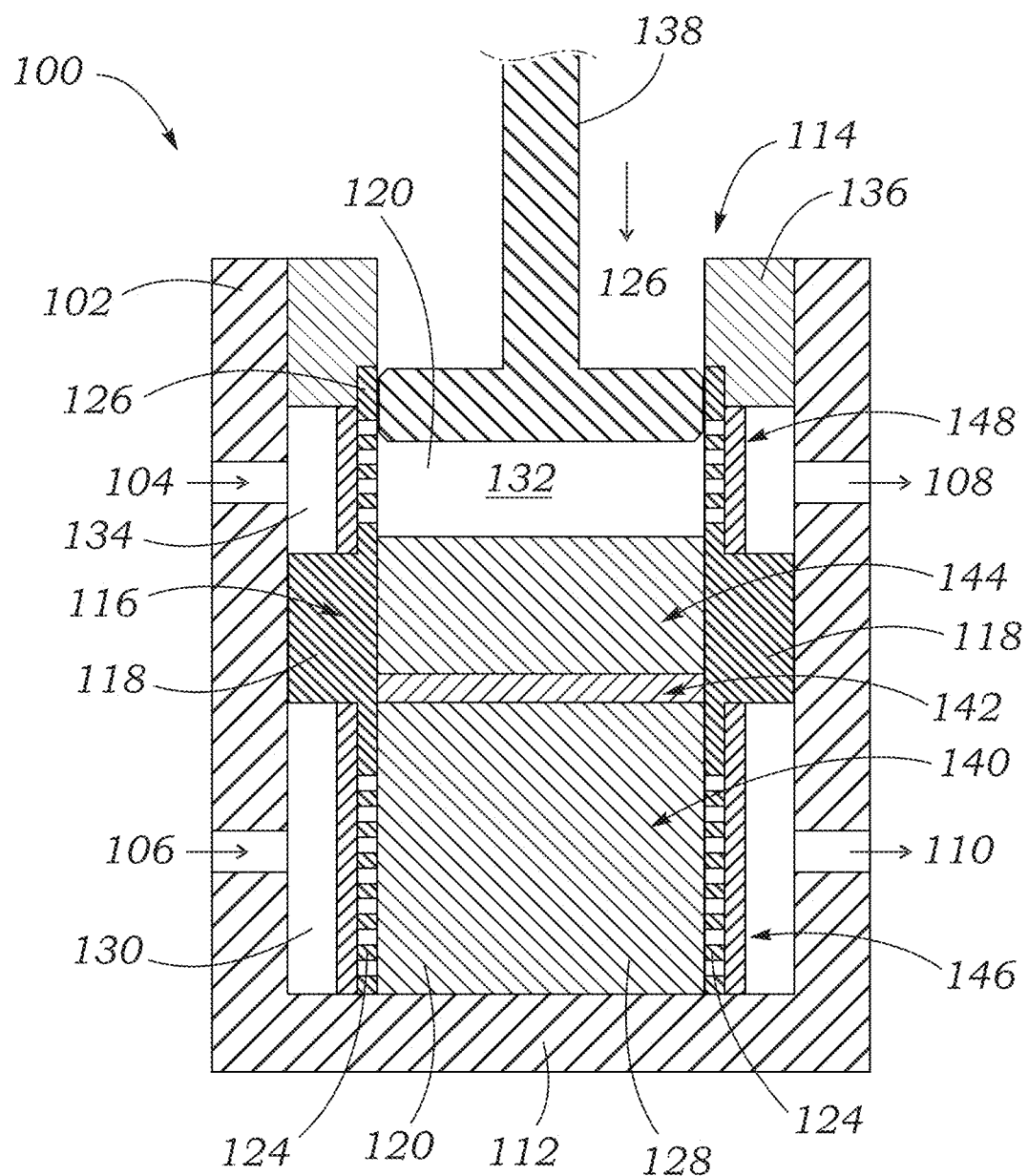
FIG. 1 shows a schematic, cross-sectional side view of an exemplary bioreactor having a microsystem of plural different tissue types growing therein.

Disclosed are cell-based microphysiological joint (mJoint) tissue bioreactors that include the osteochondral (bone/cartilage) complex, the synovium and the adipose tissue. These bioreactors include mammalian cells, such as human or veterinary cells. Other joint components, such as meniscus, ligaments and nerve may also be included in separate bioreactor chambers incorporated into the tissue bioreactor. In some embodiments, the tissue bioreactor replicates known stratifications and physiologic conditions in human OA, inflamed arthritis and diabetic-induced complications of diabetes and other joint diseases (for example in the knee) to study and mimic the cause of onset, effect on target tissue elements and disease progression. In some embodiments, the tissue bioreactor is engineered using potentially autologous cells to preserve an individual's genetic contribution, and the different tissues that constitute the joint are housed in a bioreactor with microfluidic circulation to simulate in vivo tissue conditions. The cells can be all human. In further embodiments, the tissue bioreactor models a whole joint, and is suitable for the initiation or acceleration of joint diseases with different pathophysiologic mechanisms to allow the investigation of disease onset and progression, the development of therapeutics that target different tissues and/or pathways, and the assessment of direct and indirect effects of candidate drugs.

In some embodiments, the bioreactor is configured to have at least two separate circulation systems connected to multiple reactor chambers, each reactor chamber reproducing a different tissue or tissue combination/complex. The separate circulation systems are independently provided with nutrients and/or fluids, and inlets and outlets to introduce stimuli and/or therapeutics. The bioreactor can be incorporated into a platform (referred to as a chip) that contains all the components of the bioreactor, including the reactor chambers, the cells, and the fluidics for circulating nutrient media through the system.

In more embodiments, each component bioreactor chamber is supplied by nutrient fluid (such as universal medium) in a fluid circuit that has an oxygen tension suitable for the tissues on that fluid circuit. For example, a fluid circuit that supplies bioreactor chambers that contain cartilage or synovium or ligament, or contacts one face of cartilage or synovium or ligament, would supply medium having a relatively low oxygen content that mimics the oxygenation of synovial fluid that bathes these joint components in a mammalian joint. However other bioreactor chambers that contain tissue having a higher oxygen tension in vivo (such as adipose tissue, bone, nerve, or macrophages) would be on a separate fluid circuit that supplies fluid having an oxygen tension more suitable to the in vivo oxygen tension of those tissues (normoxic fluid).

In some embodiments the tissue bioreactor mimics the condition of a mammalian joint. The bioreactor includes a first reactor chamber containing osseous or osteogenic tissue and/or cartilaginous or chondrogenic tissue, a second reactor chamber containing synovial tissue, a third reactor chamber containing adipose tissue, adipogenic tissue or macrophages. A first fluidic passageway forms a fluid circuit for circulating hypoxic tissue-specific nutrient medium through the first and second reactor chambers but not the third reactor chamber, and a second fluidic passageway forms a fluid circuit for circulating normoxic tissue-specific nutrient medium through the first, second and third reactor chambers. A perturbation source may also be provided to induce preselected perturbations to at least one of the reactor chambers or one or both of the first and second fluidic passageways.

In additional embodiments, the third reactor chamber contains adipose tissue and the tissue bioreactor further comprises a fourth reactor chamber containing macrophages, wherein the second fluidic passageway circulates the normoxic tissue-specific fluid through the third and fourth reactor chamber. In further embodiments, the first reactor chamber contains separate layers of osseous and cartilaginous tissue that are optionally separated by a layer of mesenchymal cells. In yet another embodiment, the third reaction chamber comprises macrophages and the tissue reactor further comprises a fourth bioreactor comprising osseous but not cartilaginous tissue. The first, second, third and fourth reactor chambers may be microscale chambers, such as chambers contained in separate microwells of a multiwell plate.

In some disclosed embodiments, the osseous tissue comprises osteocytes and/or osteocalsts, the cartilaginous tissue comprises chondrocytes, and the adipose tissue comprises adipocytes. In some embodiments the synovial tissue comprises synoviocytes and macrophages. Alternatively, or in addition, the osseous or cartilaginous tissue comprises mesenchymal stem cells (MSCs) or induced pluripotent stem cells (iPSCs) that produce osteocytes or chondrocytes. Similarly, the adipose tissue comprises mesenchymal stem cells (MSCs) or induced pluripotent stem cells (iPSCs) that produce adipocytes, or the adipocytes themselves.

The tissue bioreactors disclosed herein mimic the condition of a mammalian joint and can be used in methods of identifying physiologic and pathophysiologic mechanisms of joint health and disease. For example, the interaction of adipose tissue and inflammatory cells on the osteochondral complex may be identified, as may occur in diabetes.

In the disclosed methods, hypoxic cell culture medium is circulated through the first fluidic passageway and a normoxic cell culture medium is circulated through the second fluidic passageway of the tissue bioreactor. In the disclosed methods, the first and second fluidic passageways transport fluids to and from chambers by diffusion or perfusion. The cells in the tissue bioreactor chambers may all be from one mammalian subject (such as an individual person) to help maintain genetic homogeneity between the different tissue components in the bioreactor.

To demonstrate the effects of different biological perturbations on the system, one or more perturbation can be introduced into at least one of the first and second fluidic passageways, or both of them. Since some fluidic passageways are separate and do not mix, different perturbations can be supplied to the different combinations of tissue for each circuit, and the culture media for each of the circuits can be optimized for the separate tissue compartments supplied by each of the fluid circuits.

The supplied perturbation may be one or more of a chemical perturbation, a toxicological perturbation, a mechanical perturbation, a physical perturbation, or a biological perturbation. In more specific examples, the perturbation may be one or more of a disease initiator, an active agent, a chemical compound, a hormone, an inflammatory agent, a disease-modifying agent or a therapeutic agent, such as an anti-osteoarthritic agent, anti-diabetic agent, a cartilage anabolic or catabolic gene sequence, a bone anabolic or catabolic gene sequence, a macrophage stimulator, or a macrophage inhibitor. In other examples, the biological perturbation comprises wear debris.

In some embodiments, tissue bioreactors are disclosed that include three or more reactor chambers. The first reactor chamber contains a first and a second tissue having one or more types of cells; the second reactor chamber contains a third tissue having one or more types of cells; and the third reactor chamber contains a fourth tissue having one or more types of cells. The first tissue is distinct from the second tissue, the third tissue and the fourth tissue; the second tissue is distinct from the first tissue, the third tissue and the fourth tissue; the third tissue is distinct from the first tissue, the second tissue and the fourth tissue; and the fourth tissue is distinct from the first tissue, the second tissue and the third tissue. In some embodiments, a type of cells is oriented vertically relative to a different type of cells within the same chamber, such that one type of cells is in functional contact with a different type of cells within the same chamber. In some embodiments, the reactor chamber has two chambers that are vertically oriented, and different types of cells in each chamber. The cells can be in a tissue culture scaffold.

The disclosed bioreactor can include at least one inlet and outlet, such that a first nutrient fluid supplied laterally into the bioreactor; and a second nutrient fluid supplied laterally into the bioreactor. The first and second nutrient fluids do not mix other than through the functional contact between the first and second tissues, and each type of cells is only exposed to their tissue-specific medium while remaining in direct contact with each other.

In some embodiments, the disclosed bioreactor further comprises a perturbation source configured to provide a preselected perturbation on at least one of the tissues. In one embodiment, the first tissue in the first reactor chamber comprises osteoblasts and/or osteoclasts, the second tissue in the first chamber comprises chondrocytes, and an additional tissue layer between the first tissue and the second tissue. The osteoblasts/osteoclasts and chondrocytes may be engineered from mesenchymal stem cells or from induced pluripotent stem cells within the bioreactor. The additional tissue layer may comprise a mesenchymal stem cell layer situated between the first and second tissues and physically isolating the first and second tissues from one another. In one embodiment, the third tissue in the second chamber comprises synovial cells (fibroblasts and macrophages). The synovial cells may be generated from mesenchymal stem cells or from induced pluripotent stem cells within the bioreactor. In an additional embodiment, the fourth tissue in the third chamber comprises fat pad cells. The fat pad cells may be generated from mesenchymal stem cells or from induced pluripotent stem cells within the bioreactor. The disclosed bioreactor may further comprise a fourth chamber comprising macrophages. The macrophages may be generated from monocytes, mesenchymal stem cells or from induced pluripotent stem cells within the bioreactor.

In one embodiment, the preselected perturbation is one or more of a chemical perturbation, a toxicological perturbation, a mechanical perturbation, a physical perturbation, or a biological perturbation. The preselected perturbation may comprise one or more of a disease initiator, an active agent, a chemical compound, a hormone, an inflammatory agent, a disease-modifying agent or a therapeutic agent.

In an additional embodiment, the first and second nutrient fluids transport fluids and molecules to and from the chambers by diffusion. In a different embodiment, the first and second nutrient fluids transport fluids and molecules to and from the chambers by perfusion. In one aspect, the first nutrient fluid comprises serum in high concentration under normoxic conditions, and the second nutrient fluid comprises serum in low concentration under hypoxic conditions.

The one or more types of cells may be from the same subject. In one embodiment, the subject is a mammal with a disease. The disease can be one or more of osteoarthritis, a diabetes-associated joint complication, osteosarcoma, or a bone tumor. The preselected perturbation may comprise a disease-modifying agent, which may be one or more of an anti-osteoarthritic agent, anti-diabetic agent, a cartilage anabolic or catabolic gene sequence, a bone anabolic or catabolic gene sequence, a macrophage stimulator, or a macrophage inhibitor.

In a further embodiment, a method is provided, that comprises providing the disclosed bioreactor, introducing a biological perturbation into at least one of the first and second nutrient fluids; and determining the effect of the biological perturbation on one or more tissues. In one embodiment, the biological perturbation comprises wear debris, and the one or more tissues comprise macrophages. The macrophages may be generated from mesenchymal stem cells or from induced pluripotent stem cells within the bioreactor. In one aspect, the bioreactor comprises a clear sealing lid, and the effect of the biological perturbation is monitored through the sealing lid.

A bioreactor is provided, which can include an upper chamber having inlet and outlet ports and a lower chamber having inlet and outlet ports. The inlet ports can be fed by the same or independent sources of biological nutrients, such as liquid cell growth medium, that is perfused through each chamber from the inlet port to the outlet port. The liquid cell growth medium may include serum in high concentration or in law concentration under normal levels of oxygen (normoxia), or under low oxygen tension (hypoxia). A first tissue can be situated in the upper chamber so as to be exposed to the biological nutrients fed through the upper inlet port, and a second tissue can be situated in the lower chamber so as to be exposed to the biological nutrients fed through the lower inlet port. In certain embodiments, one or more additional tissue layers can be situated at an interface that extends partially or completely between the first and second tissues. For example, the additional tissue layer may be a stem cell layer that can differentiate into the first tissue and/or the second layer, and/or that mediates biochemical communication between those layers. In particular examples, the additional layer is a stem cell layer of ectoderm, mesenchyme, or endoderm. In some embodiments, the upper chamber and second chamber can establish substantially separate microenvironments for the first and second tissue by supplying separate media or nutrient flow through the upper and lower inlet ports. Biochemical communication between the separate microenvironments can occur via biochemical signals produced by the additional intermediate layer at the interface instead of via the nutrient media flow.

One exemplary application of the devices, systems and methods described herein is in improved studies of the osteochondral complex and OA. While previous OA studies have focused on the investigation of either the cartilage or the bone component of the articular joint, the osteochondral complex represents a more physiologically relevant target as OA ultimately is a disorder of osteochondral integrity and function. Thus, interactions between both bone and cartilage are central to OA progression, and in studying OA, bone and cartilage are capable of being studied together instead of separately. Thus, the present disclosure describes 3D microtissue constructs including cartilage, bone, synovium and infrapatellar fat, in order to appropriately study the osteochondral environment and OA in vitro.

Different osteogenic and chondrogenic tissue components can be produced using adult human mesenchymal stem cells (MSCs) derived from bone marrow and adipose seeded within biomaterial scaffolds photostereolithographically fabricated with a well-defined internal architecture, or induced pluripotent stem cells (IPSCs) that differentiate into appropriate tissue-specific lineages. The use of MSCs and iPSCs overcomes the challenge posed by the limited availability of native chondrocytes, osteoblast, synoviocytes, macrophages and adipocytes. A 3D perfusion-ready container platform, such as a 3D printed platform, can house and maintain an osteochondral microsystem having any combination or all of the following features: (1) an anatomic cartilage/bone biphasic structure with a functional interface; (2) all tissue components derived from a single stem cell, such as an adult mesenchymal stem cell or an induced pluripotent stem cell source to eliminate possible age/tissue type incompatibility; (3) individual compartments to constitute separate microenvironments, for example for the "synovial," "fat pad," "cartilage" and "osseous" components; (4) accessible individual compartments which can be controlled and regulated via the introduction of bioactive agents or candidate effector cells, and tissue/medium sampling and compositional assays; and (5) compatibility with the application of mechanical load or other perturbations, such as chemical, toxicological and other physical perturbations. In certain embodiments, the container platform is dimensioned to fit within the wells of standard multiwell tissue culture plates, such as 24, 48, or 96 well plates, to perform high-throughput assays. The bioreactor can also have remote imaging capability to allow non-invasive functional monitoring of the bioreactor tissues. This design allows the chondral and osseous components of the biphasic construct to be exposed only to their tissue-specific media while remaining in direct contact with each other. Thus, the disclosed bioreactor constitutes an ideal environment to study the response of different tissues to inflammation or hormone stimulation, and the biology of cartilage-bone communication, and replicate known stratifications in human OA, inflamed arthritis, and diabetic complications of knee joint, including cause of onset, effect on target tissue elements and disease progression.

The consequences of external perturbations, such as mechanical injury, exposure to drugs or inflammatory cytokines, and compromised bone quality, on degenerative changes in the cartilage component can be examined in the osteochondral microsystem as a first step towards its eventual application as an improved and high-throughput in vitro model for prediction of efficacy, safety, bioavailability, and toxicology outcomes for candidate DMOADs. For example, the effect of corticosteroids or osteoactive agents on the different tissue types, such as bone and cartilage tissue, can be assessed. In addition, drug screening can be performed to identify potential therapeutic agents to treat OA, as well as targeted treatments in different subpopulations of subjects affected by OA.

In some embodiments, a bioreactor can include a fluidic well plate having dimensions equivalent to those of standard laboratory multi-well plates. The fluidic well plate can have various numbers of wells, such as one well, six wells, twelve wells, twenty-four wells, or ninety-six wells. The wells of the well plates can be arranged in a grid having rows and columns, and a row or a column of wells can be fluidically connected by a first conduit feeding upper portions of each of the wells in the row or column and by a second conduit feeding lower portions of each of the wells in the row or column. Each conduit can begin and terminate at the end of the plate at an inlet or an outlet port.

In some embodiments, a bioreactor can include a fluidic well insert configured to fit tightly within one of the wells of the fluidic well plate and to support biological tissues at an interior of the insert. The insert can include a circumferential flange which seals the insert against the inside surface of one of the wells of the fluidic well plate, thereby separating the respective well into the upper and lower portions fed by the first and second conduits, respectively. The insert can be hollow and thus biological tissues can be housed inside the insert. The circumferential flange can separate an upper portion of the insert from a lower portion of the insert, and each of the upper and lower portions of the insert can include pores through which fluids can flow. The insert can be configured to be situated within a standardized, commercially available well plate.

In some embodiments, a bioreactor can include a lid and an associated support system which is configured to seal the fluidic well plate. The lid can include a micromechanical actuator and a force sensor to provide controllable deformation or load to tissue constructs in the well plate. The micromechanical actuator can be associated with and aligned on center with a well of the well plate. The lid can be used with a commercially available well plate with or without an insert situated in a well thereof. In some embodiments, the lid is clear and flex to allow visualization of the cells.

Some embodiments include a modular, microfluidic, multi-tissue, mechano-active 3D bioreactor. A bioreactor can include a microfluidic base, a bioreactor insert, and a mechano-activating lid assembly. In various embodiments, a base, insert, and lid assembly can be used in various combinations, sub-combinations, or individually. In some embodiments, a base permits direct or indirect interaction of two or more native or engineered tissue types while simultaneously providing separate fluid types to the various tissue types via microfluidic conduits which feed the tissue directly or via biological or physical intermediates within the geometry of standard multi-well plates.

A bioreactor can be amenable and adaptable to common tissue culture practices and devices (e.g., multi-channel pipettes, etc.) and high-throughput formats, depending on the scale of the wells. The insert can divide a single well into upper and lower compartments which do not communicate directly. They may interact indirectly only through the intervening tissue/construct disposed within an inner chamber. Two or more tissues in the inner chamber can interact with each other directly or indirectly while being exposed to two different environments. The dimensions of the inserts can be adapted to fit tissue culture containers of any size and shape. Tissues grown in a bioreactor can be exposed to mechano-activating or other damaging forces. A mechano-activating lid assembly can load and test tissue along a vertical axis while maintaining sterility of the system.

Some embodiments allow growth of an anatomic biphasic structure with a functional interface, and allow growth of each tissue type from a single cell source to eliminate possible age/tissue type incompatibility. Some embodiments include individual compartments to constitute separate microenvironments for the different tissue types, such as for the "synovial" and "osseous" components of a microtissue, each being independently accessible to allow introduction of bioactive agents or candidate effector cells. Some embodiments are compatible with the application of mechanical load and perturbation, as well as with imaging capability to allow for non-invasive functional monitoring.

The devices, systems, and methods described herein can be used to study bone-cartilage interaction to investigate OA, although their applicability is not so limited. The devices, systems, and methods disclosed herein can be used to study bone-cartilage interaction to investigate other biological processes or effects, or can be used to study the interaction between other types of tissues. Unless otherwise explained, all technical and scientific terms used herein have the same meaning as commonly understood by one of ordinary skill in the art to which this disclosure belongs.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adipose-Mediated Diabetic Complications on Knee Joint: Arthritis is seen in over 48% of diagnosed diabetic patients, and OA is 1.44 times more prevalent in diabetic adults compared to the general population. Local production of cytokines and adipokines by adipose tissues, and higher level of blood glucose and advanced glycation end products (AGEs) in diabetic patients are thought to play key roles in OA development. High glucose levels favor chondrocyte catabolism, while increased AGE levels are associated with a stiff collagen network, collagen damage, and proteoglycan release, and stimulate the production of MMP-1, 3, 13 and the pro-inflammatory factors TNF-α, PGE2, NO, and IL-6. The association between obesity and OA is significantly related to changes in the IPFP secretome. The IPFP has been shown to affect other joint tissues by secreting various factors, such as IL's, cytokines and adipokines. While macrophages and leukocytes in the adipose tissue are responsible for the release of most of the inflammatory mediators and contribute to the etiopathogenesis of OA (including by infiltrating into the synovial fluid), adipocytes are involved via secretion of adipokines, such as resistin, leptin, and adiponectin. Most adipokines also act as pro-inflammatory agents in joint diseases, suggesting their adverse influence on OA progression. Recent studies by the inventors show that treatment with IPFP-conditioned medium or isolated IPFP adipocytes accelerates degeneration of articular cartilage damaged by mechanical impact (36 MPa), and the degeneration is mediated most likely by IPFP-secreted IL-6. These findings are consistent with the hypothesis that the IPFP is an OA target joint tissue capable of modulating inflammatory and degenerative tissue responses. No therapies have been developed to treat diabetes/obesity complications related to OA.

Administration: The introduction of a composition into a subject by a chosen route. The route can be local or systemic. For example, if the chosen route is intravenous, the composition is administered by introducing the composition into a vein of the subject. If the chosen route is local, such as for treatment of fracture, the composition is administered by introducing the composition into the tissue gap in the fracture site.

Animal: Living multi-cellular vertebrate organisms, a category that includes, for example, mammals and birds. The term mammal includes both human and non-human mammals. Similarly, the term "subject" includes both human and veterinary subjects, for example, non-human primates, dogs, cats, horses, rabbits, pigs, mice, rats, and cows.

Articular Cartilage: A cartilage surface covering opposing joint surfaces that is clear, white and smooth in a normal joint. The function of the articular cartilage (AC) is mechanical, as the AC allows frictionless motion and absorbs and distributes loads. The calcified cartilage physically connects the AC to the subchondral bone, and underlying cortical and trabecular bone. The cartilage receives nutrients, cytokines, and hormones from bone in vivo, and vice versa, and healthy subchondral bone is essential for healthy cartilage. Studies of osteochondral tissue plugs cultured in vitro showed that bone tissue preserves chondrocyte survival. Abnormal stiffness of the subchondral bone causes cartilage overload that results in its mechanical breakdown, as seen in osteoarthritis. Osteoclastogenesis and subchondral bone loss was observed after cartilage damage, likely caused by chondrocyte-secreted factors within the degraded cartilage. The coordinated connection of AC and subchondral bone in normal and diseased situations suggests their close crosstalk and supports treating them as a functionally integral unit.

Bioreactor: Any manufactured or engineered device or system that supports a biologically active environment. In one embodiment, a bioreactor includes reactor chambers which are a set of vessels in which a chemical process is carried out which involves organisms or biochemically active substances derived from such organisms. The process can either be aerobic or anaerobic. A bioreactor may also include a device or system meant to grow cells or tissues in the context of cell culture for use in tissue engineering or biochemical engineering. On the basis of mode of operation, a bioreactor may be classified as batch, fed batch or continuous (e.g. a continuous stirred-tank reactor model). Cells growing in bioreactors may be submerged in liquid medium in suspension or may be attached to the surface of a solid medium. Suspension bioreactors can use a wider variety of organisms and cells, since special attachment surfaces are not needed, and can operate at much larger scale than immobilized cultures. However, in a continuously operated process the cells will be removed from the reactor with the effluent. Immobilization is a general term describing a wide variety of cell or particle attachment or entrapment. Immobilization is useful for continuously operated processes, since the cells will not be removed with the reactor effluent, but can be more limited in scale (for example, cell number) because the cells are only present on the surfaces of the vessel.

Bone: Hard tissue formed by endochondral ossification and intramembranous ossification. Endochondral ossification involves the formation of the growth plate, a spatially organized structure within which chondrocytes mature through oriented proliferation, hypertrophy, and eventually either apoptosis or differentiation into osteoblasts. Intramembranous ossification involves the direct conversion of mesenchymal progenitors to osteoblasts without the intervening chondrocyte maturation or growth plate structure, and involves the gradual fusion of clusters of osteoblasts known as spicules. Mature bone is composed of three types of cells: osteoblasts, osteocytes, and osteoclasts. Osteoclasts, responsible for bone resorption, are derived from hematopoietic stem cells. Osteoblasts, responsible for bone synthesis, are derived from Sox9+ mesenchymal progenitors that can differentiate into chondrocytes or preosteoblasts. Osteoblasts that become embedded within the bony matrix continue to differentiate into osteocytes. Osteocytes compose more than 90% of all mature bone cells and are involved in signaling to control calcium balance and bone remodeling in response to mechanical and hormonal cues via control of osteoblast and osteoclast differentiation. Osteoblastic cells lay down a calcified bony matrix composed primarily of type I collagen. Calcification requires the expression of alkaline phosphatase (Alpl) to provide the necessary phosphate for forming hydroxyapatite along with a host of matrix proteins that support the formation of calcified matrix including osteonectin, integrin binding sialoprotein (Ibsp), and osteopontin. Mammals are capable of complete and perfect regeneration of bone following fracture. The majority of fractures are healed by a combination of intramembranous and endochondral ossification. Following a fracture there is a brief inflammatory period after which periosteal and bone marrow mesenchymal precursors migrate to the site of fracture to initiate formation of a callus that is later remodeled to mature bone. Bone morphogenetic protein 2 (BMP-2) is integral to bone healing.

Bone defect: Includes any disease, defect, or disorder which affects bone strength, function, and/or integrity, such as those resulting from injury, or a defect brought about during the course of surgery, infection, malignancy, or developmental malformation. Examples of bone defects include, but are not limited to, fractures (such as a critical defect or non-union fracture), dental or facial defects (such as cleft palate or facial, skull, or dental injuries or malformations). Other examples of bone defects include damage to bones resulting from diseases of bone fragility, such as osteoporosis, and malignancies and/or cancers of the bone such as a sarcoma, such as osteosarcoma.

Bone disease: Includes any disease or disorder which affects bone strength, function, and/or integrity, such as decreasing bone tensile strength and modulus. Examples of bone diseases include, but are not limited to, diseases of bone fragility and genetic diseases which result in abnormal bone formation. Bone diseases include, but are not limited to, osteogenesis imperfecta, osteoporosis, or a metabolic bone disease. Other examples of bone diseases include malignancies and/or cancers of the bone such as a sarcoma, such as osteosarcoma.

Bone-forming cells and mineral forming cells: Cells having osteogenic potential. Examples include, but are not limited to: bone marrow stromal cells, adipose-derived stem cells, osteoblasts, osteocytes, and dental pulp cells. "Osteogenesis" is the formation or production of bone. "Osteogenic" cells are cells (such as osteocytes or their precursors) capable of forming or producing bone. The precursor cells may be cells that have entered committed developmental pathways to be osteocytes. The osteogenic cells may or may not be present in association with already formed bone.

Bone Healing and Fracture Healing: Bone heals (fuses) in a unique way compared with other connective tissues. Rather than develop scar tissue, it has the innate ability to regenerate itself completely. The majority of fractures heal by secondary fracture healing, that involves a combination of intramembranous and endochondral ossification. Without being bound by theory, it is generally believed that the fracture healing sequence involves five discrete stages of healing. This includes an initial stage in which a hematoma is formed and inflammation occurs; a subsequent stage in which cartilage begins to form and angiogenesis proceeds, and then three successive stages of cartilage calcification, cartilage resorption and bone deposition, and ultimately a more chronic stage of bone remodeling. Generally, committed osteoprogenitor cells and uncommitted, undifferentiated mesenchymal cells contribute to the process of fracture healing. Bone that forms by intramembranous ossification is found early and further from the site of the fracture, results in the formation of a hard callus, and forms bone directly without first forming cartilage. Generally, two weeks after fracture, cell proliferation declines and hypertrophic chondrocytes become the dominant cell type in the chondroid callus, and undergo further matrix mineralization, followed by infiltration of bone-forming cells. The resulting endochondral bone is formed adjacent to the fracture site.

Bromodeoxyuridine (BrdU) incorporation: Brdu is a synthetic nucleoside analog, 5-bromo-2'-deoxyuridine. BrdU is commonly used in the detection of proliferating cells in living tissues. BrdU can be incorporated into the newly synthesized DNA of replicating cells during the S phase of the cell cycle. BrdU substitutes for thymidine during DNA replication, and thus can be used as an indication of cells that were actively replicating their DNA.

Bone Morphogenetic Proteins (BMPs): A family of proteins, identified originally in extracts of demineralized bone that were capable of inducing bone formation at ectopic sites. BMPs are found in minute amounts in bone material (approximately 1 microgram/kg dry weight of bone). Most members of this family (with the exception of BMP-1) belong to the transforming growth factor-β family of proteins.

BMPs can be isolated from demineralized bones and osteosarcoma cells. They have been shown also to be expressed in a variety of epithelial and mesenchymal tissues in the embryo. BMPs are proteins which act to induce the differentiation of mesenchymal-type cells into chondrocytes and/or osteoblasts before initiating bone formation. They promote the differentiation of cartilage- and bone-forming cells near sites of fractures but also at ectopic locations. Some of the BMPs induce the synthesis of alkaline phosphatase and collagen in osteoblasts. Some BMPs act directly on osteoblasts and promote their maturation while at the same time suppressing myogenic differentiation. Other BMPs promote the conversion of mesenchymal cells into chondrocytes, and are also capable of inducing the expression of an osteoblast phenotype in non-osteogenic cell types. Among the BMPs, BMP-2 and BMP-4 and BMP-7 have been shown to promote bone formation. cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Cell Culture: The maintenance of cells in an artificial, in vitro environment that favors growth and survival. Suspension cell culture is a cell culture in which the majority or all of cells in a bioreactor, such as a culture vessel, are present in suspension (freely floating in liquid phase media), and the minority (or none) of the cells are attached to a surface. In several embodiments, a suspension culture has greater than 75%, 85%, or 95% of the cells in suspension, and thus not attached to a surface on or in the bioreactor.

The term "batch culture" refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified. The term "fed-batch culture" refers to a method of culturing cells, in a fed-batch bioreactor, in which additional components are provided to the culture at some defined time point(s) subsequent to the beginning of the culture process. The provided components typically comprise nutritional supplements for the cells that have been depleted during the culturing process. A fed-batch culture is typically stopped at some point and the cells and/or components in the medium are harvested and optionally purified. Media is not perfused into a fed-batch culture.

The term "perfusion culture" refers to a method of culturing cells in which additional fresh medium is provided, continuously at a defined rate over some period of time, to the culture, and simultaneously spent medium is removed. The fresh medium typically provides nutritional supplements for the cells that have been depleted during the culturing process. Protein product, which may be present in the spent medium, is optionally purified. Perfusion also allows for removal of cellular waste products (flushing) from the cell culture growing in the bioreactor. Implicit in this terminology is that cell are retained in the culture system and not allowed to be lost through the exit stream.

Chondrocyte: Cells found in cartilage that act to produce and maintain the cartilaginous matrix. Chondrocytes produce all of the structural components of cartilage, including collagen, proteoglycans and glycosaminoglycans. Chondrocytes can be found as individuals or in clusters called isogenic groups, which represent recently divided cells. "Chondrogenic" cells that are capable of forming chondrocytes or cartilage, such as cells that have entered a developmental pathway that has committed them to be chondrocytes. "Cartilaginous" tissue refers to tissue that is partially, completely or substantially made of cartilage.

Contacting: Placement in direct physical association. Includes both in solid and liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-$\alpha$, interleukin (IL)-6, IL-10, IL-12, transforming growth factor, and interferon-$\gamma$.

Disease modifying osteoarthritis drug (DMOD): A subset of a disease modifying drug (DMD) that can modify the status or progression of OA.

Expressed: The translation of a nucleic acid sequence into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Fibroblast Growth Factor (FGF): A large family of multigene family of growth factors that is a pleiotropic regulator of the proliferation, differentiation, migration, and survival in a variety of cell types. The proteins in this family are 16-18 kDa proteins controlling normal growth and differentiation of mesenchymal, epithelial, and neuroectodermal cell types. Two main groups of FGF are known. One type of FGF was isolated initially from brain tissue and identified by its ability to enhance proliferation of murine fibroblasts. Due to its basic pI the factor was named basic FGF or FGF-2. This factor is the prototype of the FGF family. Another factor, isolated also initially from brain tissues, has the ability to enhance proliferation of myoblasts. This factor is termed acidic FGF (aFGF). Other proteins in the FGF family are int-2 (FGF-3), FGF-4 FGF-5, FGF-6, K-FGF (FGF-7) and FGF-8. All of these factors are products of different genes. Some FGF are not secreted (FGF-2) while others (FGF-3, FGF-4, FGF-5 and FGF-6) have a signal sequence and therefore are secreted. Presently there are 23 factors identified as an FGF (numbered FGF-1 to FGF-23). Basic fibroblast growth factor ("b-FGF" or "FGF-2") is a potent stimulator of angiogenesis and hematopoiesis in vivo. FGF-2 is also involved in organogenesis, vascularization, and wound healing, and plays an important role in the differentiation and/or function of various organs, including the nervous system, and the skeleton. Because of its angiogenic and anabolic properties, FGF-2 has been shown to be involved in wound healing.

Fracture: A medical condition in which a bone is cracked or broken; a break in the continuity of a bone. Fractures may be classified as closed or open. A closed fracture is one in which the skin is intact; an open (or compound) fracture is one in which the bone is in contact with the air (such as piercing the skin or due to severe tissue injury). Fractures are also classified as simple or multi-fragmentary. A simple fracture occurs along only one line (such as splitting a bone into two pieces), while a multi-fragmentary fracture splits a bone into multiple pieces (such as three or more pieces). Other types of fracture include complete, incomplete, linear, transverse, oblique, compression, spiral, comminuted, and compacted fractures. Additional fractures include a critical defect (such as when part of a bone is lost or removed) and a non-union fracture (such as when the ends of the fracture are not in contact with each other).

Gel: refers to a solid, jelly-like material having a substantially dilute cross-linked structure exhibiting no flow when in the steady state. An example is a hydrogel.

Growth factor: A substance that promotes cell growth, survival, and/or differentiation. Growth factors include molecules that function as growth stimulators (mitogens), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (such as FGF-2), epidermal growth factor (EGF), cilliary neurotrophic factor (CNTF), and nerve growth factor (NGF), and actvin-A.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Hydrogel: A solid, jelly-like material having a controlled cross-linked structure exhibiting no flow when in the steady state.

Hypoxia: A condition of lower oxygen tension with respect to the oxygen tension of another tissue or fluid. For example, the oxygen tension of synovial fluid in humans is reported to normally be 6-9%. Atmospheric tension of oxygen is approximately 20%. Hence a fluid having an oxygen content lower than atmospheric is considered hypoxic with respect to atmosphere. The term "hypoxic" can also refer to relative oxygenation of different types of fluids in the body. A fluid, such as a fluid nutrient medium, can be made hypoxic with respect to another such medium, by adding an inert gas such as to the atmosphere in which a fluid is maintained.

Immune response: A response of a cell of the immune system, such as a B cell, T cell, neutrophil, macrophage or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Infrapatellar Fat Pad (IPFP): An anatomically intra-articular but extrasynovial adipose tissue. The IPFP contributes to the distribution of synovial fluid and force absorption in the joint, and damage by impingement results in a painful disease (Hoffa's Syndrome). The IPFP is highly vascularized and innervated with abundant adipocytes. The role of IPFP, long considered only as a cushion, was seldom considered in joint diseases. With the discovery of leptins, adipose endocrine functions and involvement in many physiologic and pathologic processes are now well recognized. Other major tissues also contribute to joint movement, including muscle, meniscus, intraarticular ligament, and their injuries are closely linked to onset of OA, most often resulting from abnormal mechanical loading that impacts cartilage and bone. Patients with knee OA typically present with reduced ability for full and voluntary muscle activation, but the underneath mechanism is still not clear.

Induced pluripotent stem cells (iPSCs): Cells generated by reprogramming 5 a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, 10 and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

Inhibiting or treating a disease: Inhibiting the full development of a disease or condition or accelerating healing, for example, in a subject who is at risk for a disease (for example, OA). "Treatment" refers to a therapeutic intervention that ameliorates a sign or symptom of a disease or pathological condition after it has begun to develop. Treatment can also refer to acceleration of fracture healing. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, such as pain, a shortened recovery time or an improvement in the overall health or well-being of the subject, or by other parameters well known in the art that are specific to the particular disease.

Isolated: An "isolated" biological component (such as a nucleic acid or protein or cell) has been substantially separated or purified away from other biological components in the cell of the organism, or other cells, in which the component naturally occurs. Nucleic acids and proteins that have been "isolated" include nucleic acids and proteins purified by standard purification methods. The term also embraces nucleic acids and proteins prepared by recombinant expression in a host cell as well as chemically synthesized nucleic acids. Similarly, isolated chondrocytes, osteocytes, adipocytes or macrophages refer to such cells that have been substantially separated or purified away from other biological tissue.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Mammal: This term includes both human and non-human mammals. Similarly, the term "subject" includes both human and veterinary subjects.

Matrix: Any material disposed between cells. A matrix can include any of various suitable biological or synthetic materials.

Mesenchymal Stem Cell (MSC): A multipotent stem cell capable of giving rise to differentiated cells in multiple mesenchymal lineages, specifically to osteoblasts, adipocytes, myoblasts, and chondrocytes. Generally, MSCs also have one or more of the following properties: an ability to undergo asynchronous, or asymmetric replication (where the two daughter cells after division can have different phenotypes); extensive self-renewal capacity; and clonal regeneration of the tissue in which they exist, for example, the non-hematopoietic cells of bone marrow. A cell can be classified as an MSC if it shows plastic adherent properties under normal culture conditions and has a fibroblast-like morphology, and can undergo osteogenic, adipogenic and chondrogenic differentiation ex-vivo.

MSCs can be cryopreserved. MSCs have been shown to engraft and selectively differentiate, based on the tissue environment. Due to their cellular origin and phenotype, these cells do not provoke an adverse immune response, allowing for the development of products derived from unrelated donors.

MicroJoint (mJoint) Bioreactor or Chip: A bioreactor that mimics physiological conditions in the osteochondral complex and has microscale bioreactor chambers. Specific examples include a device as described herein comprising microwells connected by microfluidic channels. In some embodiments, each well has planar dimensions inferior to those of single wells in a 96 well plate and a depth tailored to contain from about 1 al to about 10 al. Each bioreactor contains at least one, at least two, or multiple chambers, and one or more tissues fabricated as modules for easy connection to and disconnection from circulating flows.

Normoxia: Normoxic atmosphere conditions are typically characterized by oxygen tensions between 10 and 21%. Normoxia as applied to different bodily fluids refers to the normal oxygen content (for example oxygen tension or saturation) of that bodily fluid (such as synovial fluid or whole blood or blood serum).

Nutrient: A biological substrate, such as a chemical, vitamin, blood serum, salt, or yeast extract, that a cell requires to live, grow, and/or function, which must be or is advantageously taken from its environment. Examples of other types of nutrients are various carbohydrates, fats, proteins, amino acids, minerals, water, and oxygen.

Nutrient fluid: A liquid, such as a medium, that supplies nutrients to living cells, such as a culture medium or fluid. Some such media are specialized to support the growth of a particular type of tissue, such as cartilage (cartilage media) or bone (bone media) or the cells contained in such tissue. A nutrient fluid can also be a fluid that normally supplies nutrients (such as oxygen) to a biological tissue. An example is synovial fluid that bathes the synovium in a mammalian joint.

Osseous tissue: Tissue that contains bone, or is substantially or completely made of bone.

Osteoarthritis: Cartilage damaged by trauma, disease or aging demonstrates very limited capabilities for self-regeneration and ultimately results in OA. Severe OA ultimately require total joint arthroplasty, a major surgery that completely ends the biological life of joint tissues. During the onset and progress of OA, structural, biophysical, biochemical and biomechanical changes are observed in joint tissues. Physical stresses such as mechanical overloading or traumatic injury likely play key roles, by acting either directly on cartilage and chondrocytes, or affecting other components first, with secondary damage to cartilage. Genetic factors also play a role in disease susceptibility. In general, OA often starts with pathologic activation of resident chondrocytes, followed by production of pro-inflammatory factors and other degradative enzymes. Osteophytes in the subchondral bone appear before measurable articular cartilage thickness changes as well as related joint space narrowing, suggesting earlier pathogenic events. The development of disease-modifying medications (DMMs) has targeted the subchondral bone, including antiresorptives, bone-forming, or dual function anti-osteoporotic agents.

Current pharmacological management protocols, including use of non-steroidal anti-inflammatory drugs (NSAIDs), specific inhibitors of cyclooxygenase-2, and intra-articular injection of cortiocosteroids or hyaluronan, are focused only on pain relief and joint function improvement. However, the underlying structural damage of the joint is not restored by these treatments, and long-term usage of NSAIDs has been shown to be associated with serious side-effects. While available surgical interventions exist, such as microfracture and osteochondral grafting, they are limited by formation of inferior fibrocartilage and donor tissue site morbidity, respectively.

Osteoblast: A mononucleate cell that is responsible for bone formation. Osteoblasts produce an osteoid matrix, which is composed mainly of collagen type I. Osteoblasts are also responsible for mineralization of the osteoid matrix. Bone is a dynamic tissue that is constantly being reshaped by osteoblasts, which build bone, and osteoclasts, which resorb bone. Osteoblasts arise from osteoprogenitor cells located, for example, in the periosteum and the bone marrow. Osteoprogenitors are immature progenitor cells that express the master regulatory transcription factor Cbfa1/Runx2. Once osteoprogenitors start to differentiate into osteoblasts, they begin to express a range of markers including osterix, collagen type 1, alkaline phosphatase, osteocalcin, osteopontin, and osteonectin.

Osteoclast: A type of bone cell that removes bone tissue by removing its mineralized matrix by a process of bone resorption. Osteoclasts are formed by the fusion of cells of the monocyte-macrophage cell line. Osteoclasts are characterized by high expression of tartrate resistant acid phosphatase and cathepsin K.

Osteocyte: Mature, non-dividing bone cells that are housed in their own lacunae (small cavities in the bone). Osteocytes are derived from osteoblasts and they represent the final stage of maturation of the bone cell lineage. While osteocytes are metabolically less active than osteoblasts, they serve as the principal mechanosensing cells in bone, and are responsible for regulating the activity of bone-building osteoblasts and bone-resorbing osteoclasts in response to mechanical loading. The narrow, cytoplasmic processes of osteocytes remain attached to each other and to osteoblasts through canaliculi (small channels in the bone).

Osteoconduction: The scaffold function provided by the transplanted matrix biomaterial which facilitates cell attachment and migration, and therefore the distribution of a bone healing response throughout the grafted volume. This property is likely dependent on extracellular matrix molecules, such as those found in bone matrix, including collagens, fibronectin, vitronectin, osteonectin, osteopontin, osteocalcin, proteoglycans and others. Growth factors in the matrix may also play a role.

Osteomyelitis: Osteomyelitis is an infection in a bone. Infections can reach a bone by traveling through the bloodstream or spreading from nearby tissue. Osteomyelitis can also begin in the bone itself if an injury exposes the bone to germs.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Perfusion: In a bioreactor for the cultivation of mammalian cells, medium is perfused through the bioreactor at a specified rate while the cell mass is contained within the bioreactor by means of a cell retention device. In a suspension culture system, the cell retention device can be a filter, but numerous other methods can be employed, such as sonic separation, inclined plane settling, external centrifuges, internal filters such as spinning or oscillating, external hydrocyclones, etc. Fresh culture media is provided to the cells in the bioreactor. As the cell mass continues to grow and increase in number and mass, the rate of perfusion can be increased to remove metabolic byproducts and supply necessary nutrients.

Perfusion bio bioreactor: A bioreactor that includes a reactor chamber that has an inlet and outlet that provides for the provision of medium and the removal of waste or spent medium from the bioreactor at a specified flow rate. The medium is provided, and the waste is removed, at a specified continuous flow rate when the perfusion system is activated. The term also connotes that cells are retained or separated from the effluent (exit) stream and maintained to accumulate in the bioreactor. In a "Fed-batch bioreactor," there is a process of (a) adding nutrient media in bolus feeds to the bioreactor at designated time points, or (b) adding glucose (or another single nutrient) to the bioreactor as the glucose (or other single nutrient) is consumed at designated time point, without using a continuous flow. Thus, a fed-batch bioreactor is distinct from a perfusion bioreactor.

Perturbation: A disruption, such as in a culture. A perturbation can be chemical, mechanical or biological. A "perturbation" can be used to mimic a disease condition, such as OA.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pluripotent: The property of a cell to differentiate into all other cell types in an organism, with the exception of extraembryonic, or placental, cells. Pluripotent stem cells are capable of differentiating to cell types of all three germ layers (e.g., ectodermal, mesodermal, and endodermal cell types) even after prolonged culture.

Pluripotent stem cells: Stem cells that: (a) are capable of differentiating into teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc.), but that cannot form an embryo along with its extraembryonic membranes (are 15 not totipotent). Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). These embryonic stem cells can be generated from embryonic material produced by fertilization or by asexual means, including somatic cell nuclear transfer SCNT), parthenogenesis, and androgenesis. PSCs alone cannot develop into a fetal or adult animal when transplanted in utero because they lack the potential to contribute to all extraembryonic tissue (e.g., placenta in vivo or trophoblast in vitro). Pluripotent stem cells include iPSC generated by reprogramming a somatic cell by expressing or inducing expression of a combination of factors (herein referred to as reprogramming factors).

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (for example, a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). A "residue" refers to an amino acid or amino acid mimetic incorporated in a polypeptide by an amide bond or amide bond mimetic, the "position" of the residue indicates its place in the amino acid sequence. A polypeptide has an amino terminal (N-terminal) end and a carboxy terminal end.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987). Specific, non-limiting examples of promoters include promoters derived from the genome of mammalian cells (for example, a metallothionein promoter) or from mammalian viruses (for example, the retrovirus long terminal repeat; the adenovirus late promoter; the vaccinia virus 7.5K promoter). Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Scaffold: A tissue support such as synthetic scaffolds, for example polymer scaffolds and non-synthetic scaffolds, for example pre-formed extracellular matrix or a de-cellularized organ scaffold. A scaffold can be in a particular shape or form so as to influence or delimit a three-dimensional shape or form assumed by a population of proliferating cells. This term also refers to any type of pre-formed scaffold that is integral to the physical structure of the engineered tissue and cannot be removed from the tissue without damage/destruction of said tissue. In some examples the scaffold is a thin three-dimensional substrate having opposite faces that can be separately bio-printed or seeded with cells. For example, the opposite surfaces may be parallel to one another and the outline of the scaffold as viewed from above may be any shape, such as circular, elliptical, oval, or polygonal (for example a rectangle, such as a square). The term "scaffold-less," therefore, is intended to imply that pre-formed scaffold is not an integral part of the engineered tissue at the time of use, either having been removed or remaining as an inert component of the engineered tissue. "Scaffold-less" is used interchangeably with "scaffold-free" and "free of pre-formed scaffold."

Stem cell: A cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs".

Subject: an animal or human subjected to a treatment, observation or experiment.

Synovial knee joint: A multi-component organ that plays essential roles in withstanding body loads and providing a mechanism for movement. In a healthy knee joint, smooth cartilage caps the end of hard subchondral bones, allowing for frictionless movement. The femoral and tibial ends are housed in a synovial fluid-filled joint cavity lined by the synovium. Ligaments, meniscus, muscles, and infrapatellar fat pad (IPFP) further stabilize the whole joint.

Synovium: A specialized connective tissue that serves as the joint lining capsule. A healthy synovium consists of a thin intimal lining layer of fibroblast- and macrophage-like synoviocytes (FSs and MSs) and macrophages, and a sub-lining layer of loose connective tissue. MSs are able to remove wear-and-tear tissue debris, and FSs produce large amount of hyaluronan and other matrix proteins, which together maintain the health of the synovial fluid. Under certain conditions, such as infection and over exposure to tissue debris, the synovium can become irritated and thickened (synovitis), accompanied by increased macrophage recruitment and invasion of other inflammatory cells. Consequently, the normal function of the joint is compromised, such as pain and reduced mobility.

Tissue: An aggregation of one or more types of specialized cells united in the performance of a particular function. Organs are formed by the functional groupings of multiple component tissues, hence the tissue may be different types of cells from a particular organ, such as bone. Different tissues can be divided into different categories in several ways, such as based on the embryonic origin of the tissue from ectoderm, mesoderm, or endoderm. Alternatively, the tissue may be a subunit of a physiological system, for example, bone and cartilage in the skeletal system, or an organ, such as dermis and epidermis in the skin, parenchyma and capsule in the liver, sinusoids and parenchyma in the liver, intestinal epithelium and underlying mucosa in the intestine, neurons and myelin in a peripheral nerve, corneal endothelium and epithelium in the eye, renal cortex and medulla in the kidney, and a variety of other distinct but anatomically adjacent tissues that may be found in the body. However, the different tissue types are not confined to normal anatomic tissues but can also include different types of specialized cells found in pathological conditions, such as tumor and adjacent non-tumor tissue of the same or different type, such as adenocarcinoma of the breast and adjacent normal (non-malignant) breast tissue. Tissues that are in "functional contact" with each other need not be in physical contact, but can be separated by an intermediate layer that mediates biochemical communication between the tissues. For example, a layer of mesenchymal stem cells between a layer of chondrocytes and osteoblasts can physically separate them but still permit biochemical communication between the chondrocyte and osteoblast layers. Engineered tissue constructs which properly incorporate plural tissue layers into an interactive microtissue unit can help in accurately studying biological tissues and their interactions, and can help in elucidating the pathogenesis of various diseases and assessing the efficacy of potential therapeutics against those diseases. Some of the devices, systems, and methods described herein facilitate the growth of physiologically accurate microsystems having distinct biological tissue layers, such as those found within an organ (e.g., the liver) or other physiological system (e.g., the skeletal system). Portions of the current disclosure refer to the osteochondral complex and OA, which are of particular interest herein, although the devices, systems, and methods disclosed should be understood to be applicable to multi-tissue cultures generally.

Tissue Culture Medium or Medium: A synthetic set of culture conditions with the nutrients necessary to support the growth (cell proliferation/expansion) and survival of a specific population of cells. Tissue culture media generally include a carbon source, a nitrogen source and a buffer to maintain pH. In one embodiment, a medium contains a minimal essential media, such as DMEM, supplemented with various nutrients to enhance stem cell growth. Additionally, the minimal essential media may be supplemented with additives such as horse, calf or fetal bovine serum. A "chemically defined" cell culture medium is one in which each chemical species and its respective quantity is known prior to its use in culturing cells. A chemically defined cell culture medium is made without lysates or hydrolysates whose chemical species are not known and/or quantified. The terms "serum-free culture conditions" and "serum-free conditions" refer to cell culture conditions that exclude serum of any type. These terms can be used interchangeably.

Treatment: includes therapeutic measures that cure, slow down, lessen symptoms of, and/or halt progression of a diagnosed pathologic condition or disorder.

Therapeutically effective amount: A quantity of a specific substance, such as a stem cell, for example MSCs, sufficient to achieve a desired effect in a subject being treated. For instance, this can be the amount necessary to accelerate fracture healing. When administered to a subject, a dosage will generally be used that will achieve target tissue concentrations (for example, in bone) that has been shown to achieve a desired in vitro effect.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. Vectors can be viral vectors, such as adenoviral, retroviral, or lentiviral vectors. Vectors can be non-viral vectors, such as Sleeping Beauty plasmids or Prince Charming plasmids.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. The term "about" indicates a variation of 5 percent or less. In case of conflict, the present specification, including explanations of terms, will control. In addition, the materials, methods, and examples are illustrative only and not intended to be limiting.

Bioreactor Reactor Chambers

Reactor chambers that can be used in the disclosed bioreactors are disclosed below. See also PCT Publication No. WO 2017/062629 and PCT Publication No. WO 2015/027186, both incorporated herein by reference.

FIG. 1 shows a cross-sectional view of an exemplary bioreactor reactor chamber 100. Bioreactor reactor chamber 100 includes a shell 102 having a generally cylindrical inner space, as well as an upper inlet 104, lower inlet 106, upper outlet 108, and lower outlet 110. The shell 102 has a closed bottom end 112 and an open top end 114. Several components are situated within the shell 102 in order to facilitate desirable cellular growth therein. For example, the shell 102 encloses an inner body 116 which has a hollow interior 120 and includes a central protruding ring 118 having an outer diameter approximating the inner diameter of the shell 102. The inner body 116 also includes a lower porous screen 124, such as having lateral perforations, and an upper porous screen 126, such as having lateral perforations, each of which can have an outside diameter which is smaller than the inside diameter of the shell 102. Together, the protruding ring 118 and porous screens 124, 126 divide the interior of the shell 102 into an inner lower chamber 128, an outer lower chamber 130, an inner upper chamber 132, and an outer upper chamber 134. Fluids can flow laterally through the upper porous screen 126 between the inner upper chamber 132 and the outer upper chamber 134, and fluids can flow laterally through the lower porous screen 124 between the inner lower chamber 128 and the outer lower chamber 130.

As shown in FIG. 1, the bioreactor reactor chamber 100 can further include an upper ring 136 and a piston 138. The piston 138 can be used to impart a compressive force on materials situated within the bioreactor reactor chamber 100, and the upper ring 136 can form a sealing element between the piston 138 and the shell 102. The upper ring 136 seals the open top end 114 of the bioreactor reactor chamber 100 while allowing the piston 138 to move into and out of the shell 102. Various substances (e.g., nutrients) can flow into the bioreactor reactor chamber 100 through the inlets 104, 106, around or through the inner body 116, and out of the bioreactor reactor chamber 100 through the outlets 108, 110.

Some of the substances entering the bioreactor reactor chamber 100 through inlet 104, for example, can flow around the upper porous screen 126 and out the outlet 108. Some of the media entering the bioreactor reactor chamber 100 through inlet 104 (the amount depending on the characteristics of the components of the system) can also flow laterally through the upper porous screen 126, through cellular tissues growing inside the inner body 116, flow laterally through the opposing side of the upper porous screen 126, and out through outlet 108. Finally, some of the media entering the bioreactor reactor chamber 100 through inlet 104 (again, the amount depending on the characteristics of the components of the system) can also flow through the upper porous screen 126, through cellular tissues growing inside the inner body 116, through the lower porous screen 124, and out through outlet 110. Corresponding flow paths are available for media entering the bioreactor through inlet 106.

This design allows for the provision of different fluids, compounds, and nutrients (e.g., a tissue culture medium or nutrient broth such as serum, or various other growth factors, steroids, growth hormones, etc.), or different concentrations of such materials, to the upper and lower chambers, and thus to different biological tissue layers disposed within the bioreactor reactor chamber 100. In some cases, the specific fluids and nutrients used can be tailored to the particular cell types grown in the bioreactor reactor chamber, as discussed below. For example, in bioreactor reactor chamber 100, hypoxic fluids can be fed through the upper chamber while normoxic fluids are fed through the lower chamber.

FIG. 1 shows that cellular material can be grown in at least 5 separate regions within the bioreactor reactor chamber 100. As shown, an osteoblast construct 140 can grow in the inner lower chamber 128, a mesenchymal construct 142 can grow on top of the osteoblast construct 140, and a chondrocyte construct 144 can grow on top of the mesenchymal construct 142. The chondrocyte construct 144 can be exposed to the piston 138 or a layer of synovial fluid can separate the chondrocyte construct 144 from the piston 138, and in either case, the piston 138 can be actuated to impart forces through the chondrocyte construct 144, the mesenchymal construct 142, and the osteoblast construct 140 to the bottom end 112 of the shell 102. Further, a layer of endothelial cells 146 can grow on the exterior of the lower porous screen 124, and a layer of human fibroblast cells 148 can grow on the exterior of the upper porous screen 126.

FIG. 2 shows a cross sectional plan view of the bioreactor reactor chamber 100 and its location within an exemplary array 200 of ninety six bioreactor reactor chambers 100.

FIG. 2 shows that plural bioreactor reactor chambers 100 can be arranged in an array 200 such that the outlets of some bioreactor reactor chambers are fluidly coupled to the inlets of other bioreactor reactor chambers. For example, the outlets 108, 110 of bioreactor reactor chamber 100a are coupled to the inlets 104, 106 of bioreactor reactor chamber 100b, respectively, and the outlets 108, 110 of bioreactor reactor chamber 100b are coupled to the inlets 104, 106 of bioreactor reactor chamber 100c, respectively. Thus, a plurality of bioreactor reactor chambers 100 can be coupled in series to facilitate distribution of substances through them. Additionally, a plurality of series 202 of multiple bioreactor reactor chambers 100 can be arranged adjacent one another to form an array 200. The plurality of series 202 can be fluidly coupled either in series or in parallel with one another. Specific configurations of reactor chambers, to form a complete bioreactor, are presented below.

FIG. 3 shows an exemplary shell 300, exemplary inner body 302, and an exemplary upper ring 304. The shell 300 has an overall hollow cylindrical shape, and comprises an upper inlet 306, a lower inlet 308, an upper outlet 310, and a lower outlet 312, each of which comprises a hollow, generally cylindrical extension extending radially outwardly from the shell 300. The shell 300 also includes a hollow, generally cylindrical inner space 314 within which the inner body 302, upper ring 304, and cellular material can be situated. The inner body 302 includes a lower porous screen 318 and an upper porous screen 316, both of which include a plurality of pores, or small openings, 326. The inner body 302 also includes a protruding ring 320 which protrudes radially outwardly from the rest of the inner body 302, and which has an outside diameter approximating the inner diameter of the inner space 314. Thus, when the inner body 302 is situated within the shell 300, several distinct chambers can be formed, as described above with regard to bioreactor reactor chamber 100.

FIG. 3 also shows that upper ring 304 has a groove 324 extending around the circumference of the inner surface of one end of the upper ring 304. The upper ring also has a main inner surface 328 having a generally cylindrical shape and an inner diameter approximating an inner diameter of the inner cylindrical space 330 in the inner body 302.

FIG. 4 shows the exemplary shell 300, inner body 302, upper ring 304, chondrocyte construct 144, and osteoblast construct 140, aligned along axis 332 in an exploded view. These elements can be combined, together with a mesenchymal construct (not shown in this figure) to form a bioreactor reactor chamber similar to bioreactor reactor chamber 100. When these components are assembled to form a bioreactor reactor chamber in this manner, the osteoblast construct 140, mesenchymal construct, and chondrocyte construct 144 are situated within the inner space 330 within the inner body 302. Further, a top end portion 322 of the inner body 302 can be situated within the groove 324 of the upper ring 304 to facilitate sealing of the system (note a similar structural configuration in FIG. 1—a top end of the upper porous screen 126 is situated within a similar groove at the bottom end portion of the upper sealing ring 136).

Figure 5A:
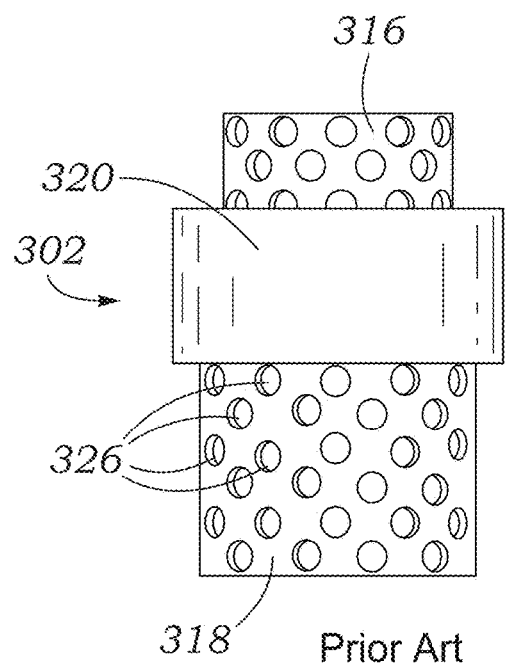
FIGS. 5A-5B show three-dimensional renderings of exemplary inner bodies for use in bioreactor systems, from two different views.
Figure 5B:
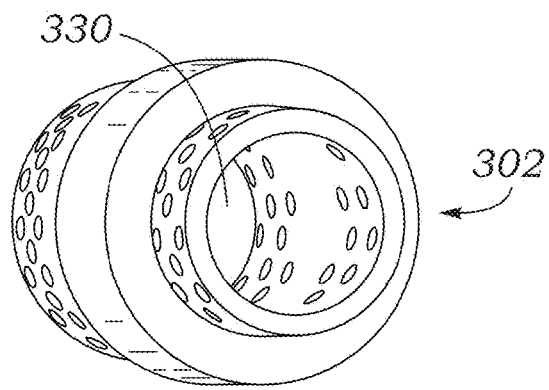
Figure 5C:
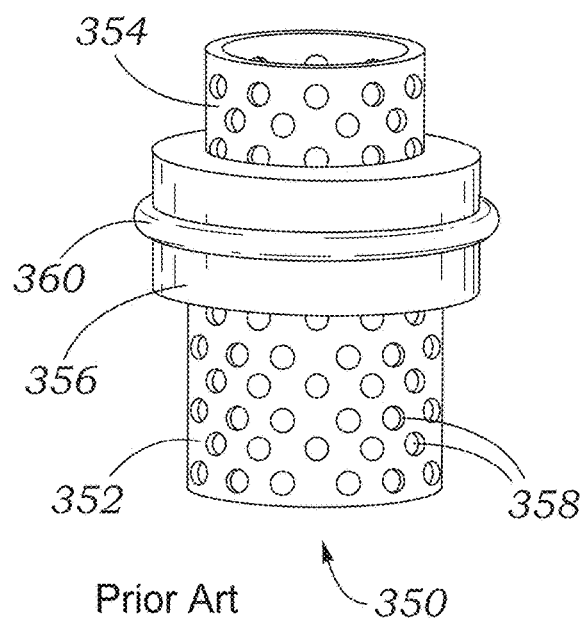
FIGS. 5C-5D show photographs of exemplary inner bodies for use in bioreactor systems, from two different views.
Figure 5D:
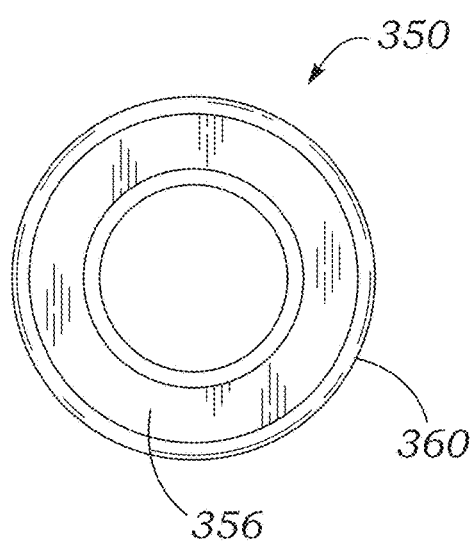

FIGS. 5A-5B show alternate views of the inner body 302 shown in FIGS. 3-4. FIG. 5B shows that the inner body 302 has a cylindrical inner open space 330 which spans through the entire body 302 to accommodate the positioning of cellular material therein. FIGS. 5C-5D illustrate an inner body 350 comprising a lower porous screen 352, an upper porous screen 354, and a protruding ring 356. The lower and upper porous screens have a plurality of pores 358. The inner body 350 also includes a sealing o-ring 360 disposed around the outside of the central protruding ring 356. The o-ring 360 helps seal the inner body 350 against the inner surface of a shell (e.g., shell 102) to more effectively maintain distinct chambers within the shell. The inner body 350 can be fabricated, for example, photolithographically using a biocompatible plastic-polymer. In some embodiments, the shell, body and/or ring of an inner body, or other parts of a bioreactor reactor chamber, can be fabricated with commercially available E-SHELL 300™ polymer resin using photo-stereolithography (PSL).

FIG. 5E is a schematic representation of a multiwell, dual chamber bioreactor system, with a 96 well bioreactor platform 362 shown at the lower right, and a cross-sectional view of a single bioreactor reactor chamber shown at the upper left. The multi-well platform 362 includes a plurality or rows of eight wells 370 that are in fluid communication from one inlet/outlet pair 364 across the row of wells 370 to an opposite inlet/outlet pair 366. Each well 370 is configured to receive a bioreactor reactor chamber insert 372 and a sealing lid 374 (the lid can be replaced with and/or incorporated into a mechanical actuator or piston that applies a mechanical loading pattern downward on the tissue/fluid in the bioreactor). The insert 372 is sealingly engaged with the inner surfaces of the well 370 via an o-ring 376 to form separate upper and lower fluid flow chambers. The lid 374 is also sealingly engaged with the inner surfaces of the well 370 via another o-ring 378 to prevent fluid escaping from the well. The insert 372 can contain at least two layers of biological material, such an upper layer 380 and a lower layer 382 as shown. The upper layer 380 can comprise a chondral construct and/or the lower layer 382 can comprise a osseous construct, for example. One or more additional layers, such as an intermediate layer, can also be included. An intermediate mesenchymal layer can be included, for example. Each well has two opposing upper inlet/outlets 384 and 388, which allow a first fluid to flow through the upper chamber to interact with the upper layer 380, and two opposing lower inlets/outlets 386, 390, which allow a second fluid to flow through the lower chamber to interact with the lower layer 382. The first fluid can comprise a chondrogenic medium and/or the second fluid can comprise an osteogenic medium, for example.

As illustrated in FIG. 5E, the first fluid can enter at 384 and then pass laterally through perforations in the insert 372 to enter the upper layer 380 laterally. The first fluid can then exit the upper layer 380 laterally through the perforations in the insert 372 before exiting the bioreactor at 388. The perforations can extend circumferentially around the insert 372 such that the first fluid can flow around the upper layer and can interact laterally with the upper layer from all lateral sides. Some of the first fluid can also flow over the top of the upper layer and perfuse into and out of the upper layer from its upper surface. Similarly, the second fluid can enter at 386 and then pass laterally through perforations in the lower portion of insert 372 to enter the lower layer 382 laterally. The second fluid can then exit the lower layer 382 laterally through the perforations in the insert 372 before exiting the bioreactor at 390. The perforations can extend circumferentially around the lower portion of the insert 372 such that the second fluid can flow around the lower layer and can interact laterally with the lower layer from all lateral sides.

Figure 6A:
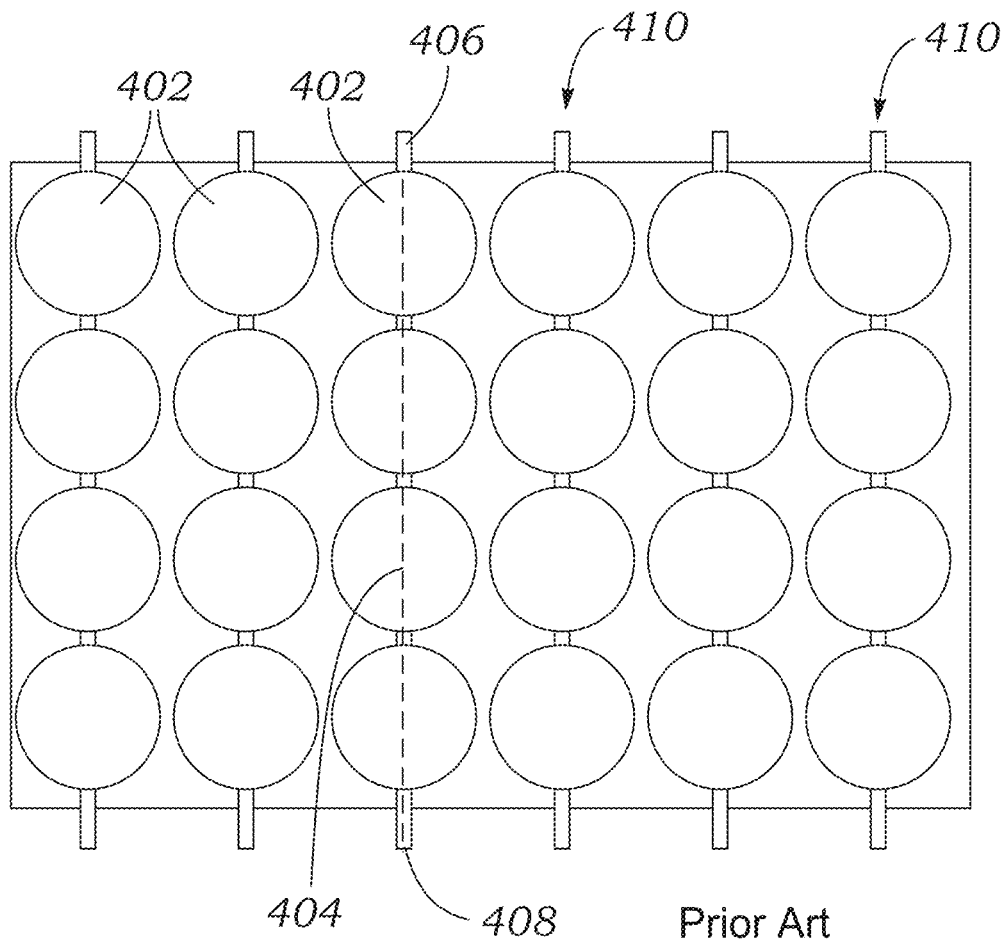
FIG. 6A shows a schematic plan view of an exemplary well plate having an array of wells therein, within each of which a bioreactor inner body can be situated, as well as a plurality of flow paths through the well plate.

FIG. 6A illustrates in plan view an exemplary array 400 of wells 402, within each of which an insert such as insert 350 can be situated. The array 400 of wells 402 includes six sets 410 of four wells 402 fluidly coupled in series. Thus, a flow path through four wells 402 is illustrated as conduit path 404, along which fluids can flow either from a first end 406 to a second end 408 or from the second end 408 to the first end 406. Thus, the first end 406 can be either an inlet or and outlet, and the second end 408 can be either an inlet or an outlet, depending on the direction of flow along the conduit path 404.

Figure 6B:
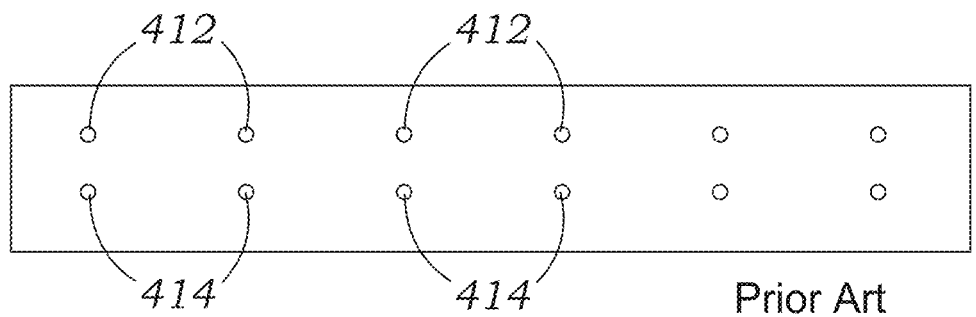
FIG. 6B shows a schematic side view of the well plate of FIG. 6A, including a plurality of upper ports and a plurality of lower ports.

FIG. 6B illustrates the array 400 from a side view, showing that each set 410 of wells 402 can have both an upper port 412 and a lower port 414 for carrying fluids into or out of the set 410 of wells 402, depending on the direction of flow along the conduit path 404.

FIG. 7 shows an array 450 of wells 452 similar to the array 400, with twenty-four wells 452 each having an integrated well insert. The wells 452 are arranged in six sets 454 of four wells 452 fluidly coupled in series. Each of the six sets of wells 452 is provided with a port 456 at each end, through which fluid can either enter or exit, depending on the flow path through the set 454 of wells 452.

In some embodiments, systems capable of mechanically stressing the cellular material grown in a bioreactor are desirable. Natural bone and cartilage growth is known to be affected by mechanical stresses encountered by those tissues as they grow, thus systems allowing the introduction of such stresses can facilitate tissue growth which more accurately resembles native tissue growth. Accordingly, FIGS. 8-11 illustrate several systems capable of mechanically stressing tissues as they grow in a bioreactor reactor chamber such as the bioreactor reactor chamber 100 described above.

Figure 8A:
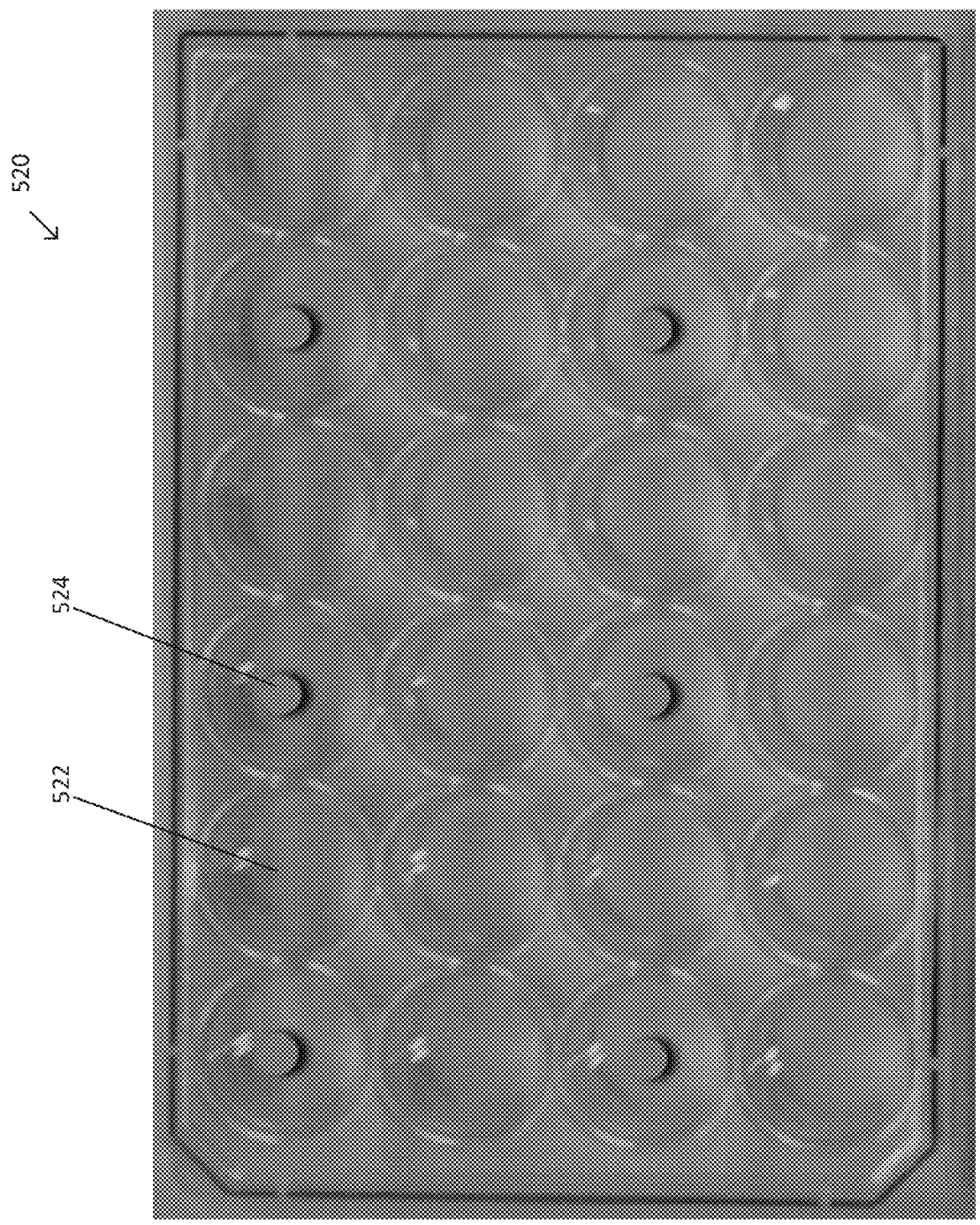
FIG. 8A illustrates an exemplary method of imparting an array of bioreactors with loading forces in groups of six at a time.
Figure 8B:
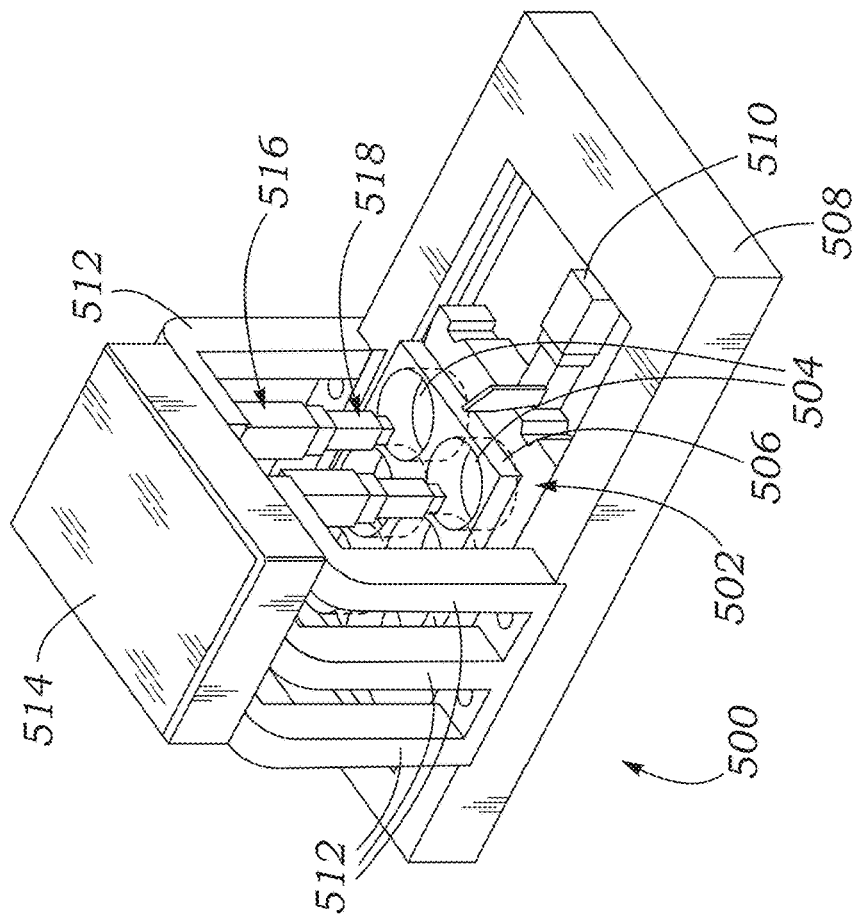
FIG. 8B shows a schematic drawing of an exemplary system having a plurality of mechanical actuators capable of mechanically stressing tissues within bioreactors or laboratory plates.

FIG. 8B shows an exemplary system 500 comprising an array 502 of six bioreactor reactor chambers 504, which can have various configurations but in one specific embodiment can be similar to the bioreactor reactor chamber 100. The array 502 can be situated on a mount 506 which can be horizontally slidable relative to a base plate 508. The mount 506 can be actuated to move horizontally relative to the base plate 508 using a sliding actuator 510. The system 500 also includes a set of vertical extension arms 512 rigidly coupled to the base plate 508, and an actuator housing 514 rigidly coupled to the extension arms 512. The actuator housing 514 houses six micromechanical actuators 516, which can be used to impart forces to the bioreactors 504. The actuators 516 can also include force sensors 518 to monitor the force being imparted to ensure that sufficient, but not excessive, force is imparted to the bioreactors 504 and the tissues grown therein.

The system 500 can be modified to allow the six actuators 516 to mechanically stress more than six bioreactor reactor chambers 504. For example, additional bioreactors 504 can be situated on the mount 506 and can be moved under the actuators 516 by action of the sliding actuator 510. Thus, the actuators 516 can be used to sequentially stress tissues in a larger number of bioreactors. In other embodiments, a second sliding actuator can be used to make the mount 506 slidable along two perpendicular axes. Thus, the actuators 116 can be used to induce stresses in tissues in bioreactors of an array having a larger number of bioreactor reactor chambers 504 in two dimensions.

FIG. 8A illustrates an exemplary method in which a multi-well tray of bioreactors can be sequentially stressed with loading forces in groups. For example, the tray 520 contains 24 bioreactor reactor chambers in a 4-by-6 array of wells 522. A mechanical loading apparatus, similar to that described in FIG. 8B, can apply loading forces to groups of six of the bioreactor reactor chambers at a time. An exemplary group of six is represented by the six dots 524. After providing loading forces on the group of six represented by the dots 524, the tray 520 and/or the loading mechanism can be shifted such that a different group of six wells 522 and bioreactor reactor chambers is positioned below the six loading members of the loading mechanism. This can be repeated until all 24 bioreactor reactor chambers are imparted with loading forces. In this way, the total of 24 bioreactor reactor chambers can be imparted with loads in four sessions, with six bioreactor reactor chambers being imparted with loading forces in each of the four sessions. FIG. 8A illustrates just one exemplary loading pattern. In other loading patterns, groups of different numbers and/or arrangements of bioreactor reactor chambers can be included in each loading session.

Figure 9:
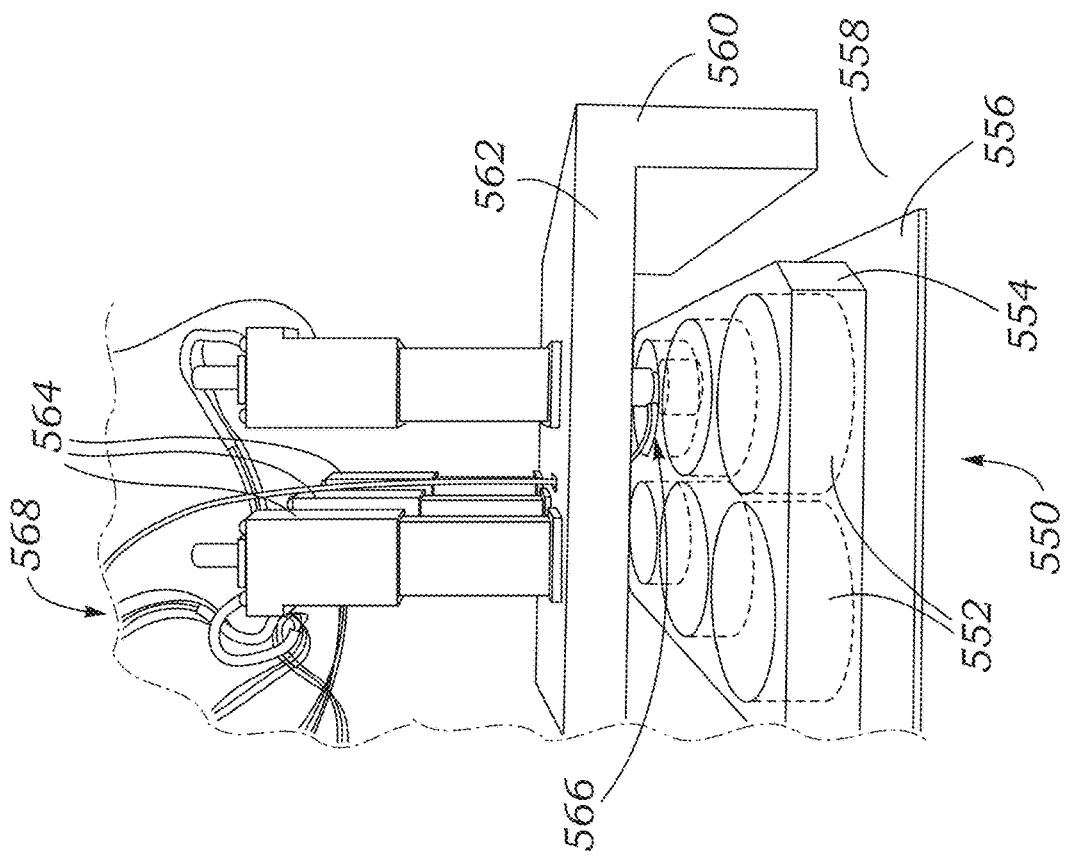
FIG. 9 shows a photograph of another exemplary system having a plurality of mechanical actuators capable of mechanically activating/stressing tissues grown in bioreactors and measuring their mechanical properties.

FIG. 9 shows a side view of an exemplary system 550 comprising six bioreactor reactor chambers 552 housed in a container 554, the container 554 situated on a tray 556 resting on a rigid surface 558. FIG. 9 also shows that supports 560, resting on the rigid surface 558, support an actuator support platform 562, on which six micromechanical actuators 564 are mounted. As in system 500, system 550 can be used to mechanically stress tissues grown in the six bioreactor reactor chambers 552 situated below the actuators 564. As in system 500, force sensors 566 can be coupled to the actuators 564 to measure the forces imparted by the actuators, to ensure sufficient, but not excessive, force is imparted to the tissues in the bioreactor reactor chambers 552. Wiring 568 can be used to couple the actuators to a controller unit such as a computer (not shown). The controller unit can be used to control the forces exerted by the actuators and to monitor force readings from the force sensors 566.

Figure 10:
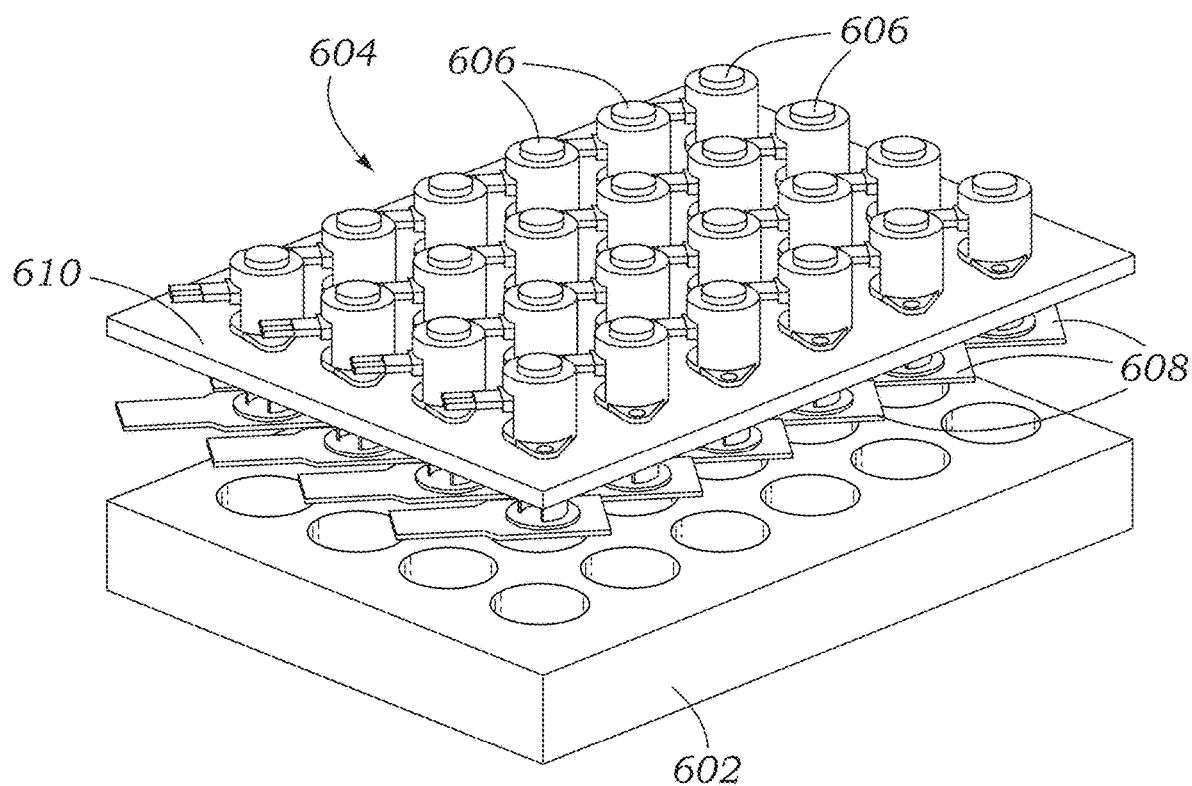
FIG. 10 shows a schematic drawing of another exemplary system having a plurality of mechanical actuators capable of mechanically activating/stressing tissues within laboratory multiwell plates and measuring their mechanical properties.

FIG. 10 shows another exemplary system 600 including a twenty-four well plate 602 and a mechanical stimulator lid assembly 604. The well plate 602 comprises twenty four wells, within each of which a bioreactor reactor chamber (e.g., bioreactor reactor chamber 100) can be situated. An inner body (e.g., an inner body similar to inner body 116) having a protruding ring and being configured to be situated within a well of the well plate 602 can have at least one vertical channel formed in its protruding ring, which channel can be configured to accommodate a pipe or tube which can carry fluid from the lower chamber of a first bioreactor reactor chamber, over the wall between adjacent wells of the well plate 602, and to the lower chamber of a second bioreactor reactor chamber adjacent to the first bioreactor reactor chamber. The mechanical stimulator lid assembly 604 comprises twenty-four micromechanical actuators 606 and twenty-four respective force sensors 608 with associated pistons. The actuators 606 and the sensors 608 are mounted on a support plate 610. As in previous embodiments, the actuators 606 can be used to mechanically stress tissue growing in bioreactor reactor chambers situated in the wells of the well plate 602.

Figure 11:
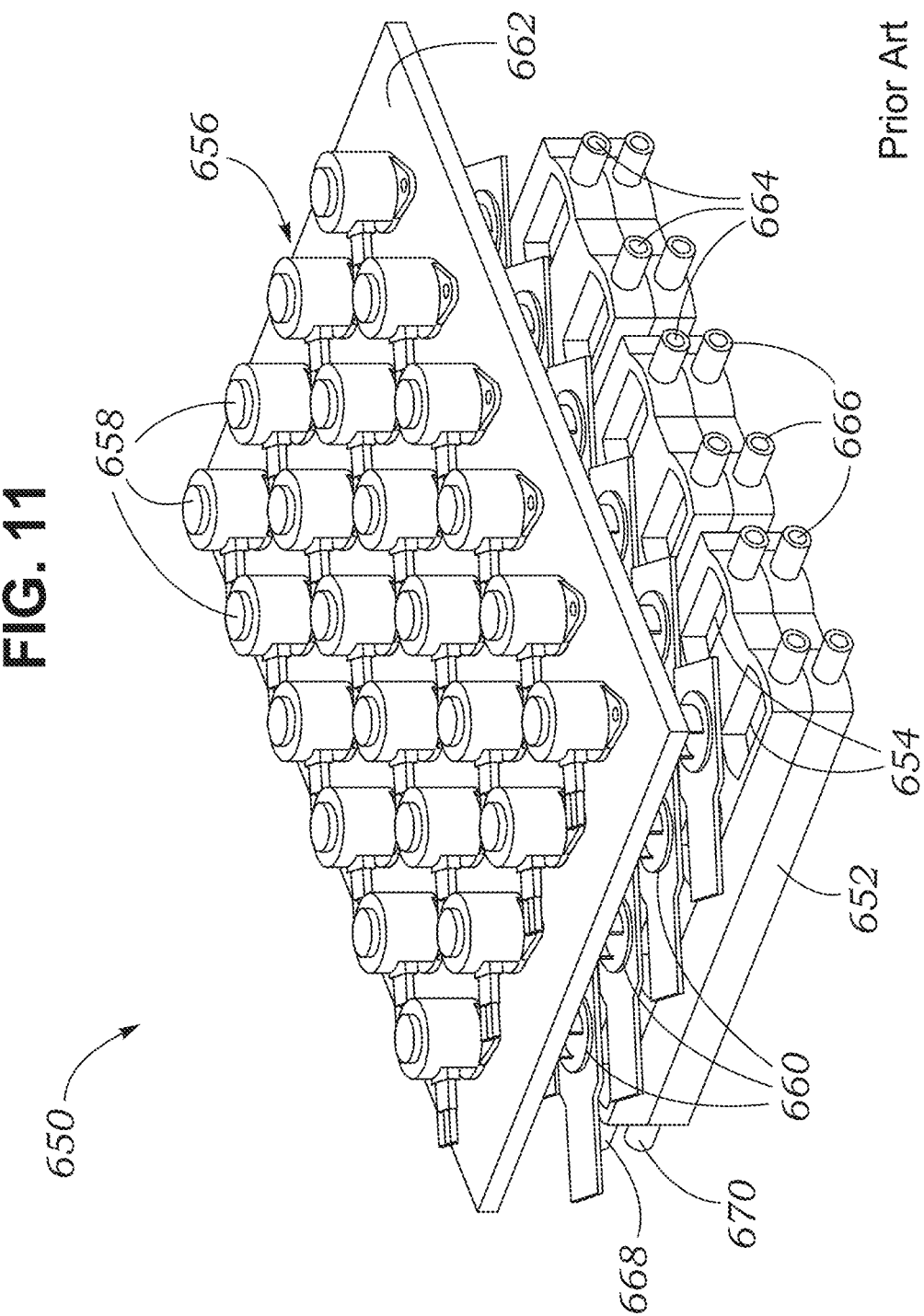
FIG. 11 shows a schematic drawing of another exemplary system having a plurality of mechanical actuators capable of mechanically activating/stressing tissues within bioreactors and measuring their mechanical properties.
Figure 14:
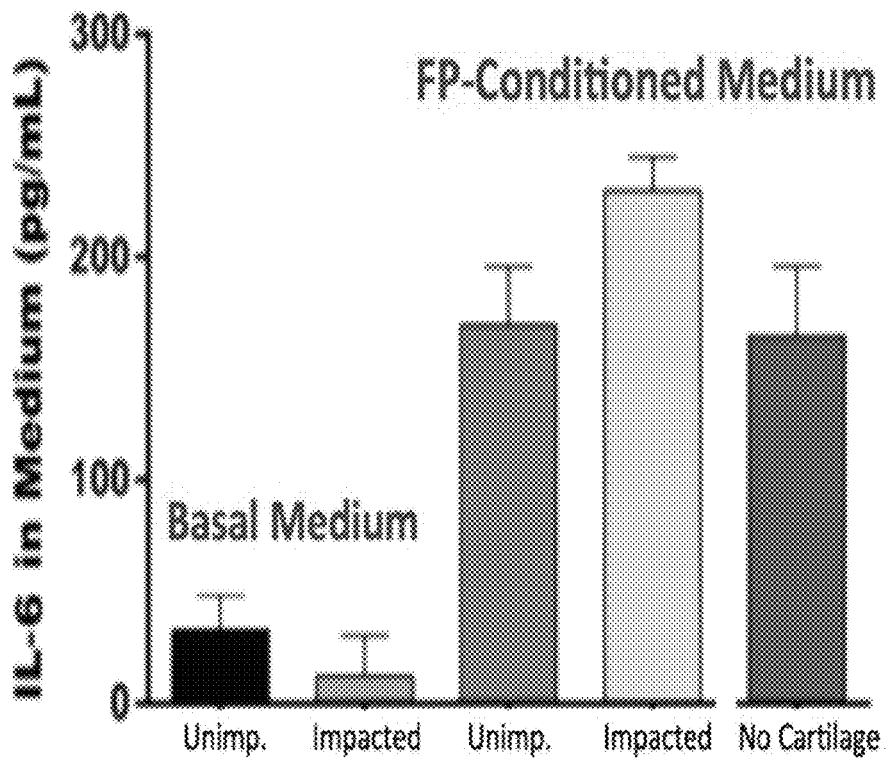
FIG. 14 shows that IPFP conditioned medium has elevated levels of IL-6.
Figure 15:
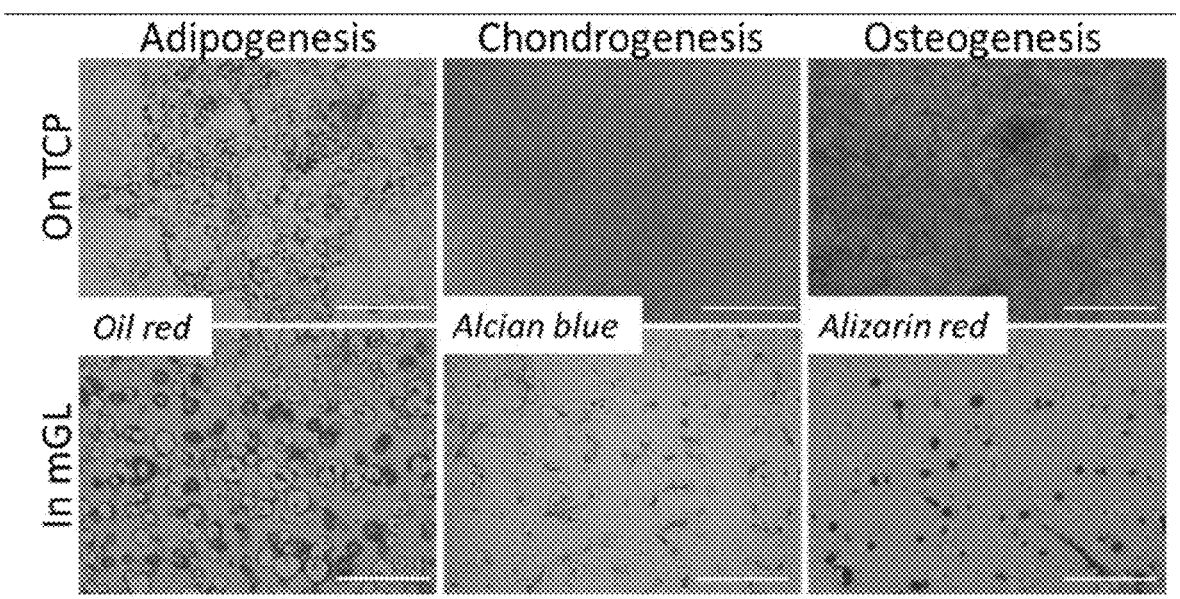
FIG. 15 shows that mesenchymal stem cells derived from induced pluripotent stem cells present robust adipo-, chondro- and osteogenesis on tissue culture plastic (TCP) and in gelatin (mGL) scaffolds. Bar=100 am.

FIG. 11 shows another exemplary system 650 similar to system 600. System 650 includes a twenty four well plate 652 comprising twenty-four wells 654, and a mechanical stimulator lid assembly 656 comprising twenty four micromechanical actuators 658 and twenty-four force sensors 660 mounted on a support plate 662. Additionally, FIG. 11 shows upper inlets 664, lower inlets 666, upper outlet 668, and lower outlet 670.

A type of bioreactor reactor chamber is shown in FIG. 13A. This system has an upper part and a lower part. There is an inlet for supplying a first medium to the upper part, an outlet from removal of the first medium from the upper part. There is also an inlet for supplying a second medium to the lower part, and an outlet for removal of the second medium in the lower part. A first type of cells can be present in a scaffold in the upper part, and a second type of cells can be present in a scaffold in the lower part. The first type of cells and the second type of cells are in functional contact. As shown, there is no physical separation between the first type of cells in the upper part and the second type of cells in the lower part. However, there can be a semi-permeable membrane at this interface of the upper and lower parts. There can also be a third type of cells in a scaffold between the first type of cells in the scaffold in the upper part and the second type of cells in a scaffold in the lower part. This type of reactor chamber is shown in FIG. 13A with specific cell types and media, but it is to be understood that different cell types, such as macrophages, fat pad cells, and synovial cells can also be placed in this reactor chamber. It is also to be understood that any medium can be selected for perfusion through the inlet(s) and outlet(s). This figure illustrates an exemplary embodiment of a reactor chamber that can be used within the bioreactors disclosed herein.

This type of reactor chamber can be connected in series, so that 2, 3 or 4 reactor chambers are connected. In some embodiments, the upper parts of the reactor chambers in series are interconnected via a passage so that medium that enters one of the upper parts of the reactor chambers enters the upper parts of the other reactor chambers connected in the series. In other embodiments, the lower parts of the reactor chambers in series are interconnected via a passage so that medium that enters one of the lower parts of the reactor chambers enters the lower parts of the other reactor chambers connected in the series. In further embodiments, both a) the upper parts of the reactor chambers in series are interconnected via a passage so that medium that enters one of the upper parts of the reactor chambers enters the upper parts of the other reactor chambers connected in the series; and b) the lower parts of the reactor chambers in series are interconnected via a passage so that medium that enters one of the lower parts of the reactor chambers enters the lower parts of the other reactor chambers connected in the series.

In some embodiments, mechanical actuation or perturbation of tissues in a bioreactor, as described herein, can comprise a "gentle" application of load, for instance <10% strain for 1 hour a day, that mimics the general mechanical environment of the joints without causing damage, and it generally promotes the production and maintenance of better tissue. In other embodiments, mechanical actuation or perturbation can comprise >10% strain that can induce a response similar to an injury response.

The devices, systems, and techniques so far described can be used to facilitate the growth of different tissues, such as tissue found in an organ, for example, an osteochondral microtissue construct from bone. The proposed construct (shown for example in FIG. 1) involves a layered osteochondral tissue composite including, from bottom to top: bone, osteochondral interface, cartilage, and synovium, cultured within a perfusion-ready container mold. As described above, the bone construct can be peripherally surrounded by endothelium to simulate the biological effects of blood vessels and the vasculature on OA. The endothelium can in some cases extend from its location shown in FIG. 1 to form capillary-like structures within the osteoblast construct. Culture-expanded human vascular endothelial cells can be used to form the endothelial lining. The cartilage construct can in some cases also be peripherally surrounded by endothelium, or, as shown in FIG. 1, can be surrounded by human fibroblast (hf) material. Such a layer of hf material can help to simulate interstitial cellular material present in many tissues, for example, the inner lining of the synovial cavity.

Endothelial cells release factors such as fibroblast growth factors (FGFs), interleukin-1β (IL-1β), and interleukin-6 (IL-6), and nitric oxide (NO) which influence both bone and osteoclast behavior, thereby regulating bone formation and resorption. In particular, endothelial cells provide a robust source of bone morphogenetic protein-2 (BMP-2) which enhances the osteogenic phenotype in bone and bone-progenitor cells.

In turn, endothelial cells are the target of many bone-derived signals, such as parathyroid hormone (PTH), insulin-like growth factors types 1 and 2 (IGF-1 and IGF-2), basic fibroblast growth factor (bFGF), platelet derived growth factor (PDGF), and vascular endothelial cell growth factor (VEGF).

Each type of tissue used in the devices, systems, and methods described herein can be formulated with the use of scaffold crosslinking technologies, such as projection stereolithography (PSL) to incorporate internal 3D spatial features which permit optimal tissue formation and medium perfusion. For example, 500-micron-diameter channels can be fabricated within the bone construct to aid in nutrient dispersion throughout the construct. Bone can be formed by seeding and culturing mesenchymal stem cells (MSCs) in photocrosslinked collagen/hydroxyapatite. Collagen and hydroxyapatite, or $Ca_{10}(PO_4)_6(OH)_2$, are primary components of bone, and both are frequently used in tissue engineered bone constructs. Cartilage can be engineered by seeding MSCs in a photo-activated/crosslinked polymeric gel, such as a collagen/chitosan gel, and treated with TGF-β3. Chitosan can be advantageous, as it shares some structural characteristics with glycosaminoglycans, a critical component of cartilage responsible for many of its specific mechanical properties. With its many primary amine groups, chitosan can also aid in collagen crosslinking.

Osteochondral interfaces can be formed from a variety of cellular and other materials arranged in various combinations with one another. An exemplary osteochondral interface can be formed by placing a layer of MSC-laden collagen type I hydrogel between the chondral and osseous layers. The synovial lining can be generated with MSCs seeded in crosslinked polyethylene glycol alone and cultured in non-inductive medium. These conditions have been shown in experiments to be capable of maintaining a fibroblastic phenotype in MSCs. As previously mentioned, the endothelial component can comprise endothelial cells embedded in collagen to surround the osteochondral elements. Collagen gels can be selected based on their susceptibility to modification and contraction by endothelial cells and osteoblasts, which can result in a tight fit around the osteoblast construct.

As there are limited differentiated cell sources available for cartilage and bone tissue engineering, adult multipotent mesenchymal stem cells (MSCs), with their well-characterized ability to differentiate into chondrocyte- and osteoblast-like cells, represent an advantageous candidate cell source for engineering these tissues. Human MSCs derived from bone marrow or from adipose (lipoaspirate) can be used as the progenitor cell population to engineer the bone, cartilage, and synovium components of the microtissue. However, the microtissue system described herein is compatible with constructs derived from any type of progenitor or primary cell. Indeed, induced pluripotent stem cells, with their ability to be propagated to meet the high cell requirements of tissue engineering, represent an attractive, high-quality cell source and provide one exemplary alternative source.

Bioreactor designs can include two separate circulating feeding/delivery systems, such as those shown in FIG. 1 including lower chambers 128, 130 and upper chambers 132, 134, which may be mixed if desired. A first system (e.g., chambers 132, 134) can supply an upper "synovial compartment" and can be separated by an upper screen (such as upper porous screen 126) having 20 μm pores, which in some cases can include a 0.2 μm filter lining. An outer surface of the upper screen can be layered with endothelial cells which adhere thereto and develop after the cells are delivered by perfusion once the construct is assembled. The inner surface of the screen can be lined with a collar of MSC-embedded photo-polymerized hydrogel to constitute the synovium. A second system (e.g., chambers 128 and 130) can supply the bony tissue construct and can be separated from the bone with a rigid wall (e.g., lower porous screen 124) with ≥20 μm pores, thus delivering nutrients as well as allowing endothelial cells and other cells to adhere to and migrate into the bony tissue and create new biologically relevant niches.

As described above, bioreactor systems can include mechanical loading mechanisms. In one exemplary design, the loading device includes a 3 mm loading surface having an unloaded position <0.5 mm from the cartilage surface, and is configured for loading of 5% strain (100 μm) at 0.1 Hz. This combination of strain and loading rate should be chondro-stimulatory in engineered cartilage constructs. Furthermore, extreme loading can be applied in conjunction with stimulation by biochemical stresses to simulate physical injury within the microtissue system. In alternative embodiments, the mechanical loading can be force- or stress-driven rather than strain-driven.

One aspect of the microtissue described herein is its ability to mimic the tissue relationships within the osteochondral complex of the articular joint and to characterize responses to mechanical, toxicological, pathological and inflammatory insults or perturbations. The application of the devices, systems, and methods described herein toward these types of studies can proceed according to several steps. First, behavior of the microtissue grown using the devices, systems and methods described herein can be validated under non-stressed conditions to confirm proper matrix production, differentiation marker expression, and tide mark development. Second, the system can be perturbed with mechanical, chemical, and/or toxicological stresses, insults, or perturbations to demonstrate that the microtissue responds according to published in vivo studies. Third, once validated, the system can be used to investigate biological process not easily studied by traditional means. For example, to study the effects of mechanical injury, the cartilage component can be pre-injured prior to microtissue assembly to study the effects of damaged cartilage on bone health. Alternatively, the assembled and matured microtissue can be impacted to study changes in cartilage and bone anabolic/catabolic pathways and disruption of the tidemark. Similarly, the microtissue system can be employed as a high-throughput in-vitro model to assess the effects of treatment with glucocorticoids, pro-inflammatory cytokines, anti-inflammatory biologics, even biomaterial wear debris, such as titanium and polyethylene microparticles, on osteochondral health. Microtissue systems grown using the devices, systems, and methods described herein offer novel capabilities for investigating the pathogenic mechanisms of OA as well as serving as a high-throughput platform to test candidate DMOADs.

In some methods for developing functional endochondral microtissue, the components of a bioreactor platform (such as including a shell, inner body, upper ring, and other components, similar to those of bioreactor reactor chamber 100) can initially be fabricated, and then the platform design and integrity can be verified using, e.g., structural and media (pH, oxygen, etc.) tests.

Mesenchimal Stem Cells and Induced Pluripotent Stem Cells

The disclosed methods include the use of cartilage, bone, synovium and adipose tissues. These are mammalian, and can be human or veterinary.

Physiologically relevant cartilage, bone, synovium and adipose tissues can be generated from MSCs or iPSCs from the same individual or from different individuals. Chondrocytes are the major cell type in cartilage. Other cells such as cartilage progenitor cells are also present, but their number is limited. Several tissue specific cell types reside in bone, including osteoblast, osteocyte, lining cells and osteoclast; both osteocytes and lining cells are related to osteoblasts. The synovium contains fibroblast-like synoviocytes (FSs; 98%) and macrophages (2%), with the former considered as the major cell types responsible for OA pathogenic mechanisms. For adipose tissues, cells can be divided into adipocytes and those in stromal capsular fraction (SVF), a heterogeneous mixture of adipose stromal cells (ASCs; 15-30%), endothelial cells, pericytes, and immune cells. In addition to the tissue specific cells, nerve and vascular system are also found in joints, as in most tissues/organs. OA is associated with altered innervation patterns, generally considered as a consequence of other tissue pathological changes. Therefore, in some embodiments, the disclosed mJoint may also include functional nerve tissue. The microfluidic circulation included in the mJoint system is equivalent to a functional vascular system. Generation of macrophages from human iPSCs had also been reported.

In some embodiments, chondrocytes, osteoblast and adipocytes are generated from human MSCs, and 3D osteochondral and adipose tissues are produced. MSC differentiation can then be verified using, e.g., histological and reverse transcription polymerase chain reaction ("RT-PCR") techniques. In some embodiments, undifferentiated MSCs are encapsulated in a collagen type 1 gel to form a mesenchymal construct, or in PEG to form a synovium. In other embodiments, pre-differentiated osteoblasts are encapsulated in hydroxyapatite-containing collagen type 1 gel to form an osteoblast construct. In yet other embodiments, pre-differentiated chondrocytes are encapsulated in a collagen type 1/chitosan gel to form a chondrocyte construct. Endothelial cells can also be isolated and encapsulated in a collagen type 1 gel to form an endothelium.

The various microtissue cellular components thus formed (e.g., mesenchymal construct, synovium, osteoblast construct, chondrocyte construct, and endothelium) can then be verified for viability and tissue type, using, e.g., 3-(4,5-dimethylthiazol-2-yl)-5-(3-carboxymethoxyphenyl)-2-(4-sulfophenyl)-2H-tetrazolium ("MTS"), Live/Dead staining, and/or histology/immunohistochemistry ("IHC") techniques.

Although MSCs represent a simple and direct cell source for joint engineering, invasive procedures are required for cell collection, and their expansion capacity is finite, thus limiting the number of mJoint organs that may be produced with a given batch of MSCs and thus the types of assays that may be performed. Human iPSCs possess unlimited proliferation capacity and capability of pluripotent differentiation into cells of all germ lineages, including the cell types present in joints, and thus hold great potential in modeling human joint tissue. In principle, a single batch of iPSCs can serve as the starting cell source to produce unlimited tissue types of identical genotype that may be used together in a single platform.

Therefore, in some embodiments, iPSCs are generated from human bone marrow stem cells (M-iPSCs), and MSC-like cells (iMPCs) are derived from the iPSCs thus obtained. The generated iMPCs have chondrogenic, osteogenic, and adipogenic capabilities, and are used to produce human osteoblasts, chondrocytes and adipocytes, macrophages, and fibroblasts.

The disclosed mJoint provides a 3D cell culture platform containing both cells and extracellular matrix (ECM), and thus mimics native joint tissues by: (1) simulating interstitial fluid and ECM as experienced by cells in vivo; (2) allowing cell attachment, maintaining cell phenotype, and supporting proper cell function in a 3D context for more natural cell-cell communication; and (3) eliminating potential complications due to degradation products from different ECM components when studying paracrine interactions between tissues.

Figure 27A:
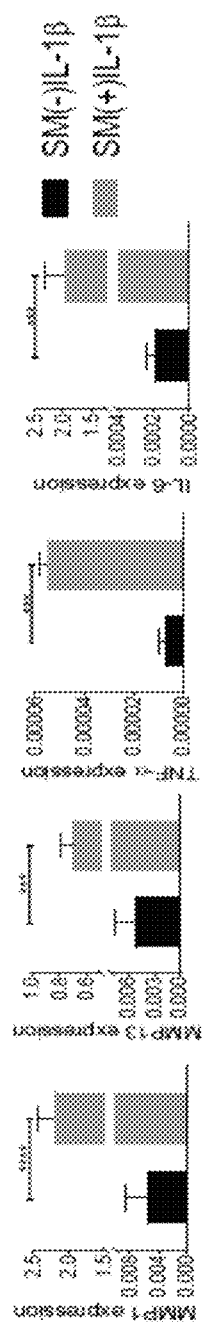
FIGS. 27A-27B. (A) Gene expression levels relative to RPL13a in SM, with (+) or without (−) IL-1 treatment. (B) Chondrogenic and degenerative genes expression in cartilage after the treatment of the conditioned medium from normal or inflamed SM. SM: synovium, CM: conditioned medium.
Figure 27B:
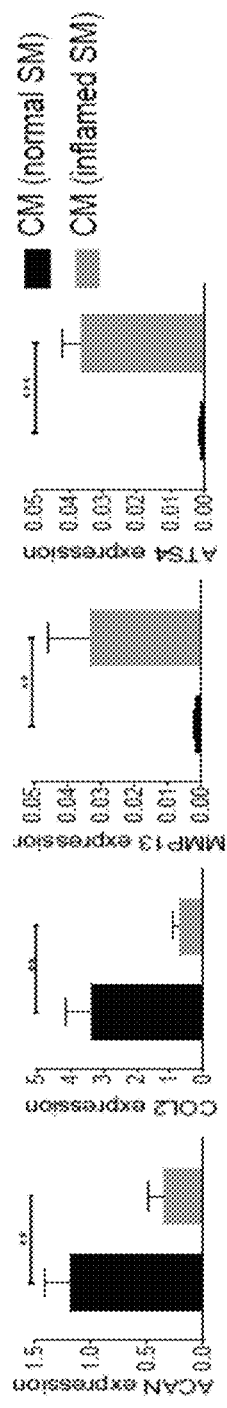
Figure 28:
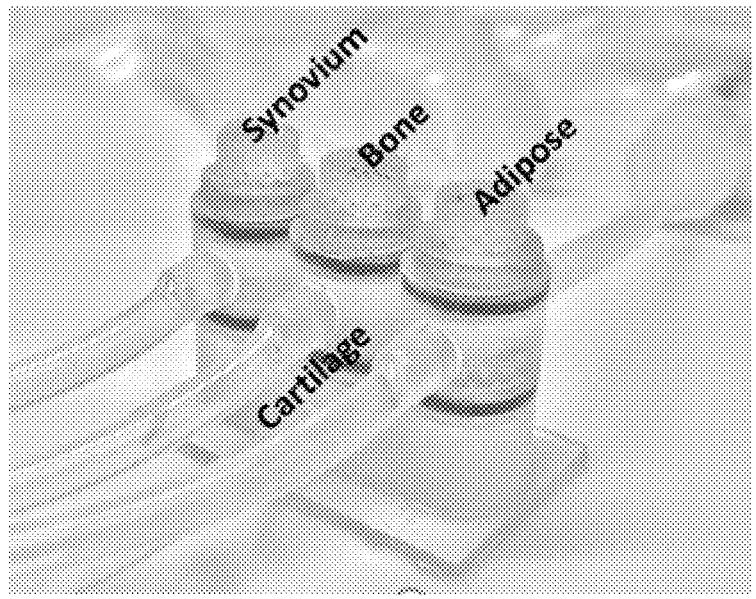
FIG. 28. Digital image showing integration of the osteochondral complex of synovial membrane (SM), and fat pad (FP) tissues to form a microJoint bioreactor.

Several biomaterials may be used to produce the disclosed mJoint constructs. In one embodiment, given the prevalence of collagen in joint tissue matrix, the 3D mJoint constructs are engineered by encapsulating iPSC-derived joint cells or MSC-derived joint cells within a photo-crosslinkable methacrylated gelatin (mGL) in a top chamber. The mGL displays excellent biocompatibility and support for cell growth, and cartilage, bone and adipose tissues are successfully engineered from human iMPCs seeded within mGL, with differentiation occurring within three weeks (see Methods below). The top chamber containing the mGL encapsulating the iPSC-derived joint cells or MSC-derived joint cells is then placed on top of a bottom chamber containing a polycaprolactone scaffold that constitutes the osseous component to create a 3D biphasic mJoint osteochondral construct (FIGS. 27-28).

The components of a fabricated bioreactor platform can then be combined with these and/or other microtissue cellular components to assemble a bioreactor similar to bioreactor 100. Performance of the microtissues in the bioreactor can then be verified using, e.g., leakage tests, micro computed tomography ("mCT"), magnetic resonance imaging ("MRI"), MTS, Live/Dead, imaging, and/or histology/IHC techniques.

In some embodiments, a mechanical loading system can be provided that is configured to provide a physiological load to the tissue in the bioreactor. Such a loading system can then be verified using, e.g., mCT, MRI, histology/IHC, or imaging techniques.

In some embodiments, the microtissues in a bioreactor can be treated with various perturbations, such as mechanical, chemical, toxicological, and/or biological insults. For example, the microtissue can be mechanically injured by providing a pathogenic load, and the microtissue response can then be measured. In one embodiment, bone pathology can be investigated by treating an osteoblast construct with glucocorticoids and measuring the microtissue response. In another embodiment, bone inflammation can be investigated by treating an osteoblast construct with pro-inflammatory cytokines (e.g., TNF-α, etc.) and measuring the microtissue response. In yet another embodiment, bone exposure to particulates can be investigated by treating an osteoblast construct with titanium microparticles and measuring the microtissue response. In another embodiment, the microtissues can be exposed to any of various implant wear debris, such as microparticles of ultra-high-molecular-weight polyethylene (UHMWPE), titanium, chromium/cobalt, etc., and the microtissue response can be measured. In another embodiment, the microtissues can be exposed to various cells, such as cells typical of an inflammatory environment, and the microtissue response can be measured. In each of these embodiments, the microtissue response can be measured using, e.g., ELISA, imaging, histology/IHC, mCT, MRI, or matrix metalloproteinases ("MMP") activity techniques.

In some embodiments, cartilage health can be tracked based on gene expression activities, e.g., using adeno-associated virus (AAV)-based tissue-specific promoter-reporter constructs.

Morphology of Engineered Tissue Components in the mJoint Bioreactor

Chondral components and osteo components are formed in the mJoint bioreactor after four weeks in culture. A capillary network is also formed within the mJoint bioreactor. FIG. 33 shows a biphasic, adult stem cell-based based osteochondral construct (CC, chondral component; OC, osteo component) after >4 weeks of culture, and a micro-computed tomography image of the calcified osteo component. FIG. 34 shows an engineered vascularized bone construct formed by seeding endothelial cells into the osseous component of the osteochondral complex. The endothelial cells form capillary network in the engineered bone compartment. FIG. 35 shows the histology of the infrapatellar fat pad (adipose tissue containing lipids).

Production of Normal and Diseased mJoints

In screening candidate drugs that may modify, stop or reverse progression of OA, and that act either locally (synovial fluid) or systemically, the key consideration is that joint diseases not only involve all elements in one joint, but also often affects several joints at the same time. Therefore, both local and systemic factors must be considered. Accordingly, to accommodate both local and systemic environment, the disclosed mJoint harbors optimized culture conditions for different tissues. In the native joint, the articular cartilage is bathed in serum-free synovial fluid on one side and connected on the other side to subchondral bone that is vascularized. The oxygen tension of synovial fluid in humans is reported to be 6.5-9.0%. Studies have shown that chondrocytes exhibit augmented phenotypic stability when cultured in hypoxic environment. Hypoxia culture not only enhances chondrogenic gene expression and suppresses hypertrophy, but also promotes the re-differentiation of chondrocytes, via the hypoxia-inducible factor (HIF) pathway. Both IPFP and synovium are vascularized tissues, but synovium is in direct contact with synovial fluid while IPFP is extrasynovial.

The disclosed mJoint bioreactor may be assembled in different ways to model a healthy joint or an osteoarthritic knee joint and study the pathogenesis of osteoarthritis and/or diabetes-associated joint complication. All tissues are individually fabricated as modules, and inlets are used to introduce stimuli, as well as therapeutics, with the versatility to be easily disconnected and re-connected. Schematic examples of different embodiments of the mJoint bioreactor assembly are shown in FIGS. 20-23, with the bottom flow containing medium with high serum concentration under normoxia, and the top flow containing medium with low serum and under hypoxia.

Figure 16:
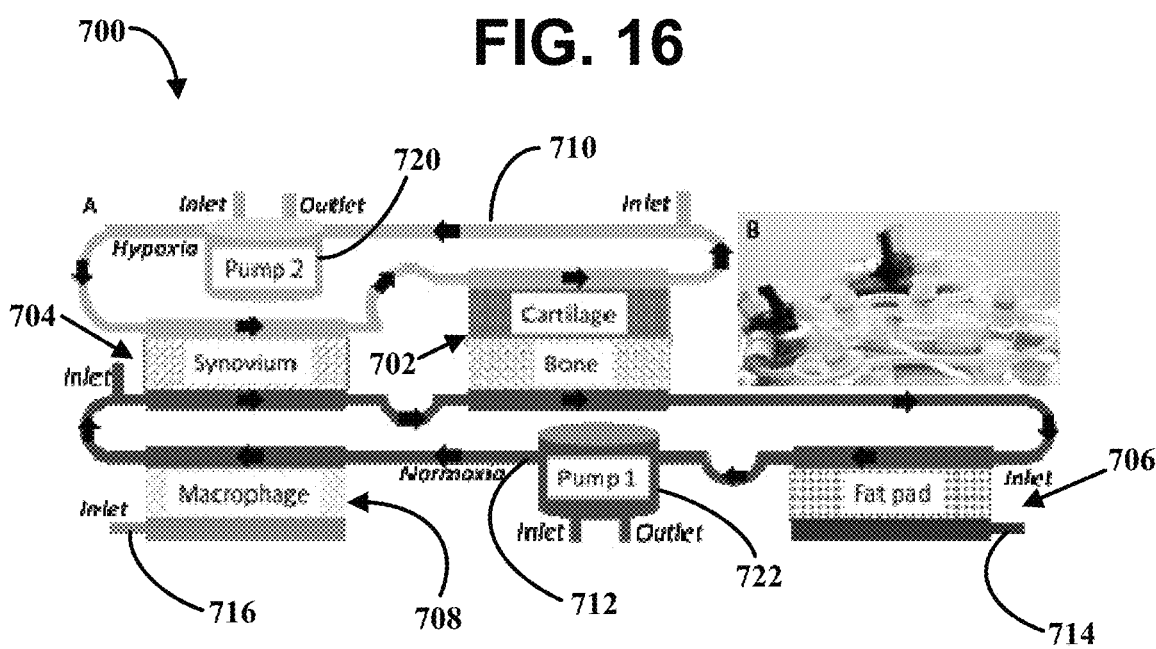
FIG. 16 is a schematic illustration of an mJoint bioreactor chip. Inlets are used to introduce stimuli, as well as therapeutics. The bottom flow contains the medium with high serum concentration and normoxia, and the top flow contains the medium with low serum and hypoxia. All the tissues are individually fabricated as modules, thus with the versatility to be easily disconnected and re-connected.

FIG. 16 shows a tissue bioreactor 700 that mimics a healthy joint or an OA joint with a partial-thickness cartilage defect in which cartilage still covers the bone. Bioreactor 700 includes a first reactor chamber 702 containing a lower layer of osseous tissue such as bone (osteocytes) and an adjacent layer of cartilaginous tissue (such as chondrocytes or other chondrogenic cells). Bioreactor 700 further comprises a second reactor chamber 704 containing synovial tissue such as synovium, a third reactor chamber 706 containing adipose tissue (such as an infrapatellar fat pad), and a fourth reactor chamber 708 that contains macrophages. A first fluidic passageway 710 forms a first fluid circuit for circulating a hypoxic tissue-specific nutrient medium through the first reactor chamber 702 and second reactor chamber 704, but not the third and fourth reactor chambers 706, 708. A second fluidic passageway 712 forms a second fluid circuit for circulating normoxic tissue-specific nutrient medium through the first, second, third and fourth reactor chambers.

One or more perturbation source is provided in bioreactor 700 to provide a preselected perturbation to at least one of the reactor chambers or one or both of the first and second fluidic passageways. In the embodiment illustrated in FIG. 16, the perturbation source is an inlet 714 into third chamber 706 and an inlet 716 into fourth chamber 708. Perturbations (such as drugs) can be selectively introduced into either or both of inlets 714, 716 to test the effect of the perturbation on the system of bioreactor 700. For example, it can be determined if specific perturbations of the fat pad in third chamber 706 affect the bone in reaction chamber 702, synovium in reactor chamber 704, or macrophages in reactor chamber 708. Similarly, perturbations to the macrophages in reactor chamber 708 can be tested to assess their effect on other tissue elements of the bioreactor system.

A pump 720 circulates the fluid through fluidic passageway 710 and also has an inlet and outlet through which the fluid can be introduced into and exit from passageway 710. A separate pump 722 circulates a separate fluid through passageway 712. The oxygen content of the fluid circulated through the fluidic passageways 710, 712 can be maintained at different levels. For example, the fluid circulated through passageway 710 is hypoxic relative to the fluid circulated through passageway 712 to mimic the lower oxygen concentration of the synovial fluid that bathes the synovium and its underlying cartilage, as compared to bone that is oxygenated by the circulatory system at a higher oxygen concentration. The hypoxic fluid in passageway 710 therefore comes into direct contact with the cartilage layer in reaction chamber 702 and the synovium in second reaction chamber 704 to better mimic physiologic conditions in the joint in which relatively hypoxic synovial fluid bathes the cartilage and synovium. In contrast, the more highly oxygenated fluid in passageway 712 comes into direct contact with the fat pad and macrophages in reaction chambers 706, 708 to mimic the greater oxygenation of those tissues that are more directly perfused by arterial oxygen.

Figure 17:
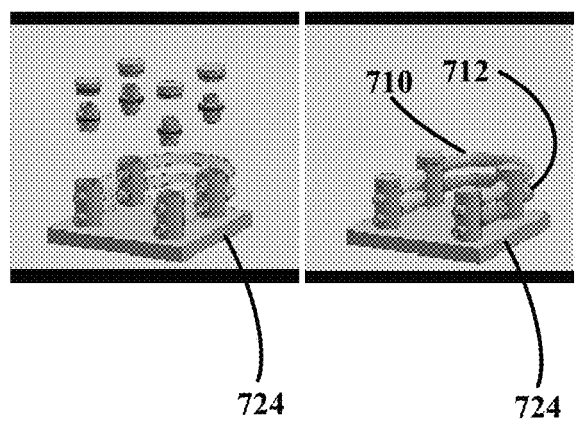
FIG. 17 is a schematic illustration of the mJoint bioreactor chip incorporating the bioreactor chambers shown in FIG. 16.
Figure 18:
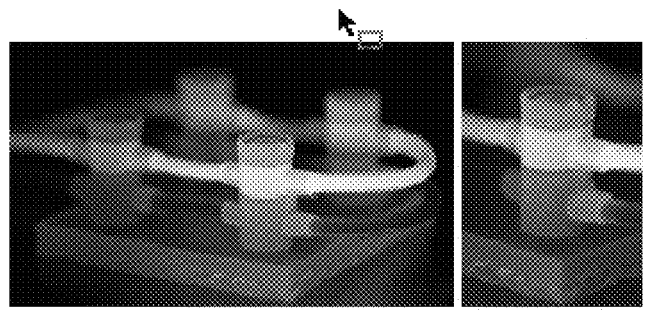
FIG. 18 shows the construction/assembly and function of microbioreactors. (Left) Assembly of top and bottom chambers of a microbioreactor platform. (Right) Illustration of actual, individual medium flow in top and bottom chambers. The different shades of the upper and lower fluid passageways illustrate the relatively hypoxic fluid in the upper passageway and the higher oxygen content (normoxic) in the lower fluid passageway.
Figure 19:
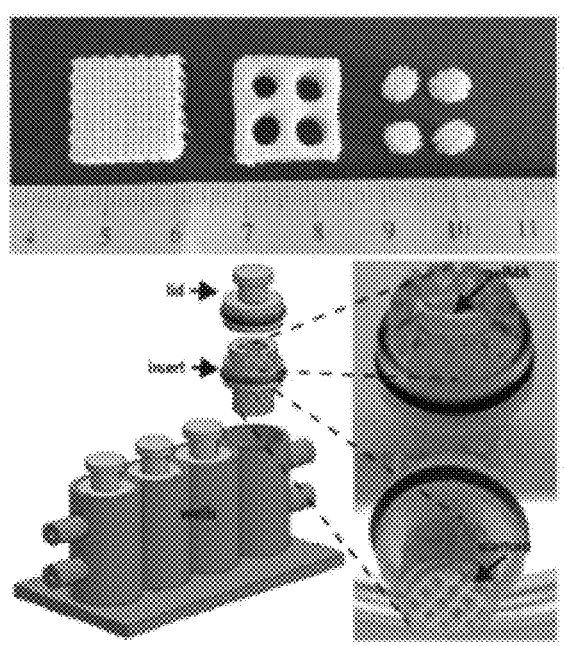
FIG. 19 shows the assembly of an osteochondral construct and examples of biomaterials used for the biphasic construct in which the cells are human mesenchymal stem cells. In the chondral component (top) the cells are in a photocrosslinkable methacrylated gelatin carrier, and in the osseous component (bottom) the cells are in a polycaprolactone scaffold.

As shown in FIG. 17, the perfusion system for the bioreactor 700 can be incorporated into a single bioreactor that includes multiple chambers that replicate the well positions of a multi-well plate (such as a 96-well plate). In the illustrated embodiment the four different bioreactor chambers are inserted as modules into four different receptacles of the bioreactor base, and fluid passageways 710, 712. FIG. 18 illustrates with different shading the differential oxygenation in fluid passageways 710, 712.

Figure 20A:
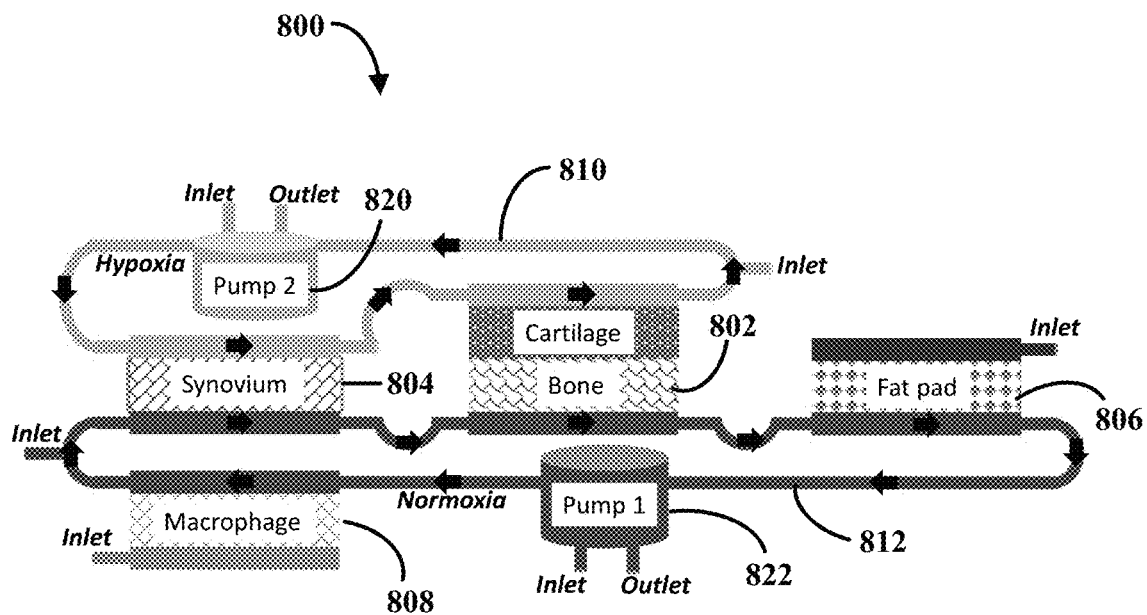
FIG. 20A is a schematic diagram of one embodiment of the mJoint bioreactor chip that may be used to model a healthy joint or osteoarthritic joint with a partial-thickness cartilage defect.
Figure 20B:
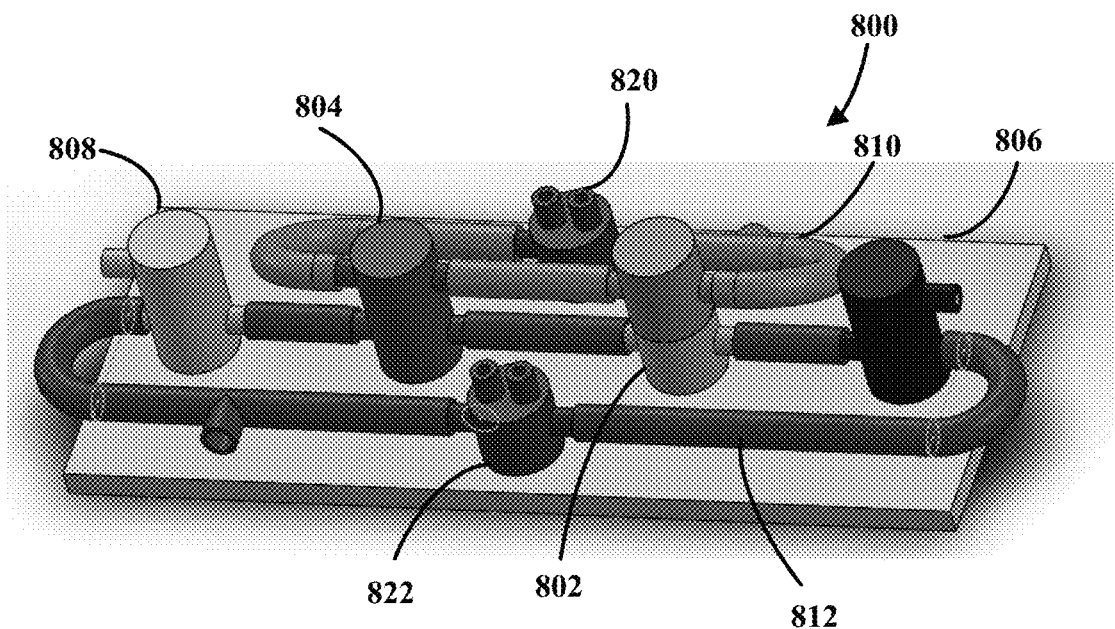
FIG. 20B is a schematic top perspective view of the bioreactor chip of FIG. 29A illustrating the three-dimensional features of the bioreactor chip. Different reactor chambers are at different heights from the base of the biochip, and the relatively hypoxic fluid circulates through fluid passageways above the relatively normoxic fluid circulation passageways.

FIG. 20A and FIG. 20B show a tissue bioreactor 800 that mimics a healthy joint or an OA joint with a partial-thickness cartilage defect in which cartilage still covers the bone. Bioreactor 800 includes a first reactor chamber 802 containing a lower layer of osseous tissue such as bone (osteocytes) and an adjacent layer of cartilaginous tissue (such as chondrocytes or other chondrogenic cells). Bioreactor 800 further comprises a second reactor chamber 804 containing synovial tissue such as synovium, a third reactor chamber 806 containing adipose tissue (such as an infrapatellar fat pad), and a fourth reactor chamber 808 that contains macrophages. A first fluidic passageway 810 forms a first fluid circuit for circulating a hypoxic tissue-specific nutrient medium through the first reactor chamber 802 and second reactor chamber 804, but not the third and fourth reactor chambers 806, 808. A second fluidic passageway 812 forms a second fluid circuit for circulating normoxic tissue-specific nutrient medium through the first, second, third and fourth reactor chambers. The bioreactor of FIG. 20 differs from that of FIG. 16 in that reactor chamber 806 is on an upper level with reactor chambers 802, 804 instead of on a lower level with reactor chamber 808.

Figure 21A:
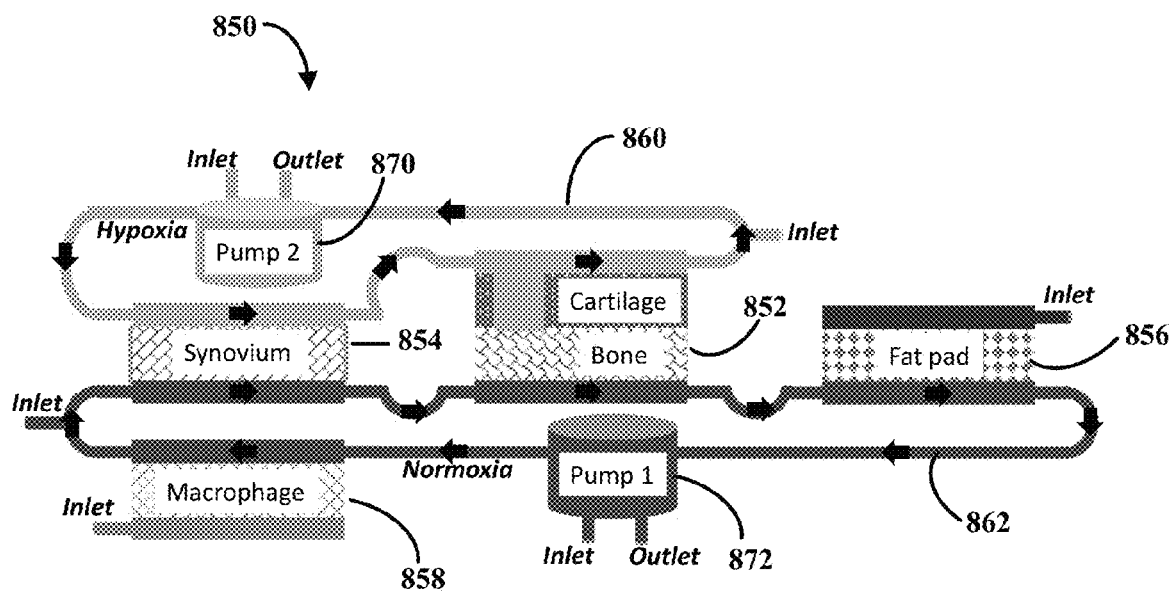
FIG. 21A is a schematic diagram of one embodiment of the mJoint bioreactor chip with a full-thickness cartilage defect.
Figure 21B:
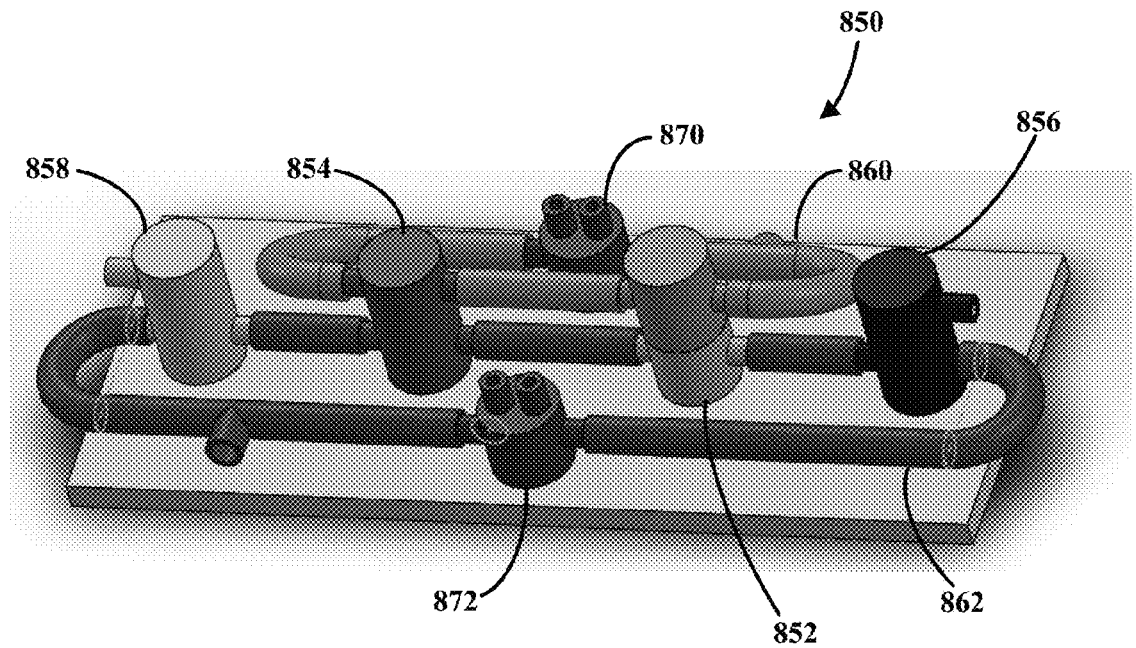
FIG. 21B is a schematic top perspective view of the bioreactor chip of FIG. 30A illustrating the three-dimensional features of this embodiment of the bioreactor chip.

FIGS. 21A and 21B show another embodiment of the tissue bioreactor 800 that mimics a joint with a complete-thickness cartilage defect in which cartilage only covers a portion of the bone. Bioreactor 850 includes a first reactor chamber 852 containing a lower layer of osseous tissue such as bone (osteocytes) and an adjacent layer of cartilaginous tissue (such as chondrocytes or other chondrogenic cells). Bioreactor 850 further comprises a second reactor chamber 854 containing synovial tissue such as synovium, a third reactor chamber 856 containing adipose tissue (such as an infrapatellar fat pad), and a fourth reactor chamber 858 that contains macrophages. A first fluidic passageway 860 forms a first fluid circuit for circulating a hypoxic tissue-specific nutrient medium through the first reactor chamber 862 and second reactor chamber 864, but not the third and fourth reactor chambers 866, 868. A second fluidic passageway 872 forms a second fluid circuit for circulating normoxic tissue-specific nutrient medium through the first, second, third and fourth reactor chambers.

Figure 22A:
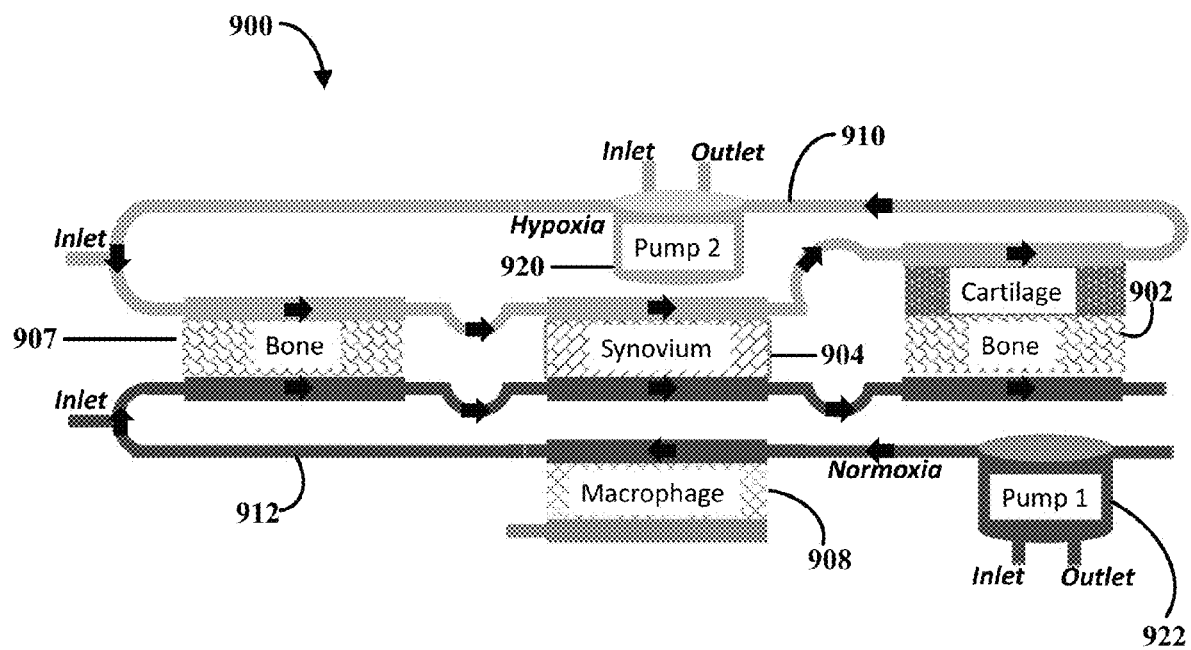
FIG. 22A shows a model of a joint with hemiarthroplasty suitable to study the effects of wear debris with or without bacterial ligand coating, which is directly embedded in the bone and synovium chambers. In a hemiarthroplasty (also known as a unicompartmental knee arthroplasty) damaged cartilage is removed in only one of the knee compartments such that part of the bone is protected by cartilage and the other part of the bone is not. Separate bioreactors that contain 1) only bone and 2) a combination of bone and cartilage thereby mimic such post-surgical conditions in a joint.
Figure 22B:
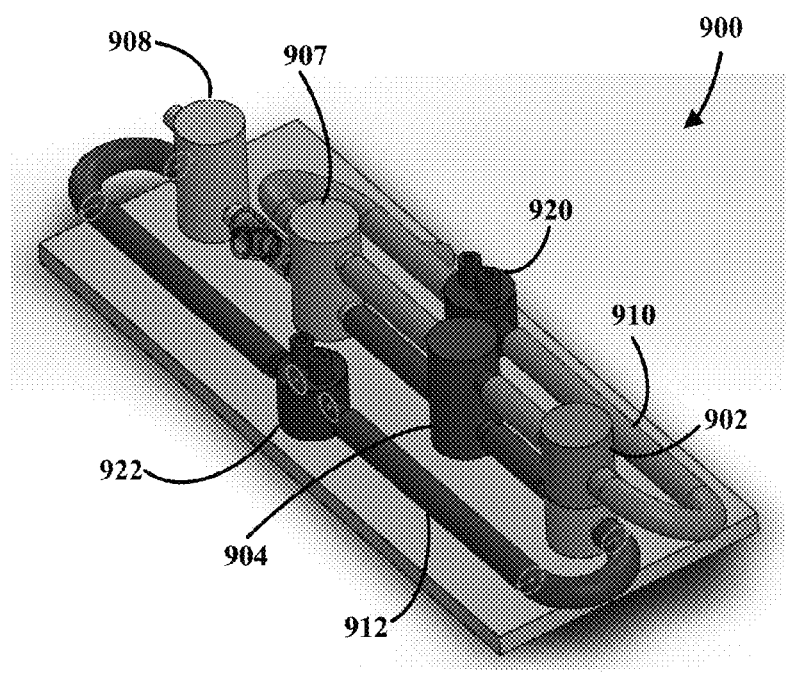
FIG. 22B is a schematic top perspective view of the bioreactor chip of FIG. 22A.

FIGS. 22A and 22B show a tissue bioreactor 900 that mimics a joint that has undergone a hemoarthroplasty in which part of the bone is no longer covered by cartilage and part of the bone retains it protective cartilage covering. Bioreactor 900 includes a first reactor chamber 902 containing a lower layer of osseous tissue such as bone (osteocytes) and an adjacent layer of cartilaginous tissue (such as chondrocytes or other chondrogenic cells). Bioreactor 900 further comprises a second reactor chamber 904 containing synovial tissue such as synovium, a third reactor chamber 907 containing only bone and not cartilage to mimic bone from which cartilage is absent. A fourth reactor chamber 908 contains macrophages. A first fluidic passageway 910 forms a first fluid circuit for circulating a hypoxic tissue-specific nutrient medium through the first reactor chamber 902 and second reactor chamber 904, but not the third and fourth reactor chambers 906, 908. A second fluidic passageway 912 forms a second fluid circuit for circulating normoxic tissue-specific nutrient medium through the first, second, third and fourth reactor chambers. Each fluidic passageway comes into contact with one face of the layer of cells or tissue in each bioreactor. In those instances in which both the hypoxic and normoxic fluid circuits supply a bioreactor chamber, one face of the tissue in the bioreactor chamber is exposed to hypoxic conditions and the other face of the tissue in the bioreactor is exposed to normoxic conditions.

Figure 23A:
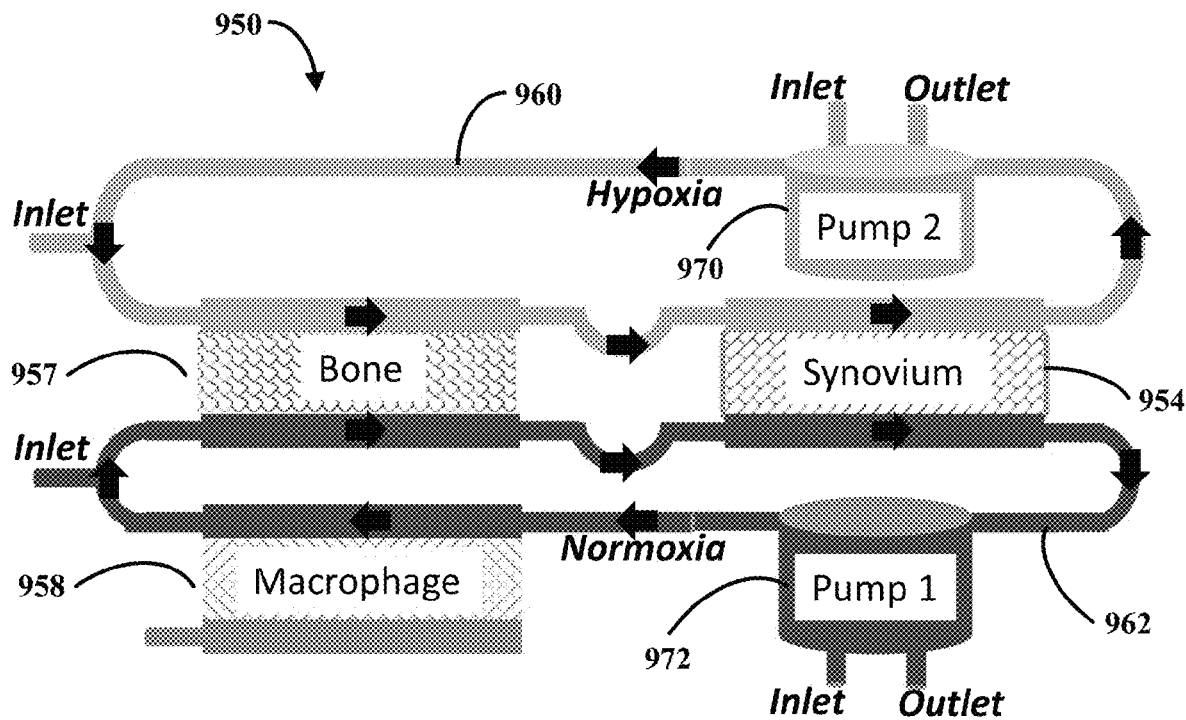
FIG. 23A shows a mJoint bioreactor of a joint with full arthroplasty suitable to study the effects of wear debris with or without bacterial ligand coating, which is directly embedded in the bone and synovium chambers. In a full arthroplasty damaged cartilage is removed from underlying bone, hence the cartilage reactor chamber is not present in this illustrated embodiment.
Figure 23B:
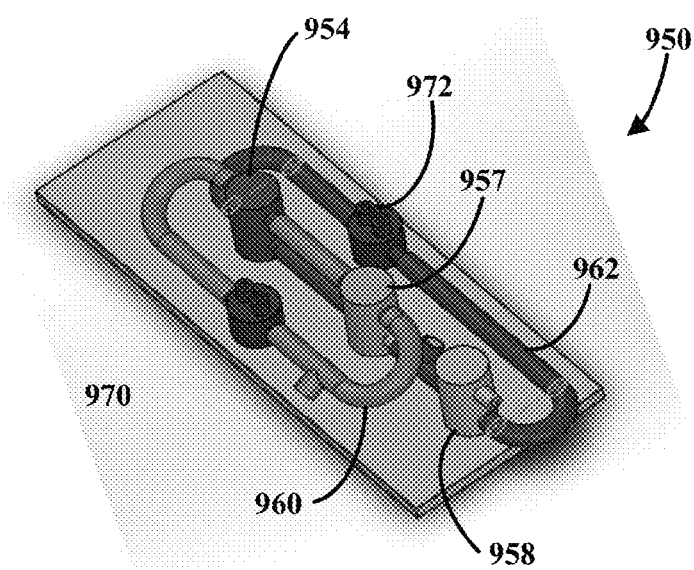
FIG. 23B is a schematic top perspective view of the bioreactor of FIG. 23A.

The bioreactor shown in FIGS. 23A and 23B is similar to that shown in the prior drawings and operates according to similar principles, but the bioreactor has only three reaction chambers and each of the reaction chambers has only bone, only synovium, and only macrophages. There is no reaction chamber that contains both bone and cartilage tissue, to thereby simulate a joint in which cartilage is completely absent from bone, as occurs in advanced osteoarthritis. Bioreactor 950 includes a first reactor chamber 954 containing an isolated layer of synovium and a second reactor chamber 957 containing isolated osseous tissue such as bone (osteocytes). Bioreactor 950 further comprises a third reactor chamber 958 containing only macrophages. There is no fourth reaction chamber. A first fluidic passageway 960 forms a first fluid circuit for circulating a hypoxic tissue-specific nutrient medium through the first reactor chamber 952 and second reactor chamber 954, but not the third and fourth reactor chambers 956, 958. The hypoxic fluid in fluidic passageway is exposed to a first surface of the bone and synovium. A second fluidic passageway 962 forms a second fluid circuit for circulating normoxic tissue-specific nutrient medium through the first, second and third reactor chambers. The normoxic fluid bathes the macrophages without any contribution from the hypoxic fluid circuit. However, the hypoxic fluidic passageway also bathes a second face of the synovium and bone in bioreactor chambers 954, 957.

The tissue media that are circulated through fluid passageways 910 and 912 can be common culture media formulations, such as Dulbecco's Modified Eagle's Medium (DMEM), which is readily available from commercial sources.

Serum supplemented medium generally refers to supplementation with serum, such as fetal bovine serum, commonly at 10% (v:v). A "high serum" concentration can be a concentration of at least 10%, such as 10%, 11%, 12%, 13%, 14%, 15%, 16%, 17%, 18%, 19% or 20%. A "low serum concentration" can be 2% or lower, such as 1.5%, 1%, 0.5% or 0-%. "Low serum" medium includes "serum free" medium. An example of a high-serum universal medium that can be used is: DMEM, high glucose, pyruvate (Gibco), containing 10% fetal bovine serum (FBS, Invitrogen), 1× Antibiotic-Antimycotic (Gibco). An example of a low serum (in this case serum-free) medium: DMEM, high glucose, pyruvate (Gibco), 1× antibiotics-antimycotic (Gibco), and 1× Insulin-Transferrin-Selenium. The serum need not be fetal bovine serum. Other examples include human serum or serum from other mammals.

Normoxic fluid is circulated in fluid passageway 712; such fluid has no adjustment of oxygen tension and therefore retain an atmospheric level of approximately 20% oxygen. Hypoxic medium is generated and maintained, for example, by including an inert gas such as nitrogen, in a gas supply which renders a lower oxygen tension of 5-8% to simulate known oxygen tension in the articular joint of about 6-7%. Hypoxic medium can be generated, for example, by using a hypoxic chamber to generate hypoxic medium, which is then perfused through the bioreactor. For example, such a chamber is available from Coy Laboratory Products (Grass Lake, Mi.).

The generation of wear debris is an inevitable result of normal usage of joint replacements. Wear debris particles stimulate local and systemic biological reactions resulting in chronic inflammation, periprosthetic bone destruction, and eventually, implant loosening and revision surgery. Similar to the response to pathogens, wear particles elicit a macrophage response. Macrophages play multiple roles in both inflammation and in maintaining tissue homeostasis. They initiate an inflammatory cascade, which is characterized by the release of pro-inflammatory and pro-osteoclastic factors. The biological processes involved are complex, redundant, both local and systemic, and highly adaptive. Simultaneously, other distinct macrophage populations inhibit inflammation and protect the bone-implant interface from osteolysis. Therefore, in one embodiment, the disclosed mJoint bioreactor reproduces the generation of wear debris.

Figure 29:
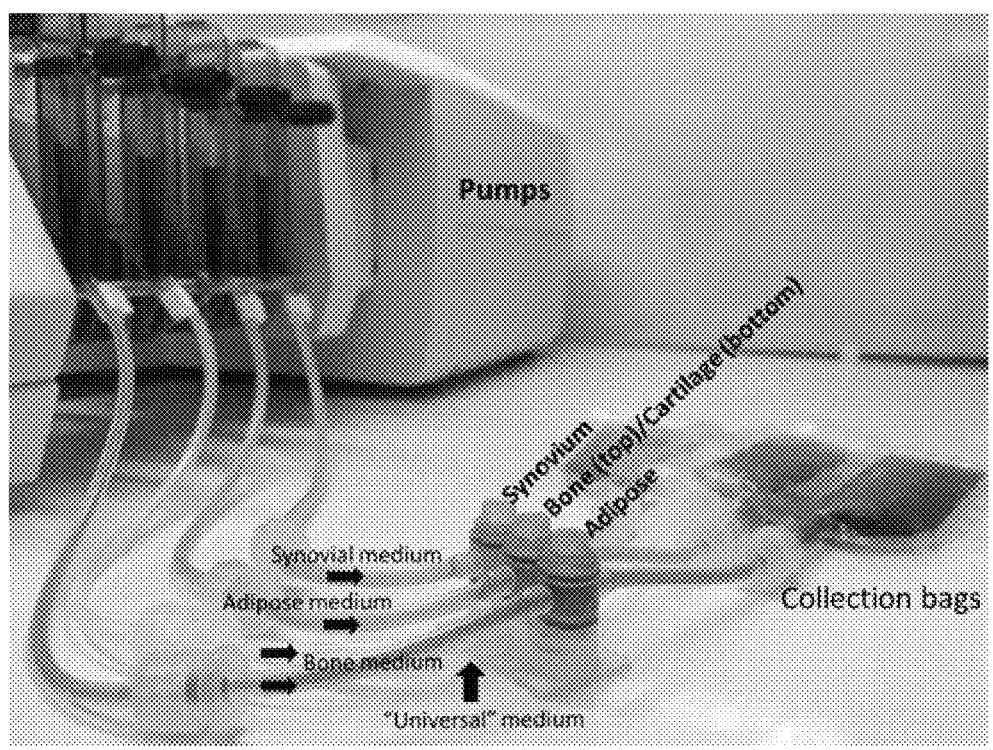
FIG. 29. Digital image showing a pump system and collection bags for different medium.
Figure 30A:
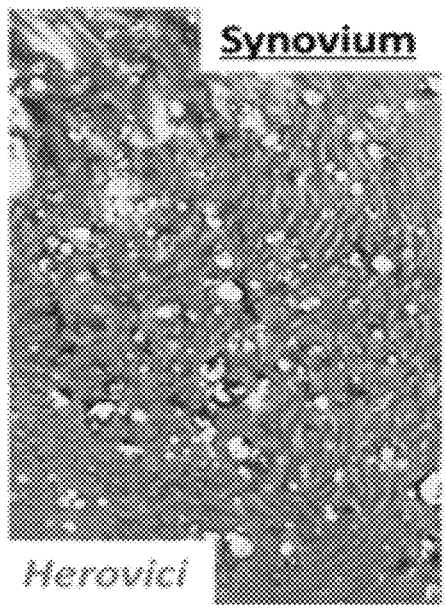
FIG. 30A-30D. Digital images showing an mJoint bioreactor (C), and histological imaging of the engineered joint components (A, B, D).
Figure 30B:
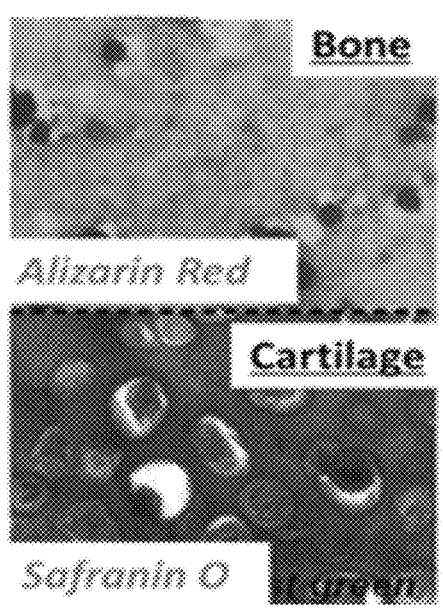
Figure 30C:
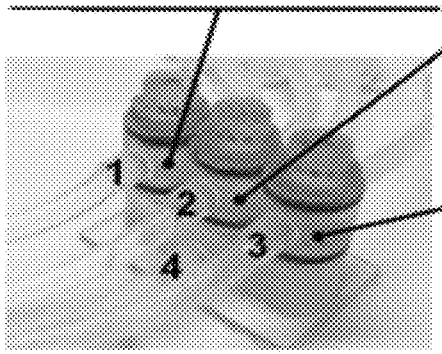
Figure 30D:
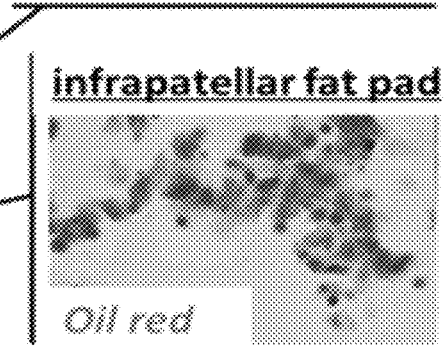

Another embodiment is shown in FIGS. 28 and 29. In these bioreactors, the bioreactor includes i) a first reactor chamber comprising an upper part and a lower part (labeled "synovium"), wherein the first reactor chamber comprises synovial cells, such as synovial tissue, within a scaffold in both the upper part and the lower part, wherein the upper part has an inlet and an outlet for a first normoxic medium. In this embodiment, a second reactor chamber is also present with an upper part and a lower part, wherein the second reactor chamber comprises a) osteoblasts, such as in bone, within a first scaffold in the upper part (labeled "bone"), and b) chondrocytes, such as in cartilage, within a second scaffold in the lower part (labeled "cartilage"), and wherein the osteoblasts and the chondrocytes are in functional contact at the interface between the upper part and the lower part, and wherein the second reactor chamber has an inlet and an outlet for circulating a second normoxic medium through the osteoblasts in the upper part and an inlet and an outlet for circulating first hypoxic medium through the chondrocytes in the lower part. This bioreactor includes a third reactor chamber with an upper part and a lower part, wherein the third reactor chamber comprises fat pad cells, such as adipose tissue, within a scaffold in both the upper part and the lower part (labeled "adipose"), wherein the third reactor chamber has an inlet and an out let for circulating a third normoxic medium through the fat pad cells in the upper part. In this configuration, the lower parts of the first, second and third reactor chambers are interconnected, such that the hypoxic medium entering through the inlet contacts the synovial cells in the lower part of the first reactor chamber, chondrocytes in the lower part of the second reactor chamber, and fat pad cells in the lower part of the third reactor chamber. It should be noted that the first, second and third chambers can be in any order from left to right.

These bioreactors can be used to reproduce the biological conditions in a mammalian joint. Methods include circulating the first nomoxic medium through the upper part of the first reactor chamber comprising the synovial cells within the scaffold; circulating the second normoxic medium through the upper part of the second reactor chamber comprising osteoplbasts within the scaffold; circulating the third normoxic medium through the upper part of the third reactor chamber comprising fat pad cells in the scaffold; and circulating the first hypoxic medium through the lower part of the second reactor chamber, wherein the third hypoxic medium contacts the synovial cells in the scaffold in the lower part of the first reactor chamber, chondrocytes om the scaffold in the lower part of the second reactor chamber, and fat pad cells on the scaffold in the lower part of the third reactor chamber. In some embodiments, the first normoxic medium, the second normoxic medium, and the third normoxic medium are all different. The methods can also include introducing a preselected biological perturbation into at least one of the first reactor chambers, second reactor chambers or third reactor chambers. The preselected perturbation can include one or more of a chemical perturbation, a toxicological perturbation, a mechanical perturbation, a physical perturbation, a biological perturbation, a disease initiator, an active agent, a chemical compound, a hormone, an inflammatory agent, a disease-modifying agent or a therapeutic agent.

The disclosed mJoint bioreactor mimics in vivo growth conditions, by having two separate circulation systems, with the communication between the two systems being conditioned by the various tissues. The inlets are used to introduce different stimuli as well as therapeutics. In some embodiments, the additional inlets to macrophage and fat pad constructs allow exclusive tissue-specific stimulation.

In some embodiments, the disclosed mJoin device includes microwells connected by microfluidic channels, each well with planar dimensions inferior to those of single wells in a 96 well plates. The depth of each well is tailored to contain ~10 µl of volume, but height and radius can be adjusted during fabrication to accommodate higher or smaller volumes, reaching as little as 1 µl of volume. Each microwell is sealed by a removable base and a removable lid. The transport of fluid and molecules through the microfluidic chamber containing the 3D cell constructs is either diffusion-based (concentric medium-filled cavity with the inner circular well housing the construct or tissue allows the fluids to reach the construct and diffuse through it from one side) or perfusion based (medium can exit the system only after being forced to perfuse through 3D construct within the well). Each system is evaluated for optimal differentiation, growth and viability of the mJoint, first by modeling fluid flow and nutrients consumption as described above and recursively improving microfluidic design, then with experimental validation of the optimal design. The perfusion systems described above have two medium inputs and outputs. The flexibility of the additive manufacturing approach allows easy design modification as might be required by the specific test being performed.

In some embodiments, bioreactors and associate components, as described herein, can comprise materials that are transparent to X rays so that it is possible to image by microCT the construct within the bioreactor. Similarly, the bioreactor materials can be such that other imaging techniques, such as fluorescence microscopy, can be used "non-invasively," without removing the constructs from the bioreactor.

In some embodiments, pharmaceutical compositions that include a hydrogel, such as a gelatin, cellulose and/or collagen-based matrix, in combination with bone marrow and/or isolated mesenchymal stem cells and/or induced pluripotent stem cells, are inserted into a diseased mJoint with a defect, such as, but not limited to, a fracture. Gradual osteogenic healing of the defect is then visible through the lid of the mJoint bioreactor. Optionally, the hydrogel is a photocrosslinked gelatin hydrogel. In some embodiments, the hydrogel is a methacrylated gelatin hydrogel, such as a methacrylated hyaluronan hydrogel. The hydrogel can be a mixture of methacrylated gelatin and methacrylated hyaluronan hydrogel. The hydrogel can be a gelatin hydrogel, such as a methacrylated gelatin, and/or methacrylated hyaluronan hydrogel that was photocrosslinked with visible light. In one specific non-limiting example, MSCs (4-20× $10^6$/ml) are seeded in gelatin/hydroxyapatite hydrogels by photocrosslinking, and cultured in BMP-2 included osteogenic media. Cartilage is engineered by seeding MSCs (4-60×$10^6$/ml) in gelatin/hyaluronic acid hydrogel by photocrosslinking, and treated with transforming growth factor-β3 (TGF-β3) included chondrogenic medium. Osteochondral interfaces is formed by placing layers of MSC-laden (4-20×$10^6$/ml) gelatin hydrogels between the chondral and osseous-constructs.

Further, either as a substitute for or in addition to an MSC or iPSC layer, in some cases, a membrane having any of various suitable pore sizes can be situated between any of various tissue layers being cultured in a bioreactor. For example, the membrane could take the place of an MSC or iPSC layer as described above. Further, except where structurally impossible, any of the devices, systems, and components thereof described herein can be used in any of various suitable combinations with one another. For example, any of the bioreactors described herein can be used in combination with any of the fluidic systems (e.g., well plates) described herein, and/or in combination with any of the perturbation sources (e.g., mechanical actuators, chemical perturbations, or toxicological perturbations) described herein. Further, any of the dimensions of such devices and components thereof can be modified to accommodate other components and devices.

Tissue Specific Promoter-Reporter Constructs

As stated above, the health of cartilage and osseous and fat components can be studied and monitored in the mJoint bioreactor based on gene expression activities, such as, but not limited to, using adeno-associated virus (AAV)-based tissue-specific promoter-reporter constructs. Adult stem cells are transduced with different gene promoter-reporter constructs, such as Green Fluorescent Protein (GFP) constructs or Luciferase (Luc) constructs, carrying different cartilage and bone anabolic and catabolic marker genes prior to being used to engineer chondral and osseous tissue components. Examples of cartilage and bone anabolic and catabolic marker genes include, but are not limited to, the human Col II gene, the human Runx2 gene, the human collagen type X alpha 1 gene, the human MMP13 gene, the human CD248 (endosialin) gene, and the human RANKL gene.

The human Col II gene encodes the alpha-1 chain of type II collagen, a fibrillar collagen found in cartilage and the vitreous humor of the eye. Mutations in this gene are associated with achondrogenesis, chondrodysplasia, early onset familial osteoarthritis, SED congenita, Langer-Saldino achondrogenesis, Kniest dysplasia, Stickler syndrome type I, and spondyloepimetaphyseal dysplasia Strudwick type. Defects in processing chondrocalcin, a calcium binding protein that is the C-propeptide of this collagen molecule, are also associated with chondrodysplasia.

The human Runx2 gene is a member of the RUNX family of transcription factors and encodes a nuclear protein with an Runt DNA-binding domain. This protein is essential for osteoblastic differentiation and skeletal morphogenesis and acts as a scaffold for nucleic acids and regulatory factors involved in skeletal gene expression. The protein can bind DNA both as a monomer and, with more affinity, as a subunit of a heterodimeric complex. Two regions of potential trinucleotide repeat expansions are present in the N-terminal region of the encoded protein, and these and other mutations in this gene have been associated with the bone development disorder cleidocranial dysplasia (CCD).

The human collagen type X alpha 1 gene encodes the alpha chain of type X collagen, a short chain collagen expressed by hypertrophic chondrocytes during endochondral ossification. Mutations in this gene are associated with Schmid type metaphyseal chondrodysplasia (SMCD) and Japanese type spondylometaphyseal dysplasia (SMD).

MMP-13 belongs to the collagenase subfamily of MMPs and has broad substrate specificity for type II collagen and other ECM macromolecules. Aberrant expression of MMPs mediates malignant growth and invasion of tumor cells, and is pivotal in the pathogenesis of arthritis.

CD248 is expressed by cells of mesenchymal origin, including murine embryonic fibroblasts (MEF), vascular smooth muscle cells, pericytes, myofibroblasts, stromal cells and osteoblasts. During embryonic development, CD248 is prominently and widely expressed in the fetus. However, after birth, CD248 protein levels are dramatically down-regulated, resulting in only minimal expression in the healthy adult, except in the endometrium, ovary, renal glomerulus and osteoblasts. While largely absent in normal tissues, CD248 is markedly upregulated in almost all cancers. Highest expression is found in neuroblastomas and in subsets of carcinomas, such as breast and colon cancers, and in glioblastomas and mesenchymal tumors, such as fibrosarcomas and synovial sarcomas, where it is mostly detected in perivascular and tumor stromal cells, but also in the tumor cells themselves. CD248 is also expressed in placenta and during wound healing and in wounds such as ulcers. It is also prominently expressed in synovial fibroblasts during inflammatory arthritis. In some tumors and in chronic kidney disease, CD248 expression directly correlates with worse disease and/or a poor prognosis.

The receptor activator of nuclear factor kappa B ligand (RANKL) is a critical osteoclastogenic factor involved in the regulation of bone resorption, immune function, the development of mammary gland and cardiovascular system.

The reporter gene-labeled constructs within the mJoint bioreactor permit convenient read-out of tissue anabolic and catabolic states during the modeling of tissue degeneration in the mJoint system. These methods can use, for example, and adenovirus or an adenovirus associate virus construct encoding a maker, such as green fluorescent protein (GFP). In some embodiments, an inducible promoter is used, such as a promoter for an anabolic or catabolic gene.

Exemplary Embodiments

Clause 1: A tissue bioreactor that mimics an osteochondral complex of a mammalian joint, the bioreactor comprising: a first reactor chamber containing osseous or osteogenic tissue and/or cartilaginous or chondrogenic tissue; a second reactor chamber containing synovial tissue; a third reactor chamber containing adipose tissue, adipogenic tissue, or macrophages; a first fluidic passageway that forms a fluid circuit for circulating hypoxic tissue-specific nutrient medium through the first and second reactor chambers but not the third reactor chamber; a second fluidic passageway that forms a fluid circuit for circulating normoxic tissue-specific nutrient medium through the first, second and third reactor chambers; a perturbation source configured to provide a preselected perturbation to at least one of the reactor chambers or one or both of the first and second fluidic passageways.

Clause 2: The tissue bioreactor of clause 1, wherein the third reactor chamber contains adipose or adipogenic tissue and the tissue bioreactor further comprises a fourth reactor chamber containing macrophages, wherein the second fluidic passageway circulates the normoxic tissue-specific fluid through the third and fourth reactor chambers.

Clause 3: The tissue bioreactor of clause 1, wherein the first reactor chamber contains both osseous and cartilaginous tissue, and wherein the osseous tissue and the cartilaginous tissue are in separate layers.

Clause 4: The tissue bioreactor of clause 2, wherein the first, second, third and fourth reactor chambers are microscale chambers.

Clause 5: The tissue bioreactor of clause 1, wherein the perturbation source provides the preselected perturbation to only one of the first or second fluidic passageways.

Clause 6: The tissue bioreactor of clause 2, wherein the first reactor chamber, the second reactor chamber, the third reactor chamber and the fourth reactor chamber are in separate microwells.

Clause 7: The tissue bioreactor of any one of clause 1, wherein the osseous or tissue comprises osteocytes, the chondrogenic tissue comprises chondrocytes, and the adipose tissue comprises adipocytes.

Clause 8: The tissue bioreactor of clause 1, wherein the osteogenic or chondrogenic tissue comprises mesenchymal stem cells (MSCs) or induced pluripotent stem cells (iPSCs) that produce osteocytes or chondrocytes.

Clause 9: The tissue bioreactor of clause 1, wherein the adipogenic tissue comprises mesenchymal stem cells (MSCs) or induced pluripotent stem cells (iPSCs) that produce adipocytes.

Clause 10: The tissue bioreactor of clause 1, wherein the third reactor chamber comprises macrophages, and the tissue bioreactor further comprises a fourth bioreactor chamber comprising osseous but not cartilaginous tissue.

Clause 11: The tissue bioreactor of clause 1, wherein a) the bioreactor comprises a clear portion through which tissue may be observed visually, or b) wherein one or more of the first reactor chamber, the second reactor chamber, and the third reactor chamber comprise a clear portion through which tissue may be observed visually.

Clause 12: The tissue bioreactor of clause 3, further comprising a mesenchymal stem cell layer between the separate layers of osseous and cartilaginous tissue.

Clause 13: A tissue bioreactor that mimics a mammalian joint, the bioreactor comprising: a first reactor chamber containing separate layers of osteocytes and chondrocytes separated by a layer of mesenchymal cells; a second reactor chamber containing synovial tissue; a third reactor containing macrophages; a fourth reactor containing adipose cells; a first fluidic passageway that forms a fluid circuit for circulating hypoxic tissue-specific cell culture medium through the first and second reactor but not the third reactor; a second fluidic passageway that forms a fluid circuit for circulating normoxic tissue-specific cell culture medium through the first, second and third reactor; a perturbation source configured to provide a preselected perturbation to at least one of the reactor chambers, or one or both of the first and second fluidic passageways.

Clause 14: A method of mimicking biological conditions in a mammalian joint, comprising: circulating hypoxic cell culture medium through the first fluidic passageway and a normoxic cell culture medium through the second fluidic passageway of the tissue bioreactor of clause 13.

Clause 15: The method of clause 14, wherein the cells are all from one subject.

Clause 16: The method of clause 14, further comprising introducing a preselected biological perturbation into at least one of the first and second fluidic passageways.

Clause 17: The method of clause 16, wherein the preselected perturbation comprises one or more of a chemical perturbation, a toxicological perturbation, a mechanical perturbation, a physical perturbation, a biological perturbation, a disease initiator, an active agent, a chemical compound, a hormone, an inflammatory agent, a disease-modifying agent or a therapeutic agent.

Clause 18: The method of clause 17, wherein the preselected perturbation comprises one or more of a disease initiator, an active agent, a chemical compound, a hormone, an inflammatory agent, a disease-modifying agent or a therapeutic agent.

Clause 19: The method of clause 14, wherein the first and second fluidic passageways transport fluids to and from chambers by diffusion or perfusion.

Clause 20: The method of clause 17, wherein the disease modifying agent is one or more of an anti-osteoarthritic agent, anti-diabetic agent, a cartilage anabolic or catabolic gene sequence, a bone anabolic or catabolic gene sequence, a macrophage stimulator, or a macrophage inhibitor.

Clause 21: The method of clause 17, wherein the biological perturbation comprises wear debris, and the one or more tissues comprise macrophages.

Clause 22: The method of clause 21, wherein the macrophages are generated from mesenchymal stem cells or induced pluripotent stem cells within the bioreactor.

Clause 23: The method of clause 21, wherein the bioreactor comprises a clear sealing lid, and the effect of the biological perturbation is monitored through the sealing lid.

Clause 24: A bioreactor comprising three or more chambers wherein: a first chamber contains a first and a second tissue having one or more types of cells; a second chamber contains a third tissue having one or more types of cells; a third chamber contains a fourth tissue having one or more types of cells; wherein the first tissue, the second tissue, the third tissue and the fourth tissue are all distinct; wherein a type of cells is oriented vertically relative to a different type of cells within the same chamber, such that one type of cells is in functional contact with a different type of cells within the same chamber; a first nutrient fluid supplied laterally into the bioreactor; a second nutrient fluid supplied laterally into the bioreactor; wherein the first and second nutrient fluids maintain separation from each other through the functional contact between the first and second tissues; wherein each type of cells is only exposed to their tissue-specific medium while remaining in direct contact with each other; and a perturbation source configured to provide a preselected perturbation on at least one of the tissues.

Clause 25: The bioreactor of clause 22, wherein the first tissue in the first chamber comprises osteoblasts, the second tissue in the first chamber comprises chondrocytes, and wherein there is an additional tissue layer between the first tissue and the second tissue in the first chamber.

Clause 26: The bioreactor of clause 25, wherein the osteoblasts and chondrocytes are engineered from mesenchymal stem cells or induced pluripotent stem cells within the bioreactor.

Clause 27: The bioreactor of clause 25, wherein the additional tissue layer comprises mesenchymal stem cells, and wherein the additional tissue layer physically isolates the first and second tissues from one another.

Clause 28: The bioreactor of clause 22, wherein the third tissue in the second chamber comprises synovial cells.

Clause 29: The bioreactor of clause 26, wherein the synovial cells are generated from mesenchymal stem cells or induced pluripotent stem cells within the bioreactor.

Clause 30: The bioreactor of clause 23, wherein the fourth tissue in the third chamber comprises fat pad cells.

Clause 31: The bioreactor of clause 28, wherein the fat pad cells are generated from mesenchymal stem cells or induced pluripotent stem cells within the bioreactor.

Clause 32: The bioreactor of clause 23, further comprising a fourth chamber comprising macrophages.

Clause 33: The bioreactor of clause 30, wherein the macrophages are generated from mesenchymal stem cells or induced pluripotent stem cells within the bioreactor.

Clause 34: The bioreactor of clause 23, wherein the preselected perturbation is one or more of a chemical perturbation, a toxicological perturbation, a mechanical perturbation, a physical perturbation, or a biological perturbation.

Clause 35: The bioreactor of clause 32, wherein the preselected perturbation comprises one or more of a disease initiator, an active agent, a chemical compound, a hormone, an inflammatory agent, a disease-modifying agent or a therapeutic agent.

Clause 36: The bioreactor of clause 23, wherein the first and second nutrient fluids transport fluids and molecules to and from the chambers by diffusion.

Clause 37: The bioreactor of clause 23, wherein the first and second nutrient fluids transport fluids and molecules to and from the chambers by perfusion.

Clause 38: The bioreactor of clause 23, wherein the first nutrient fluid comprises serum in high concentration under normoxic conditions.

Clause 39: The bioreactor of clause 23, wherein the second nutrient fluid comprises serum in low concentration under hypoxic conditions.

Clause 40: The bioreactor of clause 23, wherein the one or more types of cells are from the same subject.

Clause 41: The bioreactor of clause 38, wherein the subject is a mammal with a disease.

Clause 42: The bioreactor of clause 39, wherein the disease is one or more of osteoarthritis, a diabetes-associated joint complication, osteosarcoma, or a bone tumor.

Clause 43: The bioreactor of clause 40, wherein the preselected perturbation comprises a disease-modifying agent.

Clause 44: The bioreactor of clause 41, wherein the disease modifying agent is one or more of an anti-osteoarthritic agent, anti-diabetic agent, a cartilage anabolic or catabolic gene sequence, a bone anabolic or catabolic gene sequence, a macrophage stimulator, or a macrophage inhibitor.

While portions of the present disclosure have been directed to the growth and study of bone and cartilage tissues, the devices, systems, and methods disclosed herein are applicable to various other biological tissues and structures. For example, the bioreactors and methods described herein can be used to facilitate the growth and/or study of any set of tissues, particularly a set of tissues in which interactions between the different tissues are suspected or known to exist and are a target for study. For example, a single layer of tissue or combinations of two, or three, or four, or five, or more layers of different tissues can be studied using the devices, systems, and methods disclosed herein. Specific examples include an osteochondral complex and chondrocyte complex without a mesenchymal complex, and various other examples provided above.

Example 1

To evaluate some of the devices, systems, methods, and techniques described herein, studies were conducted. Tissue engineering (TE) bone was formed by seeding human MSCs (4-20×10$^6$/ml) in gelatin/hydroxyapatite hydrogels by photocrosslinking, and cultured in BMP-2 included osteogenic media. Cartilage was engineered by seeding MSCs (4-60×10$^6$/ml) in gelatin/hyaluronic acid hydrogel by photocrosslinking, and treated with transforming growth factor-β3 (TGF-β3) included chondrogenic medium. Osteochondral interfaces were formed by placing layers of MSC-laden (4-20×10$^6$/ml) gelatin hydrogels between the chondral and osseous-constructs. This 3-layer TE osteochondral tissue was then inserted into the mold shown in FIGS. 5C and 5D and cultured in a chamber as shown in FIG. 6 with 2 separated fluid streams for 6 weeks. The upper fluid stream 384 supplied chondrogenic medium (CM) and the lower fluid stream 386 supplied osteogenic medium (OM) at a flow rate of 1 µl/s. [CM: Dulbecco's Modified Eagle's Medium (DMEM) supplemented with 10 ng/ml recombinant human TGF-β3 (Peprotech), 1% Insulin-Transferrin-Selenium, 50 µM ascorbic acid 2-phosphate, 55 µM sodium pyruvate, 23 µM L-proline, and 1% antibiotics-antimycotic. OM: α-MEM containing 10% fetal bovine serum, 1% antibiotics-antimycotic, 10 ng/ml recombinant human bone morphogenetic protein-2 (BMP-2; PeproTech), 1% L-alanyl-L-glutamine, 10 nM dexamethasone, 0.1 mM L-ascorbic acid 2-phosphate, and 10 mM β-glycerophosphate].

Next, a native bone and endothelial cell construct was prepared. The microvascular endothelial cell (EC) line HMEC-1 was maintained in EGM-2MV media (Lonza). Human bone plugs were harvested from human trabecular bone using 5.0 mm diameter biopsy hole punches (Miltex) and cultured in DMEM/10% FBS/1% PS for two weeks. EC-containing collagen gels were prepared using the 3D Collagen Culture Kit (Millipore) according to the manufacturer's instructions. Briefly, ice-cold 0.4 ml collagen solution was mixed with 0.1 ml 5×M199 medium and 12.5 al neutralization solution in 1.5 ml Eppendorf tubes. 25 al of EC solution (40×10$^6$ cells/ml DMEM) was added and mixed thoroughly. Bone plugs were then coated in EC/collagen gel by immersion in gel solution for 1 hour in a cell culture incubator. Native bone-EC constructs were cultured in 24-well plates containing 1 ml DMEM/10% FBS/1% PS per well for 0, 4, or 6 weeks.

Next, an osteoprotegerin enzyme-linked immunosorbent assay (ELISA) was performed. Native bone-EC constructs were washed in PBS and cultured in serum-free media for 4 days. Conditioned media samples were collected and analyzed by osteoprotegerin ELISAs (Abcam) exactly according to the manufacturer's instructions.

Next, histology and immunohistochemistry (IHC) was performed. TE bone-cartilage constructs and native bone-EC constructs were washed in PBS and fixed in 4% paraformaldehyde (Electron Microscopy Sciences) overnight at 4° C. Native bone-EC constructs were decalcified overnight in Decal® (Decal Chemical Corporation) at 4° C. To prepare samples for paraffin embedding, constructs were dehydrated by graded ethanol washes (30%, 50%, 70%, 95%, 100%), each overnight at 4° C., cleared in xylene for 1 hour at room temperature, and infiltrated with paraffin wax in 1:1 paraffin:xylene mix for 10 minutes at 60° C. Samples were incubated in 60° C. paraffin overnight to remove residual xylene, embedded, and sectioned (7 µm thickness).

For hematoxylin and eosin staining, samples were washed twice in Histo-Clear II (Electron Microscopy Sciences), rehydrated in graded ethanols (100%, 95%, 70%, 50%) for 1 min each, washed in deionized water for 1 min, stained in Gill No. 2 hematoxylin (Sigma-Aldrich) for 20 min, washed in running tap water for 1 min, immersed in acid alcohol (0.25% HCl in 70% ethanol) and then Scott's tap water substitute (10 g MgSO4, 0.75 g NaHCO$_3$, 1 L ddH2O) for 30 seconds each, washed in running tap water for 2 min, and stained in alcoholic eosin Y 515 (Leica) for 1 min. The samples were then dehydrated in graded ethanols (95%, 100%) for 1 min each, washed twice with Histo-Clear II for 1 min each, mounted with Clarion Mounting Media (Biomeda), and coverslipped.

For IHC, samples were rehydrated via gradient ethanol washes (100%, 95%, 70%, 50%) for 1 min each and washed in running tap water for 5 min. Following antigen retrieval via citrate buffer, pH 6.0 (eBioscience) for 40 min at 90° C., endogenous peroxidase activity was blocked with 3% H2O2 in methanol for 10 min at room temperature. Samples were then incubated with 1% horse serum for 45 min at room temperature and primary antibody (osteoprotegerin (Abcam), osteocalcin (Abcam)) diluted 1:200 with 1% horse serum overnight at 4° C. in humidified chambers. Following washes with PBS, samples were incubated with biotinylated secondary antibody (Vector Labs) for 30 min at RT, washed with PBS, incubated with HRP-conjugated streptavidin (Vector Labs) for 30 min at RT, washed with PBS, incubated with Vector® NovaRed™ peroxidase substrate for 1 min, washed with tap water, counterstained with hematoxylin OS (modified Mayer's formula) (Vector) for 3 seconds, washed in running tap water for 5 min, dehydrated in graded ethanols (95%, 100%) for 5 min each, washed twice in Histo-Clear II for 5 min each, mounted with Clarion Mounting Medium, and coverslipped. Histology and IHC images were captured with an Olympus CKX41 microscope outfitted with a Leica DFC 3200 camera.

Example 2

The disclosed reactors can achieve cellular communication between the different tissues in the two compartments of the reactor, and each signals to the other in response to changes in the local environment. In a specific example, when bone is stimulated by hormones simulating the menstrual cycle, the hormones initiate an anabolic response and signal to cartilage that will respond even without direct exposure to the hormones. The ability to study this phenomenon is particularly important because hormonal exposure has a protective effect against bone volume loss. To evaluate this effect, a first experiment used a native osteochondral plug.

For the osteochondral plug experiment, human osteochondral plugs from the knees of women undergoing total knee replacement were explanted from macroscopically asymptomatic regions of the joint. Three treatment groups were evaluated with different fluid flow between the top (cartilage) and lower (bone) chambers of the bioreactor. The fluid flows to the top and bottom chambers included Dulbecco's Modified Eagle Media (DMEM), Fetal Bovine serum (FBS), and Penicillin/Streptomycin/Amphotericin (PSF), optionally with hormones that simulate the menstrual cycle. The treatment groups were as follows:

Treatment Groups:
1. Top: DMEM+FBS+PSF
   Bottom: DMEM+FBS+PSF
2. Top: DMEM+FBS+PSF+hormones simulating the menstrual cycle
   Bottom: DMEM+FBS+PSF
3. Top: DMEM+FBS+PSF
   Bottom: DMEM+FBS+PSF+hormones simulating the menstrual cycle For the groups in which hormones were supplied, the media was altered over the following time course:

| | | DAY | | | | | | | | | | | | | | |
|---|---|---|---|---|---|---|---|---|---|---|---|---|---|---|---|---|
| | | −2 | −1 | 0 | 1 | 2 | 3 | 4 | 5 | 6 | 7 | 8 | 9 | 10 | 11 | 12 | 13 |
| Media | Growth media | | | 0.1 nM Estradiol | | | | | | | | 1 nM Estradiol | | | | | |

| | DAY | | | | | | | | | | | | | |
|---|---|---|---|---|---|---|---|---|---|---|---|---|---|---|
| | 14 | 15 | 16 | 17 | 18 | 19 | 20 | 21 | 22 | 23 | 24 | 25 | 26 | 27 |
| Media | 1 nM Estradiol + 10 nm Progesterone | | | | | | | 0.1 nM Estradiol + 50 nm Progesterone | | | | | | |

The result showed that hormones affected both bone and cartilage. In particular, hormone treatment reduced osteocalcin secretion and enhanced osteoprotegerin secretion. The results also provided evidence of a cyclic bone response to changing concentrations of hormones that mimicked changes that would be seen throughout the menstrual cycle of a woman. The hormones prevented loss of calcification in the osteochondral junction.

Example 3

In another demonstration of the use of the bioreactor, a chondrocyte response was shown using real time PCT (RT-PCR) to illustrate that stimulation of bone tissue in the lower chamber of the bioreactor stimulated a chondrocyte response in the upper chamber. Differential expression of markers (as determined by RT-PCR) was evaluated in a control medium that contained no estrogen or progesterone (first bar), and then different concentrations of hormones supplied to the chambers during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone).

Differential expression of markers was determined in a control medium that contained no estrogen or progesterone (first bar), and then different concentrations of hormones supplied to the cartilage chamber during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone). Two conditions were tested: "direct hormone stimulation" wherein the hormones were supplied to the bone (bottom) chamber of the bioreactor; and "chondrocytes mediated stimulation" wherein the hormones were supplied to the cartilage (top) chamber of the bioreactor and had an indirect effect on the osteoblasts in the bone chamber.

Higher concentrations of estradiol in the bone chamber of the bioreactor downregulated cartilage anabolic markers such as Sox9 and Aggrecan, but downregulation is more pronounced when estradiol is applied to the osseous side. When progesterone is progressively added (week 3 and 4), downregulation is still present but with an opposite trend (higher when hormones are directly applied to cartilage). Bone anabolic markers are generally downregulated in all conditions. Cartilage hypertrophy marker ColX is upregulated only when estradiol is administered to the osseous side, and downregulated in any other conditions, suggesting a concomitant signaling from osteoblasts. Metalloproteinases are generally upregulated in cartilage for all conditions (except MMP-13 which has a more complex behavior).

Metalloproteinases are generally downregulated in bone for all conditions (except MMP-3 which has a more complex behavior). Bone anabolic markers are generally downregulated in all conditions.

Example 4

The differentiation and development of engineered osteochondral tissue in the disclosed mJoint bioreactor were monitored to determine formation of cartilaginous and bone matrices. iPSC-derived joint cells or MSC-derived joint cells were encapsulated within a photo-crosslinkable methacrylated gelatin (mGL) and placed in a top chamber in the mJoint bioreactor. In some examples, endothelial cells were seeded with the iPSC-derived joint cells or MSC-derived joint cells into the osseous component of the osteochondral mJoint bioreactor. The top chamber containing the mGL encapsulating the iPSC-derived joint cells or MSC-derived joint cells was then placed on top of a bottom chamber containing a polycaprolactone scaffold that constituted the osseous component to create a 3D biphasic mJoint osteochondral construct containing two independent microfluidic networks. The top and bottom chambers were fluidically connected to two controlled flow loops and supplied with independently tuned differentiation parameters for chondrogenic and osteogenic induction, respectively. The osseous component in the bottom chamber was connected to a medium with high serum concentration under normoxia, and the chondral component in the top chamber was connected to a medium with low serum concentration under hypoxia. MSCs derived from subcutaneous adipose tissue were seeded in a separate chamber for the production of adipocytes, and the chamber was also connected to a medium with high serum concentration under normoxia.

Example 5

The specificity and responsiveness of gene promoter-reporter constructs were tested in the engineered osteocytes, chondrocytes and infrapatellar fat pad. Adult stem cells were transduced with Green Fluorescent Protein (GFP) constructs or Luciferase (Luc) constructs carrying different cartilage and bone anabolic and catabolic marker genes prior to being used to engineer chondral, osseous or adipose tissue components. The cartilage and bone anabolic and catabolic marker genes included the human Col II gene, the human Runx2 gene, the human collagen type X alpha 1 gene, the human MMP13 gene, the human CD248 (endosialin) gene, or the human RANKL gene. Transduction was carried on in the presence or absence of the pro-inflammatory cytokine IL-1β. Cartilage and bone anabolic and catabolic genes were successfully detected in primary osteocytes and chondrocytes. The MMP and COLX genes were successfully detected in the engineered adipose-derived stem cells.

Example 6

Trauma, inflammation, infection, and aging cause damages to joint tissues, ultimately leading to degenerative disorders, such as osteoarthritis (OA), septic arthritis, and inflammatory arthritis, resulting in painful physical disabilities that compromise quality of life. However, no effective therapies are currently available. The limited progress in the development of disease-modifying medications (DMMs) is principally because of: (1) insufficient mechanistic understanding of disease onset/progression; (2) inability to address the 3-dimensional (3D) and multi-tissue nature of the synovial joint in early phase in vitro drug discovery; and (3) limited utility of pre-clinical animal studies for early stage clinical efficacy and toxicity prediction (lacking "fail early/fail fast" capabilities), contributing to unanticipated and costly clinical trial failures. Also, patient-specific etiology, progression, and drug sensitivity profiles underscore the need for individualized therapy. To address these needs, a 3D human micro-joint chip (mJoint) was engineered, which was physiologically analogous to the native joint, and capable of modeling pathogenesis of joint diseases for DMM screening/development.

Figure 24A:
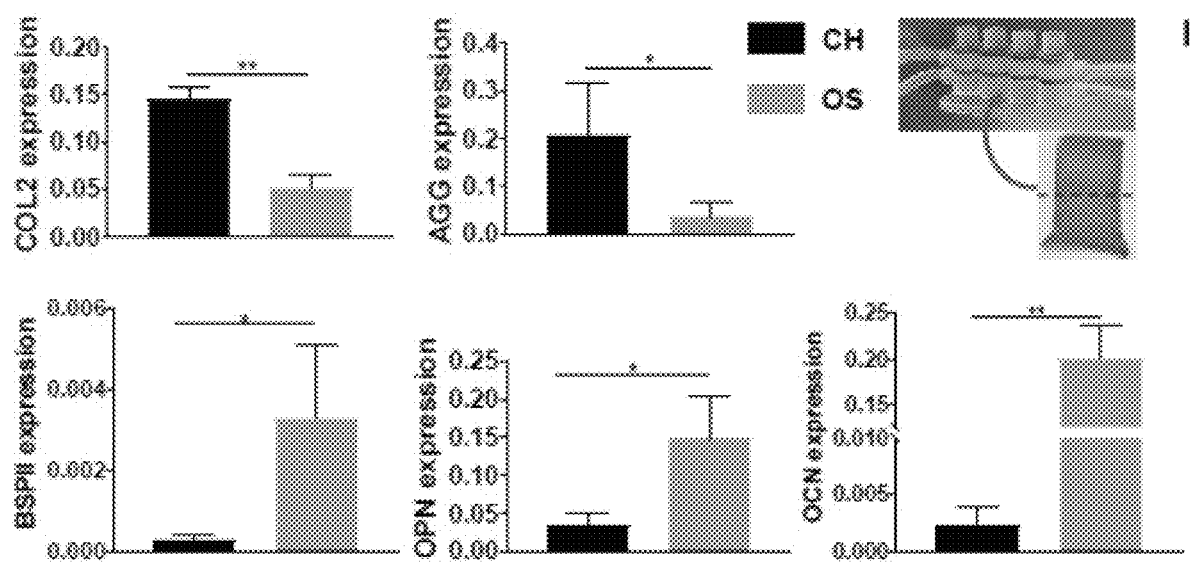
FIGS. 24A-24B. Engineering of iMPC-derived osteochondral complex by culturing cell-laden GelMA scaffolds in a dual flow bioreactor. (A) Expression of bone and cartilage marker genes in the chondral or osseous parts of; (B) Alcian blue (left) and Alizarin Red (right) staining. CH: chondral, OS: osseous.
Figure 24B:
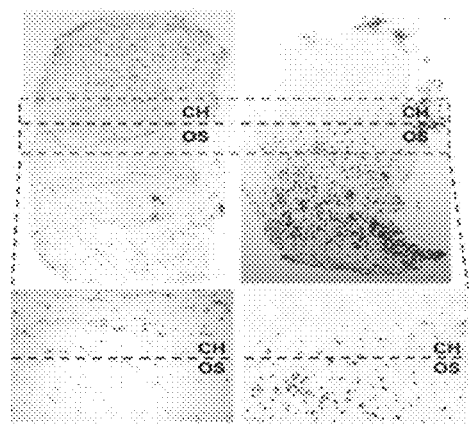
Figure 25A:
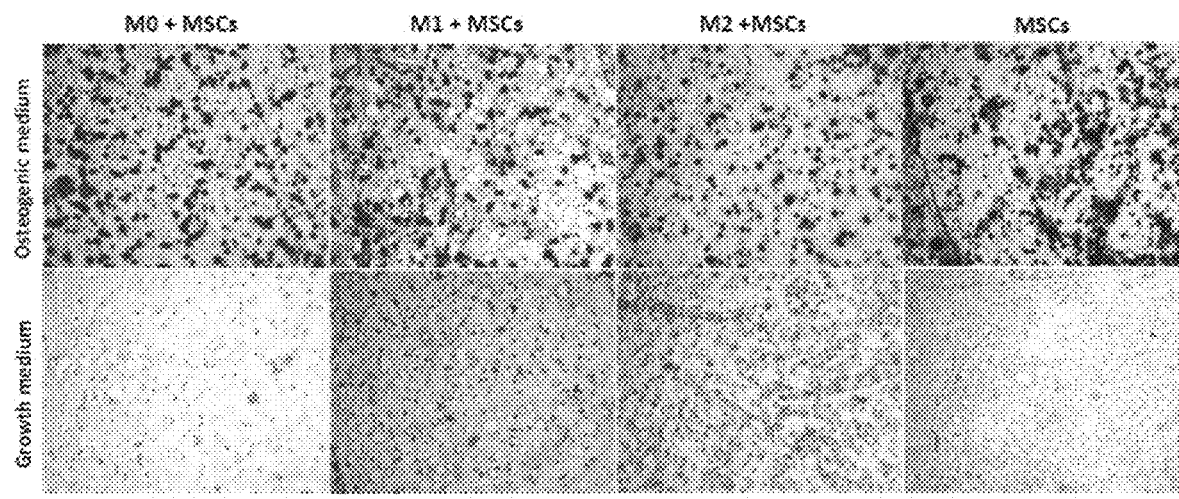
FIGS. 25A-25B. Generation of osseous tissues with the inclusion of macrophages at different stages: (A) Alizarin Red staining on D28; (B) TNF-α (M1 marker) secretion quantified by ELISA. Cell number: 1,250,000 Macrophages+250,000 hMSCs or 250,000 hMSCs alone. No detectable ELISA signal was seen in cultures with MSCs only.
Figure 25B:
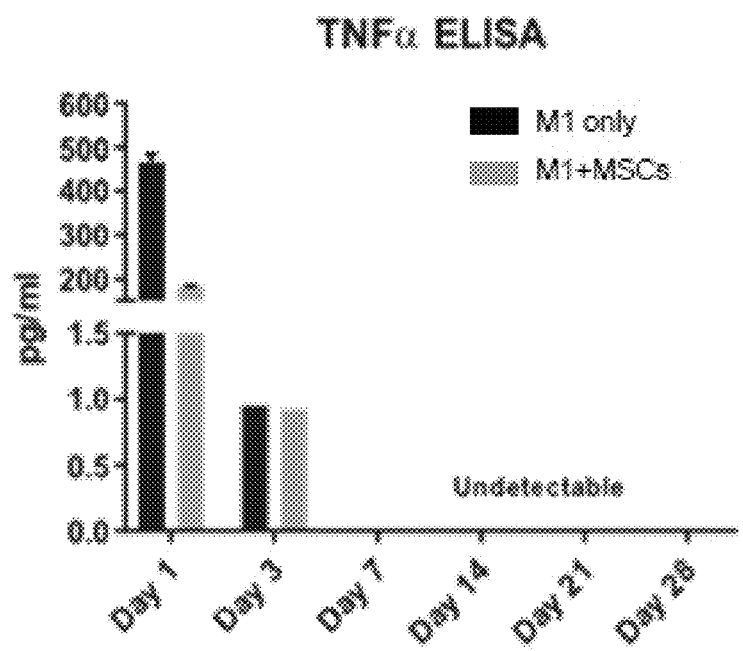

Osteochondral, synovium (containing fibroblasts) and adipose tissues were successfully engineered from both primary human MSCs and iPSCs (FIG. 24). In addition, the co-culture of primary macrophages (derived from human monocytes) and MSCs within 3D methacrylated gelatin (GelMA) scaffolds resulted in robust osteogenesis upon stimulation. In addition, in-scaffold macrophages were able to be polarized to M1 or M2 phenotypes with corresponding secretome (FIG. 25).

Pre-differentiated osteochondral units, synovium and fat pad tissues were then integrated in the 3D printed bioreactors (FIGS. 26C and 26E) to generate microJoint chip under normal physiology. FIG. 26G showed that the phenotypes of the osteochondral units could be well maintained after 28 days of integration, with the use of either tissue specific medium (OM) or universal growth media (GM) in streams 1-3 (FIG. 26C). Basic chondrogenic medium (CM) was used in stream 4.

To model OA in the microJoint, the pro-inflammatory cytokine interleukin (IL)-1β (10 ng/mL) was used to stimulate synovial cells for 24 h. Afterwards, IL-1β was withdrawn and inflamed synovium-conditioned medium was perfused through cartilage and FP tissues. IL-1β treatment significantly upregulated the expression levels of major catabolic genes (FIG. 26A) in SM, indicating the successful generation of inflamed synovium. When medium conditioned by such inflamed SM tissues flowed through the cartilage tissues, characteristic cartilage markers were markedly reduced; at the same time, expression levels of MMP13 and ATS4, which are associated with the degradation of cartilage matrix, were significantly upregulated (FIG. 27B). The results suggested the generation of degenerative arthritis in mJoint chip through insulting synovium. M0/M1 macrophages can be introduced into the different tissues to investigate their interactions with other cells and implications on OA pathologies.

Example 7

Different engineered joint tissues, including osteochondral complex (bone and cartilage), synovium, and fat pad were prepared as modules for convenient integration in the bioreactor. After maturation, they were integrated into a bioreactor (FIG. 28). Their interconnection was guided via directional fluidic flow of the culture medium to simulate in vivo physiology (FIG. 29). The bioreactors and accessories were manufactured by 3D printing. Micro-tissues were engineered by encapsulating P5 human MSCs in UV-photocrosslinked 15% methacrylated gelatin (GelMA), and differentiating and maturing them in different types of induction media. The health of individual tissues was assessed by real-time polymerase chain reaction (RT-PCR), histology and enzyme-linked immunosorbent assay (ELISA).

Figure 31:
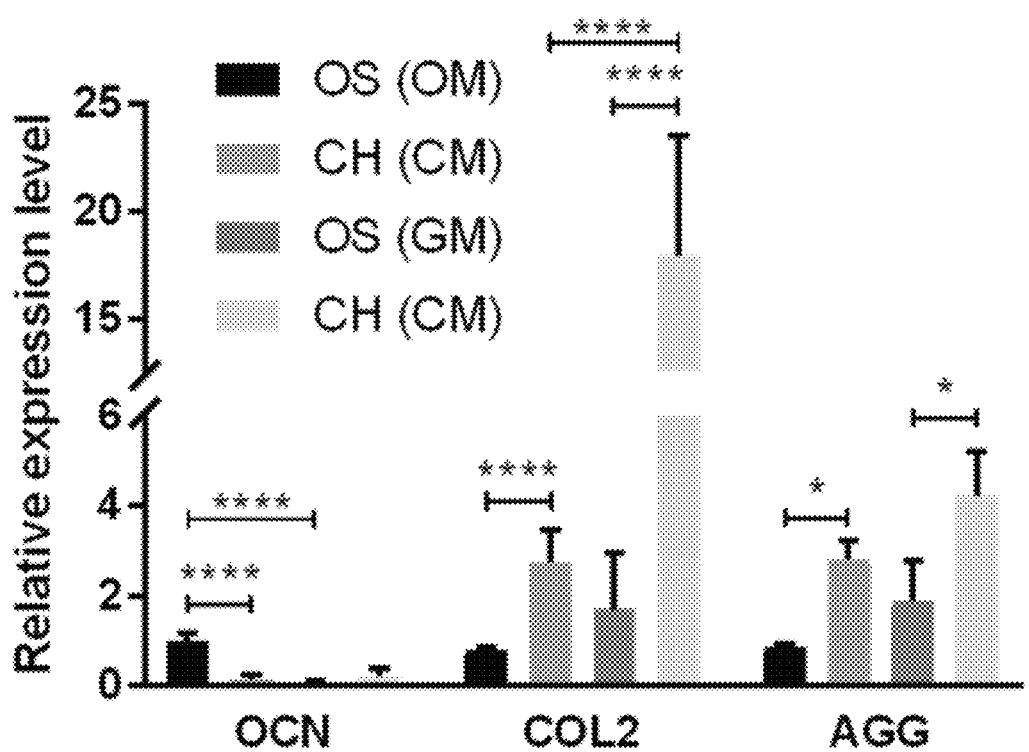
FIG. 31. Expression of bone (OS) and cartilage (CH) marker genes after 28 days integration culture. OS was cultured in osteogenic medium (OM), or Universal medium M (GM). CH was cultured in Universal medium C (CM). OCN=osteocalcin, which is a bone marker gene. COL2=collagen type II; AGG=aggrecan, which are cartilage marker genes.

RT-PCR and histological staining both confirmed that individual joint components within the mJoint chip were able to maintain respective tissue-specific phenotypes up to 4 weeks, as reveal by real time PCR (FIG. 31) and histology. FIG. 30, presents representative histological images of the osteochondral complex that showed calcium deposition in the osseous component (OS, Alizarin Red staining) and glycosaminoglycans formation in the chondral component (CH, Safranin O/fast green staining). Herovici staining indicated the presence of both old and young collagen in the engineered synovial membrane (SM), and robust oil drop formation (by Oil Red O staining) was observed in the fat pad compartment.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A bioreactor comprising:
   i) a first chamber comprising an upper part and a lower part, wherein the upper part of the first chamber comprises a first tissue comprising osteoblasts within a first scaffold, and the lower part of the first chamber comprises a second tissue comprising chondrocytes within a second scaffold;
   ii) a second chamber comprising an upper part and a lower part, each comprising synovial cells within a third scaffold;
   iii) a third chamber comprising an upper part and a lower part, each comprising fat pad cells within a fourth scaffold;
   iv) a first influx that supplies a first nutrient fluid to the upper part of the first chamber, and a first efflux conduit that removes the first nutrient fluid from the upper part of the first chamber;
   v) a second influx conduit that supplies a second nutrient fluid to the lower part of the first, second, and third chambers, and a second efflux conduit that removes the second nutrient fluid from the lower part of the first, second, and third chambers;

vi) a third influx conduit that supplies a third nutrient fluid to the upper part of the second chamber, and a third efflux conduit that removes the third nutrient fluid from the upper part of the second chamber; and vii) a fourth influx conduit that supplies a fourth nutrient fluid to the upper part of the third chamber, and a fourth efflux conduit that removes the fourth nutrient fluid from the upper part of the third chamber;

and wherein:

the lower parts of the first, second, and third chambers are interconnected;

the second nutrient fluid maintains separation from the first, third, and fourth nutrient fluids through functional contact between the upper and lower parts of the first, second and third chambers;

the first tissue is exposed to the first nutrient fluid and not the second, third, or fourth nutrient fluids;

the second tissue is exposed to the second nutrient fluid and not the first, third, and fourth nutrient fluids;

the first and second tissues remain in direct contact with each other; and a perturbation source that provides a preselected perturbation to at least one of the first, second, or third chambers of the bioreactor.

2. The bioreactor of claim 1, wherein the osteoblasts, chondrocytes, synovial cells and/or fat pad cells are produced from mesenchymal stem cells or induced pluripotent stem cells within the bioreactor.

3. The bioreactor of claim 1, wherein there is an additional tissue layer comprising mesenchymal stem cells or a semipermeable membrane between the osteoblasts and the chondrocytes in the first chamber.

4. The bioreactor of claim 1, further comprising a fourth chamber comprising an upper part and a lower part, each comprising macrophages within a fifth scaffold, wherein the lower parts of the first, second, third, and fourth chambers are all interconnected.

5. The bioreactor of claim 4, wherein the first, second, third and fourth chambers are interconnected such that the second nutrient fluid entering through the second influx conduit contacts the chondrocytes in the first chamber, the synovial cells in the second chamber, the fat pad cells in the third chamber, and the macrophages in the fourth chamber.

6. The bioreactor of claim 1, wherein the preselected perturbation is one or more of a chemical perturbation, a toxicological perturbation, a mechanical perturbation, a physical perturbation, a biological perturbation, a disease initiator, an active agent, a chemical compound, a hormone, an inflammatory agent, a disease-modifying agent or a therapeutic agent.

7. The bioreactor of claim 6, wherein the disease modifying agent is one or more of an anti-osteoarthritic agent, anti-diabetic agent, a cartilage anabolic or catabolic gene sequence, a bone anabolic or catabolic gene sequence, a macrophage stimulator, or a macrophage inhibitor.

8. The bioreactor of claim 1, wherein the osteoblasts, chondrocytes, synovial cells and/or fat pad cells are from the same subject or stem cell.

9. The bioreactor of claim 8, wherein the subject is a mammal with a disease, and wherein the disease is one or more of osteoarthritis, a diabetes-associated joint complication, osteosarcoma, or a bone tumor.

10. The bioreactor of claim 1, wherein the first, second, and third chambers are interconnected, such that the second nutrient fluid entering through the second influx conduit contacts the chondrocytes in the first chamber, the synovial cells in the second chamber, and the fat pad cells in the third chamber.

11. The bioreactor of claim 1,
wherein the first nutrient fluid is normoxic; and
wherein the second nutrient fluid is hypoxic.

12. The bioreactor of claim 11,
wherein the third nutrient fluid is normoxic and comprises 10% to 20% serum.

13. The bioreactor of claim 12,
wherein the fourth nutrient fluid is normoxic and comprises 10% to 20% serum.

14. A method of reproducing the biological conditions in a mammalian joint, comprising:

circulating, in the bioreactor of claim 1, the first nutrient fluid through the upper part of the first chamber of the bioreactor and circulating the second nutrient fluid through the lower part of the first, second, and third chambers of the bioreactor;

thereby reproducing the biological conditions in a mammalian joint.

15. The method of claim 14, further comprising introducing the preselected perturbation into at least one of the first, second, or third chambers of the bioreactor.

16. The method of claim 15, wherein the preselected perturbation comprises one or more of a chemical perturbation, a toxicological perturbation, a mechanical perturbation, a physical perturbation, a biological perturbation, a disease initiator, an active agent, a chemical compound, a hormone, an inflammatory agent, a disease-modifying agent or a therapeutic agent.

17. A method of reproducing the biological conditions in a mammalian joint, comprising:

circulating, in the bioreactor of claim 1, the first nutrient fluid through the upper part of the first chamber of the bioreactor comprising the osteoblasts;

circulating the third nutrient fluid through the upper part of the second chamber of the bioreactor comprising the synovial cells;

circulating the fourth nutrient fluid through the upper part of the third chamber of the bioreactor comprising the fat pad cells;

circulating the second nutrient fluid through the lower parts of the first, second, and third chambers of the bioreactor; wherein the second nutrient fluid contacts the chondrocytes in the lower part of the first chamber, the synovial cells in the lower part of the second chamber, and the fat pad cells in the lower part of the third chamber;

thereby reproducing the biological conditions in a mammalian joint.

18. The method of claim 17, further comprising introducing the preselected perturbation into at least one of the first, second, or third chambers of the bioreactor.

19. The method of claim 18, wherein the preselected perturbation comprises one or more of a chemical perturbation, a toxicological perturbation, a mechanical perturbation, a physical perturbation, a biological perturbation, a disease initiator, an active agent, a chemical compound, a hormone, an inflammatory agent, a disease-modifying agent or a therapeutic agent.

* * * * *

UNITED STATES PATENT AND TRADEMARK OFFICE
CERTIFICATE OF CORRECTION

| | | |
|---|---|---|
| PATENT NO. | : 11,339,362 B2 | Page 1 of 1 |
| APPLICATION NO. | : 16/193972 | |
| DATED | : May 24, 2022 | |
| INVENTOR(S) | : Lin et al. | |

It is certified that error appears in the above-identified patent and that said Letters Patent is hereby corrected as shown below:

On the Title Page

Under item (72), Inventors: "Riccardo Lucca Gottardi" should read --Riccardo Gottardi--

Signed and Sealed this
Twenty-sixth Day of March, 2024

Katherine Kelly Vidal
*Director of the United States Patent and Trademark Office*